United States Patent
Namai et al.

(10) Patent No.: US 9,703,195 B2
(45) Date of Patent: Jul. 11, 2017

(54) RADIATION-SENSITIVE RESIN COMPOSITION, RESIST PATTERN-FORMING METHOD, POLYMER, AND METHOD FOR PRODUCING COMPOUND

(71) Applicant: JSR CORPORATION, Tokyo (JP)

(72) Inventors: Hayato Namai, Tokyo (JP); Kota Nishino, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/805,703

(22) Filed: Jul. 22, 2015

(65) Prior Publication Data
US 2015/0323866 A1  Nov. 12, 2015

Related U.S. Application Data

(63) Continuation of application No. PCT/JP2014/055344, filed on Mar. 3, 2014.

(30) Foreign Application Priority Data

Mar. 22, 2013 (JP) ................................ 2013-061138

(51) Int. Cl.
| | |
|---|---|
| G03F 7/039 | (2006.01) |
| G03F 7/32 | (2006.01) |
| G03F 7/20 | (2006.01) |
| C08F 12/32 | (2006.01) |
| C08F 12/22 | (2006.01) |
| C08F 220/18 | (2006.01) |
| C08F 212/14 | (2006.01) |
| C07D 307/93 | (2006.01) |
| C07D 307/33 | (2006.01) |
| C07D 327/04 | (2006.01) |
| C07D 493/18 | (2006.01) |
| C08F 220/28 | (2006.01) |

(52) U.S. Cl.
CPC ........... *G03F 7/039* (2013.01); *C07D 307/33* (2013.01); *C07D 307/93* (2013.01); *C07D 327/04* (2013.01); *C07D 493/18* (2013.01); *C08F 12/22* (2013.01); *C08F 12/32* (2013.01); *C08F 212/14* (2013.01); *C08F 220/18* (2013.01); *C08F 220/28* (2013.01); *G03F 7/0397* (2013.01); *G03F 7/2041* (2013.01); *G03F 7/322* (2013.01); *G03F 7/325* (2013.01)

(58) Field of Classification Search
None
See application file for complete search history.

(56) References Cited

U.S. PATENT DOCUMENTS

| | | | |
|---|---|---|---|
| 4,910,122 A | 3/1990 | Arnold et al. | |
| 5,395,736 A * | 3/1995 | Grasshoff | B41M 5/30 |
| | | | 430/269 |
| 6,010,826 A | 1/2000 | Abe et al. | |
| 6,489,065 B1 | 12/2002 | Dhal et al. | |
| 8,603,726 B2 | 12/2013 | Nakahara et al. | |
| 2005/0260525 A1 | 11/2005 | Takemoto et al. | |
| 2008/0193874 A1 | 8/2008 | Takata et al. | |
| 2010/0297555 A1 | 11/2010 | Koyama et al. | |
| 2012/0082934 A1 * | 4/2012 | Nakahara | C07C 205/52 |
| | | | 430/285.1 |

FOREIGN PATENT DOCUMENTS

| | | | |
|---|---|---|---|
| GB | 2 072 508 A1 * | 10/1981 | |
| JP | S52-069612 A | 6/1977 | |
| JP | S59-093448 A | 5/1984 | |
| JP | 1-179936 * | 7/1989 | |
| JP | H05-188598 A | 7/1993 | |
| JP | H06-012452 B2 | 2/1994 | |
| JP | H08-029985 A | 2/1996 | |

(Continued)

OTHER PUBLICATIONS

JPO English abstract for JP1-179936 (1989).*
Derwent English abstract for JP 8-29985 (1996).*
Machine-assisted English translation for JP 8-29985 (1996).*
Partial English translation of WO 92/16570 (for p. 6, line 10-p. 8, line 13 of the WO document) as provided by USPTO (1992).*
International Search Report issued May 27, 2014 in PCT/JP2014/055344 filed Mar. 3, 2014.
Office Action issued May 2, 2017, in Japanese Patent Application. No. 2013-268151 (w/computer-generated English translation).
Office Action issued May 23, 2017 in Japanese Application. No. 2015-506682 (w/computer-generated English translation).

*Primary Examiner* — Sin Lee
(74) *Attorney, Agent, or Firm* — Oblon, McClelland, Maier & Neustadt, L.L.P.

(57) ABSTRACT

A radiation-sensitive resin composition contains: a polymer having a structural unit that includes a group represented by formula (1); a radiation-sensitive acid generator; and an organic solvent. In the formula (1), $R^P$ represents a hydrogen atom or a monovalent organic group, and * denotes a binding site to a rest of the structural unit other than the group represented by the formula (1). It is preferred that $R^P$ in the formula (1) represents a monovalent organic group, and the monovalent organic group is an acid-nonlabile group. It is also preferred that $R^P$ in the formula (1) represents a monovalent organic group, and the monovalent organic group is an acid-labile group.

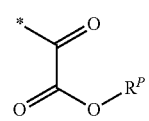

(1)

19 Claims, No Drawings

(56) References Cited

FOREIGN PATENT DOCUMENTS

| JP | H08-211613 A | 8/1996 |
| JP | H10-207069 A | 8/1998 |
| JP | H10-274852 A | 10/1998 |
| JP | 2000-026446 A | 1/2000 |
| JP | 2000-159758 A | 6/2000 |
| JP | 2000-511302 A | 8/2000 |
| JP | 2005-352384 A | 12/2005 |
| JP | 2005-352466 A | 12/2005 |
| JP | 2008-209917 A | 9/2008 |
| JP | 2010-150447 A | 7/2010 |
| JP | 2010-170054 A | 8/2010 |
| JP | 2010-185987 A | 8/2010 |
| JP | 201 0-1 91 01 | 9/2010 |
| JP | 2011-227437 A | 11/2011 |
| JP | 2012-092300 A | 5/2012 |
| JP | 2012-123376 A | 6/2012 |
| JP | 2012-256011 A | 12/2012 |
| JP | 2013-174715 A | 9/2013 |
| WO | WO 92/16570 * 10/1992 | ............. C08F 20/28 |
| WO | WO 92/16570 A1 | 10/1992 |
| WO | WO 97/44714 * 11/1997 | |
| WO | WO 2009/107327 A1 | 9/2009 |

* cited by examiner

RADIATION-SENSITIVE RESIN COMPOSITION, RESIST PATTERN-FORMING METHOD, POLYMER, AND METHOD FOR PRODUCING COMPOUND

CROSS-REFERENCE TO RELATED APPLICATIONS

The present application is a continuation application of International Application No. PCT/JP2014/055344, filed Mar. 3, 2014, which claims priority to Japanese Patent Application No. 2013-061138, filed Mar. 22, 2013. The contents of these applications are incorporated herein by reference in their entirety.

BACKGROUND OF THE INVENTION

Field of the Invention

The present invention relates to a radiation-sensitive resin composition, a resist pattern-forming method, a polymer, and a method for producing a compound.

Discussion of the Background

Upon irradiation with exposure light such as an ArF excimer laser beam or a KrF excimer laser beam, chemically amplified radiation-sensitive resin compositions generate an acid from an acid generator at a light-exposed site, and a reaction catalyzed by the acid causes a difference in rate of dissolution in a developer solution between a light-exposed site and a light-unexposed site, thereby forming a resist pattern on a substrate.

Along with the advance of microfabrication technologies, such radiation-sensitive resin compositions are demanded not only to have a superior resolution, but also to be capable of forming a highly accurate pattern that is advantageous in e.g., having a rectangular cross-sectional shape, and a small line-width-roughness (LWR) which is an indicative of a variation of the line width of the resist pattern. To address the demand, incorporation of various polar groups into a polymer contained in the radiation-sensitive resin composition has been investigated, and it is known that incorporation of a lactone ring such as a norbornanelactone ring or a γ-butyrolactone ring can improve adhesiveness while maintaining favorable sensitivity, resolution, and the like (see Japanese Unexamined Patent Application, Publication Nos. 2000-26446, 2000-159758, H10-207069, and H10-274852).

However, in these days when microfabrication of resist patterns has reached the level of a line width of no greater than 40 nm, the radiation-sensitive resin compositions are demanded not only to be further superior in the resolution and the rectangularity of the cross-sectional shape, but also to exhibit a superior depth of focus (DOF), and it is also demanded that a further accurate pattern can be formed in a high process yield.

SUMMARY OF THE INVENTION

According to one aspect of the present invention, a radiation-sensitive resin composition includes a polymer comprising a first structural unit that comprises a group represented by formula (1), a radiation-sensitive acid generator, and an organic solvent.

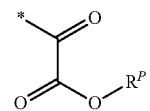
(1)

In the formula (1), $R^P$ represents a hydrogen atom or a monovalent organic group, and * denotes a binding site to a rest of the first structural unit other than the group represented by the formula (1).

According to another aspect of the present invention, a resist pattern-forming method includes providing a resist film using the radiation-sensitive resin composition. The resist film is exposed. The exposed resist film is developed.

According to further aspect of the present invention, a polymer includes a structural unit that includes a group represented by formula (1').

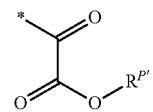
(1')

In the formula (1'), $R^{P'}$ represents a hydrogen atom, or an acid-nonlabile group obtained from a monovalent hydrocarbon group having 2 to 20 carbon atoms by incorporating between adjacent two carbon atoms thereof, —O—, —CO—, —CO—O—, —SO$_2$O— or a combination thereof; and * denotes a binding site to a rest of the structural unit other than the group represented by the formula (1').

According to further aspect of the present invention, a polymer includes a first structural unit that comprises a group represented by formula (1), and a structural unit represented by formula (3-1), a structural unit represented by formula (3-2), a structural unit represented by formula (3-3), a structural unit represented by formula (3-4), or a combination thereof.

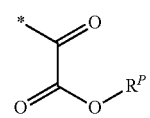
(1)

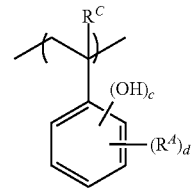
(3-1)

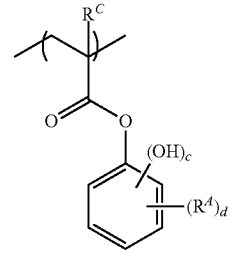
(3-2)

-continued (3-3)

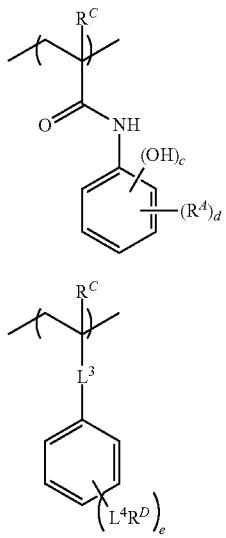

(3-4)

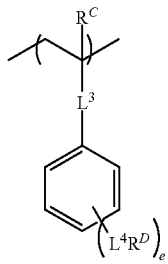

In the formula (1), $R^P$ represents a hydrogen atom or a monovalent organic group; and * denotes a binding site to a rest of the first structural unit other than the group represented by the formula (1). In the formulae (3-1) to (3-4), $R^C$s each independently represent a hydrogen atom or an alkyl group having 1 to 5 carbon atoms. In the formulae (3-1) to (3-3), "c"s are each independently an integer of 1 to 3; $R^A$s each independently represent an alkyl group having 1 to 5 carbon atoms; and "d"s are each independently an integer of 0 to 4, wherein a sum of c and d is no greater than 5, and wherein in a case where $R^A$ is present in a plurality of number, a plurality of $R^A$s are each identical or different. In the formula (3-4), $L^3$ and $L^4$ each independently represent a single bond, a methylene group, an alkylene group having 2 to 5 carbon atoms, a cycloalkylene group having 3 to 15 carbon atoms, an arylene group having 6 to 20 carbon atoms, or a divalent group obtained by combining a methylene group, an alkylene group having 2 to 5 carbon atoms, a cycloalkylene group having 3 to 15 carbon atoms or an arylene group having 6 to 20 carbon atoms with —O—, —CO— or a combination thereof; $R^D$ represents a hydrogen atom, a carboxy group, a monovalent chain hydrocarbon group having 1 to 5 carbon atoms, an alkoxy group having 1 to 5 carbon atoms, an alkoxycarbonyl group having 2 to 5 carbon atoms, or a group that comprises a hydroxy group at an end thereof and comprises at least one fluorine atom or fluorinated alkyl group on a carbon atom adjacent to the hydroxy group; and e is an integer of 1 to 5, wherein in a case where $L^4$ and $R^D$ are each present in a plurality of number, a plurality of $L^4$s are each identical or different and a plurality of $R^D$s are each identical or different.

According to further aspect of the present invention, a method for producing a compound represented by formula (i-1), includes reacting a compound represented by formula (i-a) with a compound represented by formula (i-b-1).

(i-a)

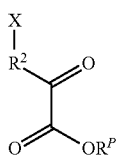

(i-b-1)

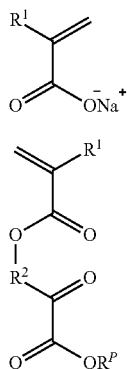

(i-1)

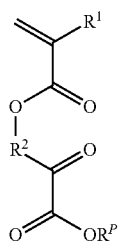

in the formulae (i-a), (i-b-1) and (i-1), $R^P$ represents a hydrogen atom or a monovalent organic group; X represents a halogen atom; $R^1$ represents a hydrogen atom, or a substituted or unsubstituted alkyl group having 1 to 5 carbon atoms; and $R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof.

According to further aspect of the present invention, a method for producing a compound represented by formula (i-2), includes reacting a compound represented by formula (i-a') with a compound represented by formula (i-b-2).

(i-a')

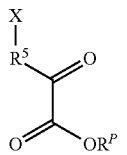

(i-b-2)

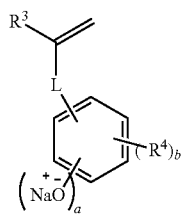

(i-2)

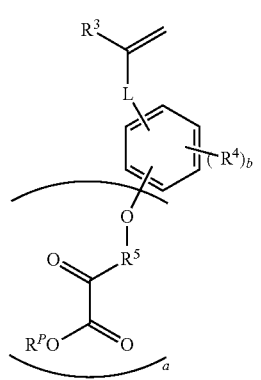

In the formulae (i-a'), (i-b-2) and (i-2), $R^P$ represents a hydrogen atom or a monovalent organic group; X represents a halogen atom; $R^3$ represents a hydrogen atom, or a substituted or unsubstituted alkyl group having 1 to 5 carbon atoms; L represents a single bond, —COO— or —CONR$^N$—, wherein R$^N$ represents a hydrogen atom or a monovalent hydrocarbon group having 1 to 10 carbon atoms; $R^4$ represents an alkyl group having 1 to 5 carbon atoms, an alkoxy group having 1 to 5 carbon atoms or an acyl group having 2 to 5 carbon atoms; $R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof; "a" is an integer of 1 to 5; and "b" is an integer of 0 to 4, wherein a sum of "a" and "b" is no greater than 5, and in a case where $R^P$, $R^4$ and $R^5$ are each present in a plurality of number, a plurality of $R^P$s are each identical or different, a plurality of $R^4$s are each identical or different and a plurality of $R^5$s are each identical or different.

DESCRIPTION OF THE EMBODIMENTS

According to an embodiment of the invention made, a radiation-sensitive resin composition contains: a polymer having a structural unit that includes a group represented by the following formula (1) (hereinafter, may be also referred to as "(A) polymer" or "polymer (A)"); a radiation-sensitive acid generator (hereinafter, may be also referred to as "(B) acid generator" or "acid generator (B)"); and an organic solvent (hereinafter, may be also referred to as "(C) organic solvent" or "organic solvent (C)"),

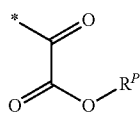
(1)

wherein in the formula (1), $R^P$ represents a hydrogen atom or a monovalent organic group; and * denotes a binding site to a rest of the structural unit other than the group represented by the formula (1).

According to another embodiment of the present invention, a resist pattern-forming method includes: providing a resist film; exposing the resist film; and developing the exposed resist film, wherein the resist film is provided using the radiation-sensitive resin composition according to the above embodiment of the present invention.

According to still another embodiment of the present invention, a polymer has a structural unit that includes a group represented by the following formula (1'):

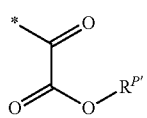
(1')

wherein in the formula (1'), $R^{P'}$ represents a hydrogen atom, or an acid-nonlabile group obtained from a monovalent hydrocarbon group having 2 to 20 carbon atoms by incorporating between adjacent two carbon atoms thereof, at least one selected from the group consisting of —O—, —CO—, —CO—O— and —SO$_2$O—; and * denotes a binding site to a rest of the structural unit other than the group represented by the formula (1').

According to yet another embodiment of the present invention, a polymer has: a structural unit that includes the group represented by the above formula (1); and at least one selected from the group consisting of structural units represented by the formulae (3-1) to (3-4).

According to another embodiment of the present invention, a method for producing a compound represented by the following formula (i-1) includes reacting a compound represented by the following formula (i-a) with a compound represented by the following formula (i-b-1),

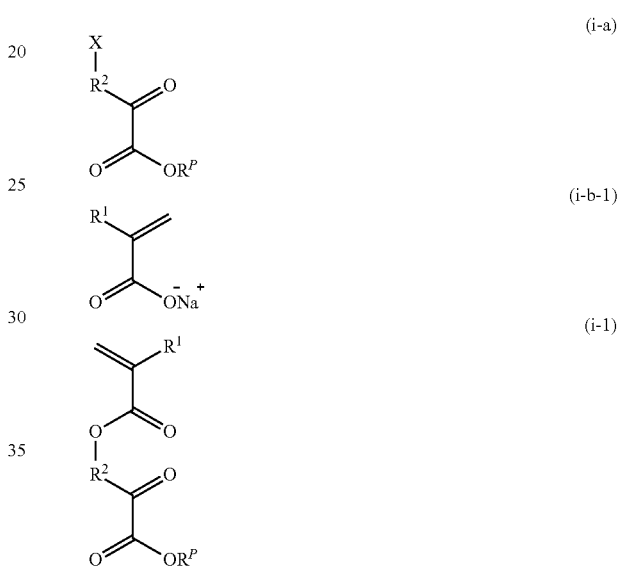

wherein in the formulae (i-a), (i-b-1) and (i-1), $R^P$ represents a hydrogen atom or a monovalent organic group; X represents a halogen atom; $R^1$ represents a hydrogen atom, or a substituted or unsubstituted alkyl group having 1 to 5 carbon atoms; $R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, at least one selected from the group consisting of —CO—, —COO— and —SO$_2$O—.

According to a still other embodiment of the present invention, a method for producing a compound represented by the following formula (i-2) includes reacting a compound represented by the following formula (i-a') with a compound represented by the following formula (i-b-2),

-continued

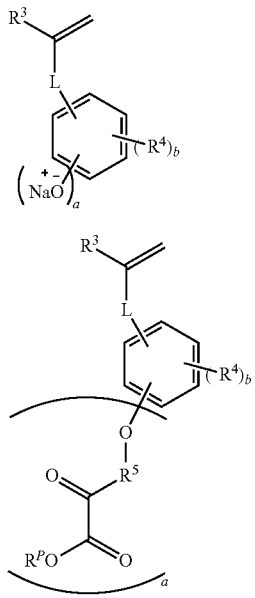

wherein in the formulae (i-a'), (i-b-2) and (i-2), $R^P$ represents a hydrogen atom or a monovalent organic group; X represents a halogen atom; $R^3$ represents a hydrogen atom, or a substituted or unsubstituted alkyl group having 1 to 5 carbon atoms; L represents a single bond, —COO— or —CONR$^N$—, wherein $R^N$ represents a hydrogen atom or a monovalent hydrocarbon group having 1 to 10 carbon atoms; $R^4$ represents an alkyl group having 1 to 5 carbon atoms, an alkoxy group having 1 to 5 carbon atoms or an acyl group having 2 to 5 carbon atoms; $R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, at least one selected from the group consisting of —CO—, —COO— and —SO$_2$O—; "a" is an integer of 1 to 5; and "b" is an integer of 0 to 4, wherein a sum of "a" and "b" is no greater than 5, and in a case where $R^P$, $R^4$ and $R^5$ are each present in a plurality of number, a plurality of $R^P$s may be each identical or different, a plurality of $R^4$s may be each identical or different and a plurality of $R^5$s may be each identical or different.

The "hydrocarbon group" as referred to herein includes chain hydrocarbon groups, alicyclic hydrocarbon groups and aromatic hydrocarbon groups. This "hydrocarbon group" may be a saturated hydrocarbon group or an unsaturated hydrocarbon group. The "chain hydrocarbon group" as referred to means a hydrocarbon group that is constituted with only a chain structure without having a cyclic structure, and the term "chain hydrocarbon group" includes both linear hydrocarbon groups and branched hydrocarbon groups. The "alicyclic hydrocarbon group" as referred to means a hydrocarbon group that has as a ring structure not an aromatic ring structure but only an alicyclic structure, and the term "alicyclic hydrocarbon group" includes both monocyclic alicyclic hydrocarbon groups and polycyclic alicyclic hydrocarbon groups. However, it is not necessary for the alicyclic hydrocarbon group to be constituted with only an alicyclic structure, and a part thereof may have a chain structure. The "aromatic hydrocarbon group" as referred to means a hydrocarbon group that has an aromatic ring structure as a ring structure. However, it is not necessary for the aromatic hydrocarbon group to be constituted with only an aromatic ring structure, and a part thereof may have a chain structure and/or an alicyclic structure.

The radiation-sensitive resin composition and the resist pattern-forming method according to the embodiments of the present invention enable a resist pattern exhibiting a small LWR, a high resolution and superior rectangularity of the cross-sectional shape to be formed while a great depth of focus is exhibited. The polymer according to the embodiments of the present invention can be suitably used as a polymer component of the radiation-sensitive resin composition according to the embodiment of the present invention. The method for producing a compound according to the embodiments of the present invention enables a compound suitable for a basic ingredient of the polymer according to the embodiments of the present invention to be produced conveniently in a favorable yield. Therefore, these can be suitably used for the production of semiconductor devices, in which further progress of miniaturization is expected in the future. Hereinafter, embodiments of the present invention will be described in detail.

Radiation-Sensitive Resin Composition

The radiation-sensitive resin composition according to an embodiment of the present invention contains: (A) a polymer, (B) an acid generator and (C) an organic solvent. The radiation-sensitive resin composition may contain as favorable components, (D) an acid diffusion controller, (E) an acid-labile group-containing polymer other than the polymer (A) (hereinafter, may be also referred to as "(E) polymer" or "polymer (E)"), (F) a fluorine atom-containing polymer (hereinafter, may be also referred to as "(F) polymer" or "polymer (F)"), and may contain other optional component, within a range not leading to impairment of the effects of the present invention. The radiation-sensitive resin composition may contain one, or two or more types of each component. Hereinafter, each component will be explained.

(A) Polymer

The polymer (A) has a structural unit (hereinafter, may be also referred to as "structural unit (I)") that includes a group represented by the following formula (1) (hereinafter, may be also referred to as "group (I)"). Due to the polymer (A) having the structural unit (I), the radiation-sensitive resin composition enables a resist pattern exhibiting a small LWR, a high resolution and superior rectangularity of the cross-sectional shape to be formed while a great depth of focus is exhibited. Although not necessarily clarified, the reason for achieving the effects described above due to the radiation-sensitive resin composition having the aforementioned constitution is presumed, for example, as set forth below. Specifically, the polymer (A) includes the group (—CO—CO—OR$^P$) represented by the following formula (1). This group would be more polar than an ester group (—CO—OR). In addition, in a case where $R^P$ represents an acid-labile group, due to the above-specified structure, the acid-lability of $R^P$ would be greater than that of the ester group, and the acidity of —CO—CO—OH which is generated upon the dissociation would be greater than that of a carboxy group generated from the ester group. Thus, the solubility of the polymer (A) in a developer solution could be properly adjusted, and it would also be expected that a diffusion length of an acid generated from the acid generator (B) would be decreased. It is presumed that consequently, the radiation-sensitive resin composition can achieve an improvement of the LWR performance, the resolution, the rectangularity of the cross-sectional shape, and the depth of focus.

The polymer (A) may have in addition to the structural unit (I): a structural unit (II) represented by the following formula (2); a structural unit (III) which is at least one selected from the group consisting of structural units represented by the following formulae (3-1) to (3-4); a structural unit (IV) that has at least one structure selected from the group consisting of a lactone structure, a cyclic carbonate structure and a sultone structure; and/or a structural unit (V) that includes a hydroxy group, as described later, and may have a structural unit other than those above-specified. The polymer (A) may have one, or two or more types of each of the structural units described above. Hereinafter, each structural unit will be explained.

Structural Unit (I)

The structural unit (I) includes a group represented by the following formula (1).

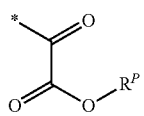

(1)

In the above formula (1), $R^P$ represents a hydrogen atom or a monovalent organic group; and * denotes a binding site to a rest of the structural unit (I) other than the group represented by the formula (1).

The monovalent organic group represented by $R^P$ is not particularly limited, and may be, for example, an acid-nonlabile group, or an acid-labile group. The "acid-labile group" as referred to means a group that substitutes for the hydrogen atom of an —OH group and is dissociated by an action of an acid. When $R^P$ represents an acid-nonlabile group, the structural unit (I) can be used to adjust more properly the solubility of the polymer (A) upon the dissociation of the acid-labile group included in the polymer (A). Alternatively, when $R^P$ represents an acid-labile group, the polymer (A) is an acid-labile group-containing polymer, and thus the solubility of the polymer (A) upon the dissociation of the acid-labile group of the structural unit (I) can be adjusted more properly. In either case, the solubility of the polymer (A) in a developer solution can be adjusted more properly. Moreover, it is expected that a diffusion length of an acid generated from the acid generator (B) would be decreased. As a result, the radiation-sensitive resin composition can achieve superior LWR performance, solubility, rectangularity of the cross-sectional shape, and depth of focus.

The acid-nonlabile group is exemplified by: (1) a group obtained by substituting a part or all of hydrogen atoms included in a monovalent hydrocarbon group having 1 to 20 carbon atoms with a polar group (hereinafter, may be also referred to as "group (1)"); (2) a group obtained from a monovalent hydrocarbon group having 2 to 20 carbon atoms by incorporating between adjacent two carbon atoms thereof, at least one selected from the group consisting of —O—, —CO—, —COO— and —SO$_2$O— (hereinafter, may be also referred to as "group (2)"); or (3) a group obtained from a monovalent hydrocarbon group having 2 to 20 carbon atoms by incorporating between adjacent two carbon atoms thereof, at least one selected from the group consisting of —O—, —CO—, —COO— and —SO$_2$O— and substituting a part or all of hydrogen atoms thereof with a polar group (hereinafter, may be also referred to as "group (3)"); and the like.

The monovalent hydrocarbon group having 1 to 20 carbon atoms is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include:
alkyl groups such as a methyl group, an ethyl group, a propyl group, a butyl group and a pentyl group;
alkenyl groups such as an ethenyl group, a propenyl group, a butenyl group and a pentenyl group;
alkynyl groups such as an ethynyl group, a propynyl group, a butynyl group and a pentynyl group; and the like.

Examples of the monovalent alicyclic hydrocarbon group having 3 to 20 carbon atoms include:
monocyclic cycloalkyl groups such as a cyclopropyl group, a cyclobutyl group, a cyclopentyl group and a cyclohexyl group;
polycyclic cycloalkyl groups such as a norbornyl group, an adamantyl group, a tricyclodecyl group and a tetracyclododecyl group;
monocyclic cycloalkenyl groups such as a cyclobutenyl group, a cyclopentenyl group and a cyclohexenyl group;
polycyclic cycloalkenyl groups such as a norbornenyl group and a tricyclodecenyl group; and the like.

Examples of the monovalent aromatic hydrocarbon group having 6 to 20 carbon atoms include:
aryl groups such as a phenyl group, a tolyl group, a xylyl group, a mesityl group, a naphthyl group and an anthryl group;
aralkyl groups such as a benzyl group, a phenethyl group, a naphthylmethyl group and an anthrylmethyl group; and the like.

Examples of the polar group include a hydroxy group, a carboxy group, a cyano group, an amino group, and the like. Of these, a hydroxy group, a carboxy group and a cyano group are preferred, and a hydroxy group and a cyano group are more preferred.

Examples of the group (1) include: polar group-substituted alkyl groups such as a hydroxymethyl group and a cyanoethyl group; polar group-substituted cycloalkyl groups such as a carboxycyclohexyl group, a hydroxyadamantyl group and a dihydroxyadamantyl group; polar group-substituted aryl groups such as an aminophenyl group and a hydroxyphenyl group; and the like. Of these, polar group-substituted cycloalkyl groups are preferred, and a hydroxyadamantyl group and a dihydroxyadamantyl group are more preferred.

Examples of the group (2) include: groups that have a cyclic ether structure, such as an oxycyclopentyl group and an oxycyclohexyl group; groups that have a cyclic ketone structure, such as an oxocyclopentyl group, an oxocyclohexyl group and an oxoadamantyl group; groups that have a lactone structure, such as a butyrolacton-yl group, a norbornanelacton-yl group and an oxynorbornanelacton-yl group; groups that have a sultone structure, such as a propiosulton-yl group and a norbornanesulton-yl group; and the like. Of these, groups that have a cyclic ketone structure, groups that have a lactone group and groups that have a sultone structure are preferred, and an oxyadamantyl group, a butyrolacton-yl group, a norbornanelacton-yl group, an oxynorbornanelacton-yl group and a norbornanesulton-yl group are more preferred.

Examples of the group (3) include: groups that have a polar group-substituted cyclic ether structure, such as a hydroxytetrahydropyran-yl group; groups that have a polar group-substituted cyclic ketone structure such as a cyanocyclohexanon-yl group; groups that have a polar group-substituted lactone structure, such as a cyanobutyrolacton-yl group and a cyanonorbornanelacton-yl group; groups that have a polar group-substituted sultone structure such as a cyanonorbornanesulton-yl group; and the like. Of these, groups that include a polar group-substituted lactone structure are preferred, and a cyanonorbornanelacton-yl group is more preferred.

In light of ease in synthesis of a monomer that includes the group (I), among the groups (1) to (3), the groups (1) and (2) are preferred, and the group (2) is more preferred.

The acid-labile group is exemplified by, but not particularly limited to, a group represented by the following formula (p), and the like.

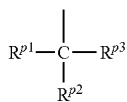

(p)

In the above formula (p), $R^{p1}$ represents a hydrogen atom or a monovalent chain hydrocarbon group having 1 to 10 carbon atoms; $R^{p2}$ and $R^{p3}$ each independently represent a monovalent chain hydrocarbon group having 1 to 10 carbon atoms or a monovalent alicyclic hydrocarbon group having 3 to 20 carbon atoms, or taken together represent a ring structure having 3 to 20 ring atoms, together with the carbon atom to which $R^{p2}$ and $R^{p3}$ bond.

Examples of the monovalent chain hydrocarbon group having 1 to 10 carbon atoms which may be represented by $R^{p1}$, $R^{p2}$ or $R^{p3}$ include monovalent chain hydrocarbon groups having 1 to 10 carbon atoms among the groups exemplified in connection with the monovalent chain hydrocarbon group of the group (1), and the like.

Examples of the monovalent alicyclic hydrocarbon group having 3 to 20 carbon atoms which may be represented by $R^{p2}$ or $R^{p3}$ include groups identical to those exemplified in connection with the monovalent alicyclic hydrocarbon group of the group (1), and the like.

Examples of the ring structure having 3 to 20 ring atoms which may be taken together represented by $R^{p2}$ and $R^{p3}$, together with the carbon atom to which $R^{p2}$ and $R^{p3}$ bond include: cycloalkane structures such as a cyclopropane structure, a cyclobutane structure, a cyclopentane structure, a cyclohexane structure, a cycloheptane structure, a cyclooctane structure, a cyclononane structure, a cyclodecane structure, a norbornane structure and an adamantane structure; cycloalkene structures such as a cyclobutene structure, a cyclopentene structure, a cyclohexene structure, a cycloheptene structure, a cyclooctene structure, a cyclodecene structure and a norbornene structure; and the like.

The acid-labile group is exemplified by: an alkyl group having an atomic bonding on a tertiary carbon atom; a cycloalkyl-substituted alkyl group having an atomic bonding on a tertiary carbon atom; a 1-alkyl-substituted 1-cycloalkyl group; a cycloalkenyl group having an atomic bonding on a secondary carbon atom in an allyl position; and the like.

$R^P$ preferably represents a monovalent organic group.

Examples of the structural unit (I) include structural units represented by the following formulae (1-1) and (1-2) (hereinafter, may be also referred to as "structural unit (I-1)" and "structural unit (I-2)", respectively), and the like.

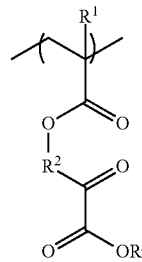

(1-1)

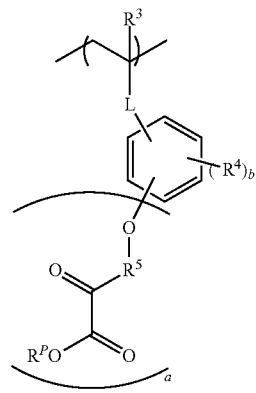

(1-2)

In the above formulae (1-1) and (1-2), $R^P$ is as defined in the above formula (1).

In the above formula (1-1), $R^1$ represents a hydrogen atom, or a substituted or unsubstituted alkyl group having 1 to 5 carbon atoms; $R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, at least one selected from the group consisting of —CO—, —COO— and —SO$_2$O—.

In the above formula (1-2), $R^3$ represents a hydrogen atom, or a substituted or unsubstituted alkyl group having 1 to 5 carbon atoms; L represents a single bond, —COO— or —CONR$^N$—, wherein R$^N$ represents a hydrogen atom or a monovalent hydrocarbon group having 1 to 10 carbon atoms; $R^4$ represents an alkyl group having 1 to 5 carbon atoms, an alkoxy group having 1 to 5 carbon atoms or an acyl group having 2 to 5 carbon atoms; $R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, at least one selected from the group consisting of —CO—, —COO— and —SO$_2$O—; "a" is an integer of 1 to 5; and "b" is an integer of 0 to 4, wherein a sum of "a" and "b" is no greater than 5, and in a case where $R^P$, $R^4$ and $R^5$ are each present in a plurality of number, a plurality of $R^P$s may be each identical or different, a plurality of $R^4$s may be each identical or different and a plurality of $R^5$s may be each identical or different.

Examples of the alkyl group having 1 to 5 carbon atoms which may be represented by $R^1$ or $R^3$ include a methyl group, an ethyl group, a n-propyl group, an i-propyl group, a n-butyl group, an i-butyl group, a sec-butyl group, a t-butyl group, a n-pentyl group, and the like.

Examples of the substituent which may be present in the alkyl group which may be represented by $R^1$ or $R^3$ include: halogen atoms such as a fluorine atom, a chlorine atom, a bromine atom and an iodine atom; a hydroxy group; a carboxy group; a cyano group; an amino group; and the like.

$R^1$ and $R^3$ are exemplified by a hydrogen atom, a methyl group, a trifluoromethyl group, and the like.

The monovalent hydrocarbon group having 1 to 10 carbon atoms which may be represented by $R^N$ in —$CONR^N$— as L is exemplified by an alkyl group having 1 to 10 carbon atoms, a cycloalkyl group having 3 to 20 carbon atoms, an aryl group having 6 to 20 carbon atoms, and the like.

L represents preferably a single bond or —COO—, and more preferably a single bond.

Examples of the alkyl group having 1 to 5 carbon atoms which may be represented by $R^4$ include groups identical to those exemplified in connection with the alkyl group having 1 to 5 carbon atoms which may be represented by $R^1$, and the like.

Examples of the alkoxy group having 1 to 5 carbon atoms which may be represented by $R^4$ include a methoxy group, an ethoxy group, a n-propoxy group, an i-propoxy group, a n-butoxy group, an i-butoxy group, a sec-butoxy group, a t-butoxy group, a n-pentyloxy group, and the like.

Examples of the acyl group having 2 to 5 carbon atoms which may be represented by $R^4$ include saturated acyl groups such as an acetyl group, a propionyl group, a butyryl group, an isobutyryl group, a valeryl group, an isovaleryl group and a pivaloyl group; unsaturated acyl groups such as an acryloyl group, a propioloyl group, a methacryloyl group, a crotonoyl group and an isocrotonoyl group; and the like.

Examples of the alkylene group having 2 to 10 carbon atoms which may be represented by $R^2$ or $R^5$ include an ethylene group, a propylene group, a butylene group, a pentylene group, a hexylene group, an octylene group, a decylene group, and the like.

Examples of the cycloalkylene group having 3 to 20 carbon atoms which may be represented by $R^2$ or $R^5$ include a cyclopropylene group, a cyclobutylene group, a cyclopentylene group, a cyclohexylene group, a cyclooctylene group, a cyclodecylene group, a norbornylene group, an adamantylene group, and the like.

Examples of the arylene group having 6 to 20 carbon atoms which may be represented by $R^2$ or $R^5$ include a phenylene group, a tolylene group, a xylylene group, a mesitylene group, a naphthylene group, an anthrylene group, and the like.

Examples of the group obtained from an alkylene group having 2 to 10 carbon atoms or a cycloalkylene group having 3 to 20 carbon atoms by incorporating between adjacent two carbon atoms thereof, —CO—, —COO— or —$SO_2O$—, which may be represented by $R^2$ or $R^5$, include a (cyclo)alkylenecarbonyl(cyclo)alkylene group, a (cyclo)alkylenecarbonyloxy(cyclo)alkylene group, a (cyclo)alkylenesulfonyloxy(cyclo)alkylene group, and the like.

$R^2$ and $R^5$ represent preferably a methylene group or an alkylene group having 2 to 5 carbon atoms, and more preferably a methylene group.

Preferably "a" is 1 or 2, and more preferably 1.

Preferably "b" is 0 or 1, and more preferably 0.

Examples of the structural unit (I) include structural units represented by the following formulae (1-1-1) to (1-2-16) (hereinafter, may be also referred to as "structural units (I-1-1) to (I-2-16)"), and the like.

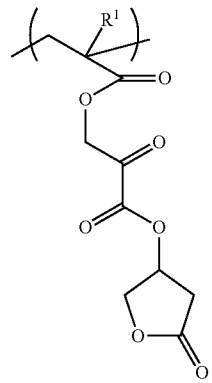

(1-1-1)

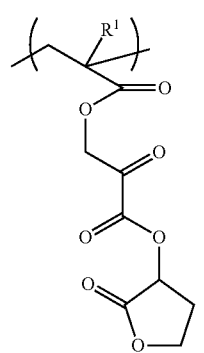

(1-1-2)

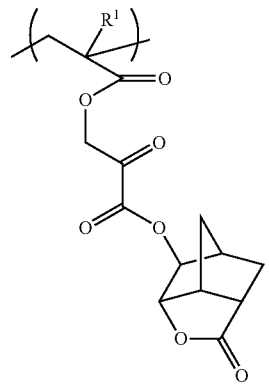

(1-1-3)

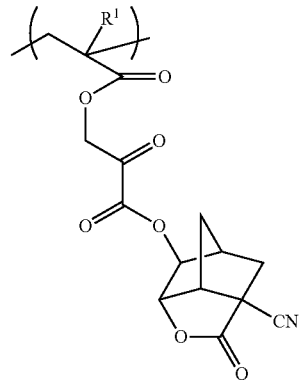

(1-1-4)

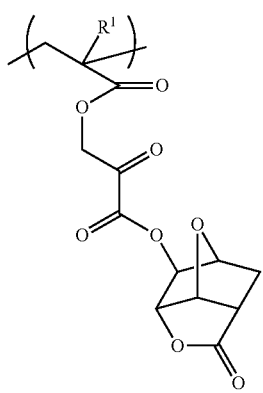
(1-1-5)
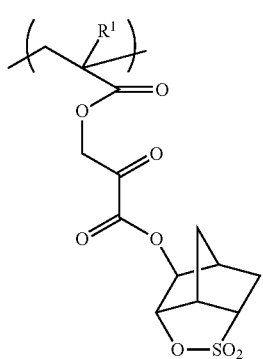
(1-1-6)
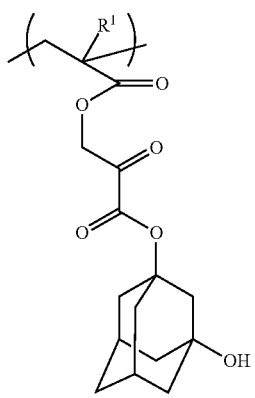
(1-1-7)
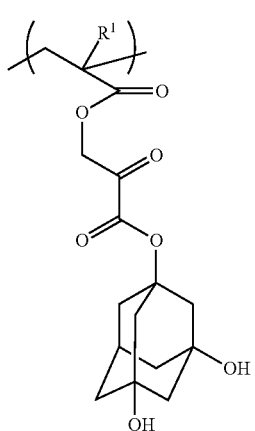
(1-1-8)
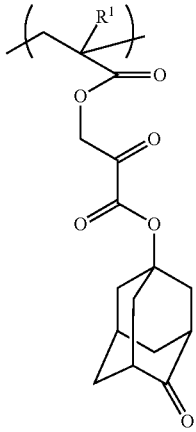
(1-1-9)
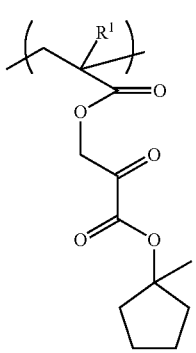
(1-1-10)
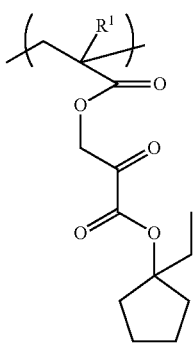
(1-1-11)
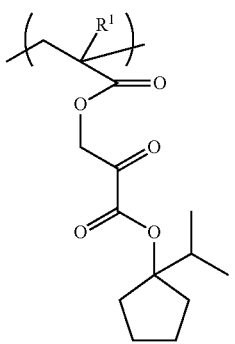
(1-1-12)

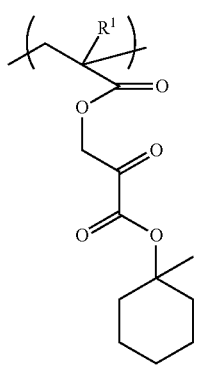 (1-1-13)
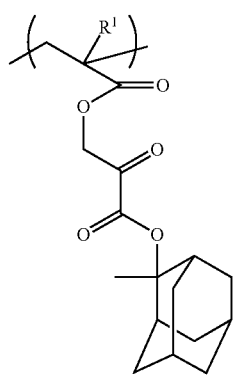 (1-1-17)
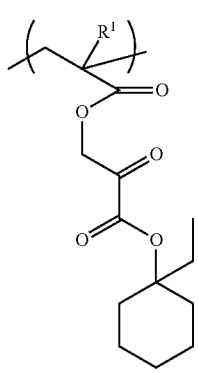 (1-1-14)
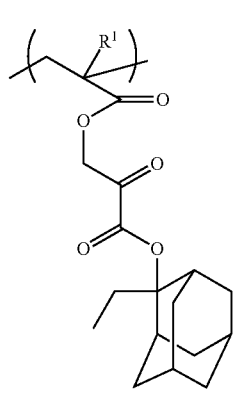 (1-1-18)
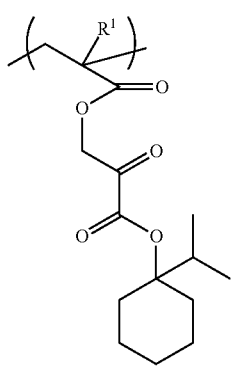 (1-1-15)
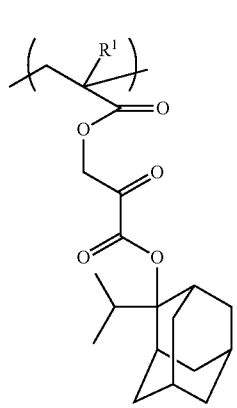 (1-1-19)
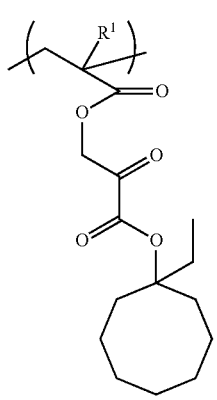 (1-1-16)
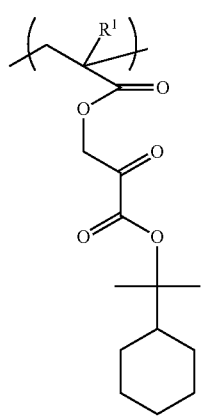 (1-1-20)

-continued
(1-1-21) 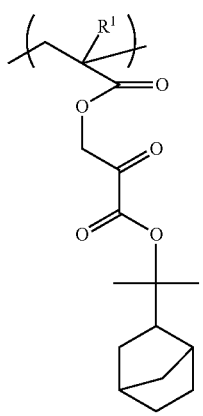
(1-1-22) 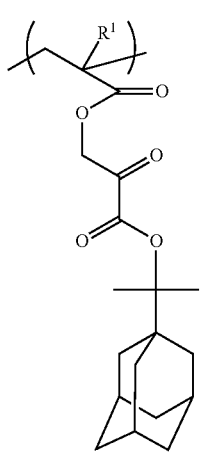
(1-1-23) 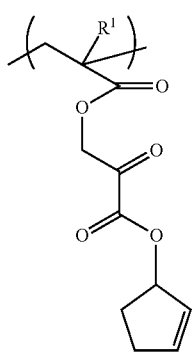
(1-1-24) 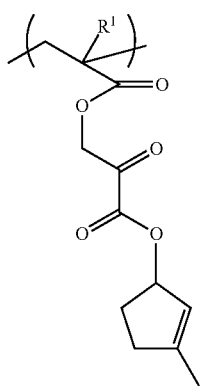
(1-1-25) 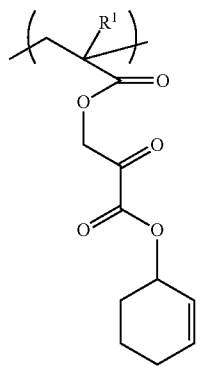
(1-1-26) 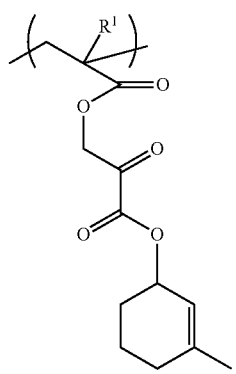
(1-1-27) 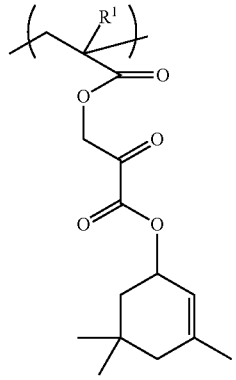
(1-1-28) 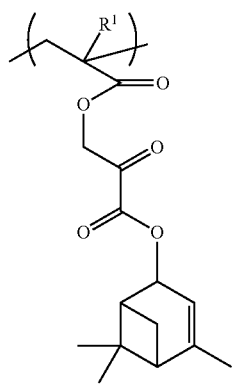

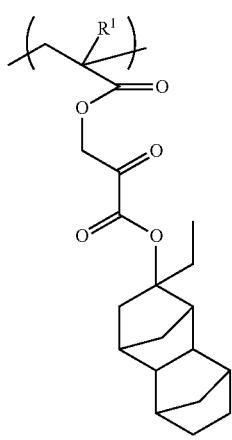
(1-1-29)
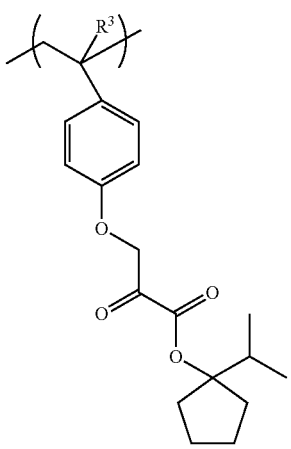
(1-2-3)
In the above formulae (1-1-1) to (1-1-29), $R^1$ is as defined in the above formula (1-1).
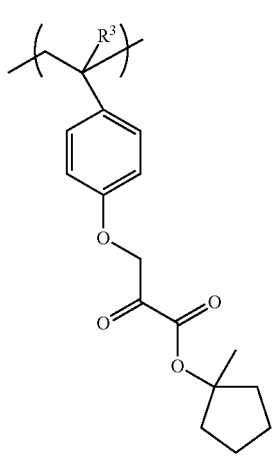
(1-2-1)
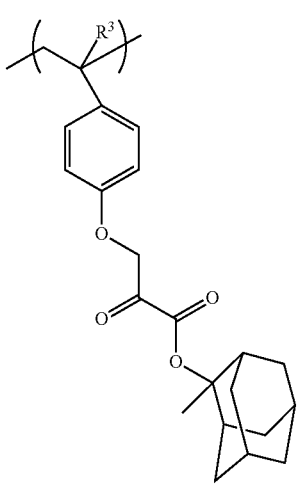
(1-2-4)
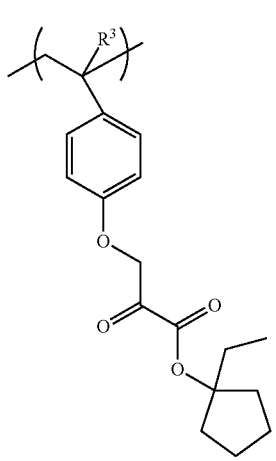
(1-2-2)
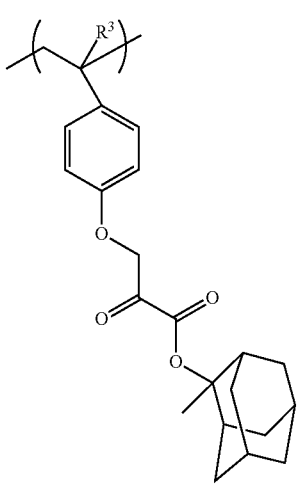
(1-2-5)

-continued
(1-2-6)
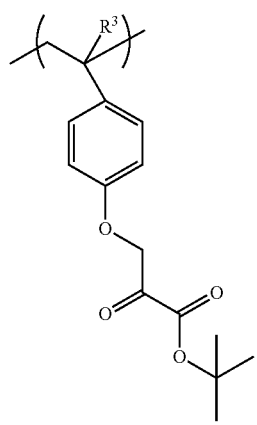
(1-2-7)
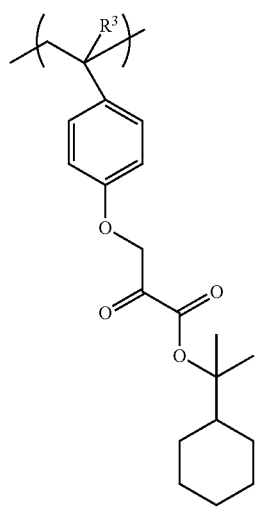
(1-2-8)
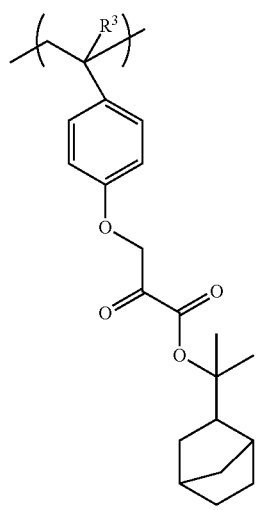
(1-2-9)
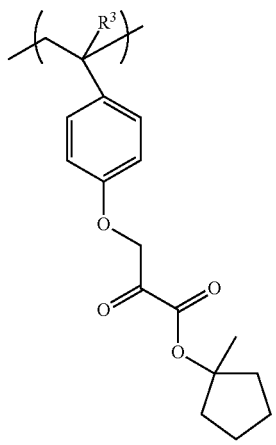
(1-2-10)
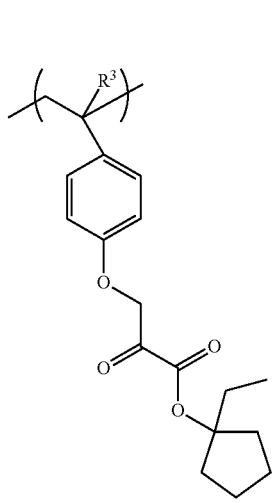
(1-2-11)
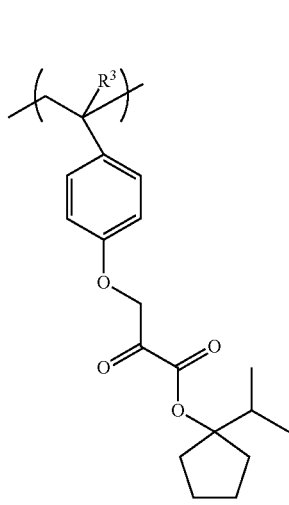

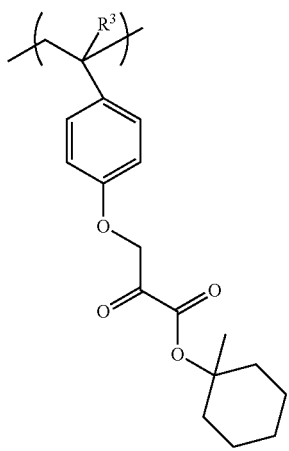
(1-2-12)

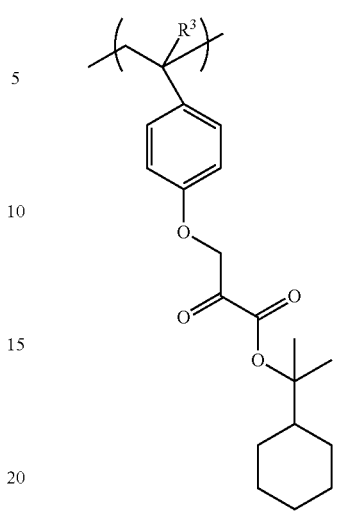
(1-2-15)

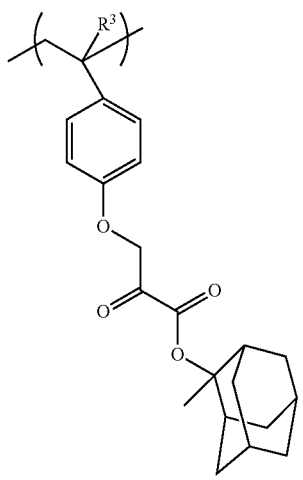
(1-2-13)

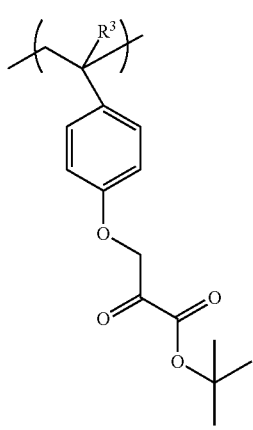
(1-2-14)

(1-2-16)

In the above formulae (1-2-1) to (1-2-16), $R^3$ is as defined in the above formula (1-2).

The lower limit of the proportion of the structural unit (I) with respect to the total structural units constituting the polymer (A) is preferably 10 mol %, more preferably 20 mol %, and still more preferably 30 mol %. The upper limit of the proportion of the structural unit (I) is preferably 90 mol %, more preferably 70 mol %, and still more preferably 50 mol %. When the proportion of the structural unit (I) falls within the above range, the radiation-sensitive resin composition can achieve an improvement of the LWR performance, the resolution, the rectangularity of the cross-sectional shape, and the depth of focus.

A monomer that gives the structural unit (I) (hereinafter, may be also referred to as "compound (i)") is exemplified by compounds represented by the following formulae (i-1-1) to (i-2-16) (hereinafter, may be also referred to as "compounds (i-1-1) to (i-2-16)"), and the like.

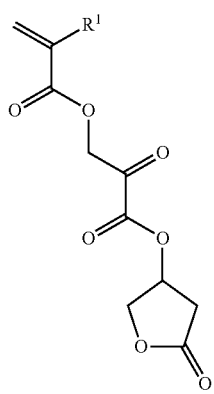 (i-1-1)
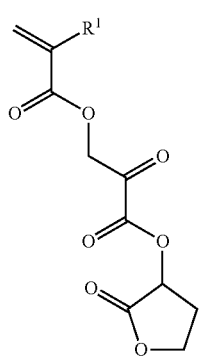 (i-1-2)
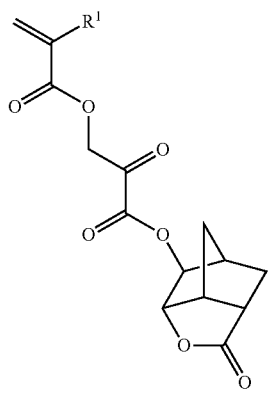 (i-1-3)
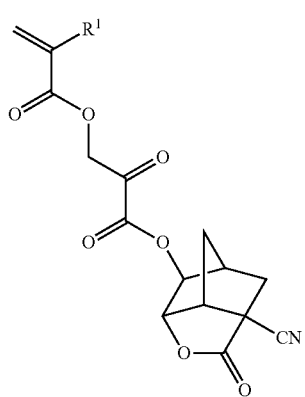 (i-1-4)
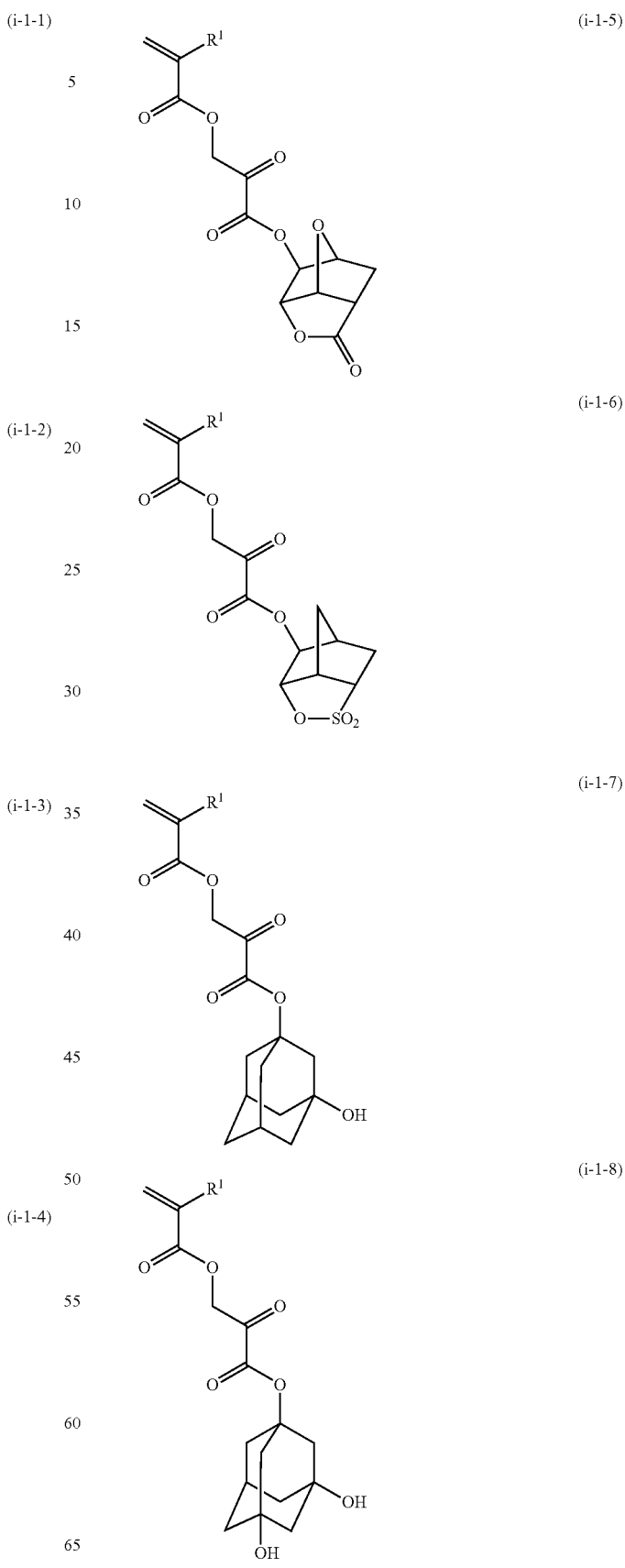

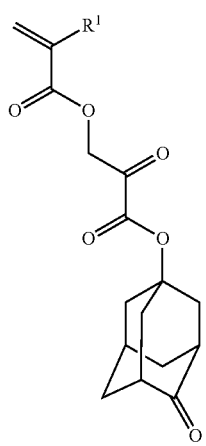 (i-1-9)
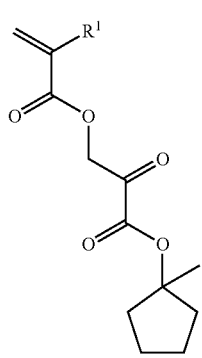 (i-1-10)
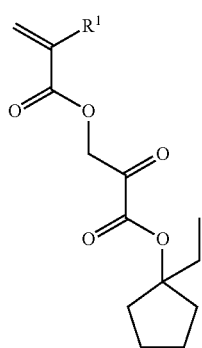 (i-1-11)
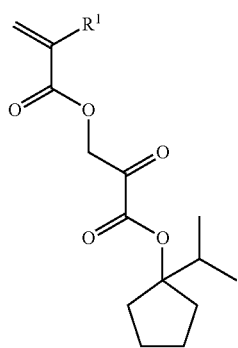 (i-1-12)
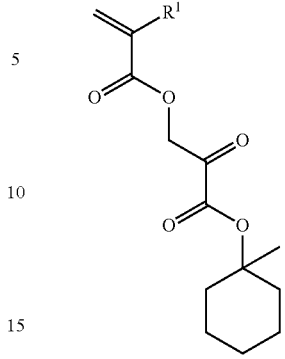 (i-1-13)
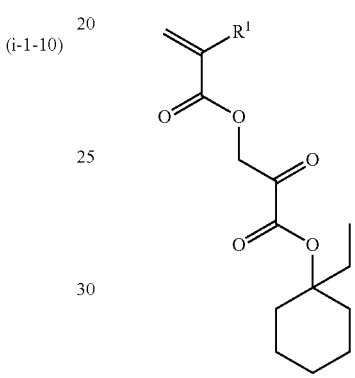 (i-1-14)
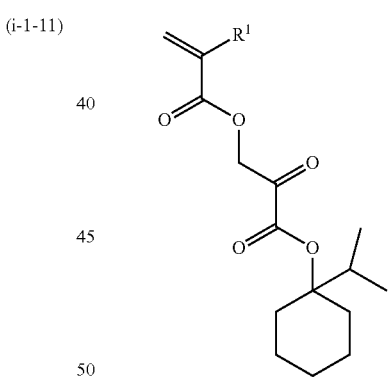 (i-1-15)
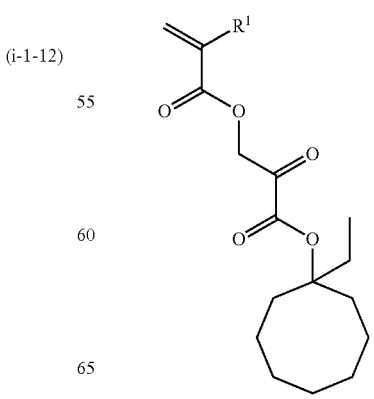 (i-1-16)

(i-1-17)
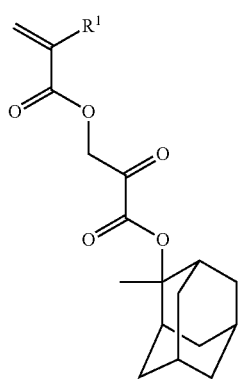
(i-1-18)
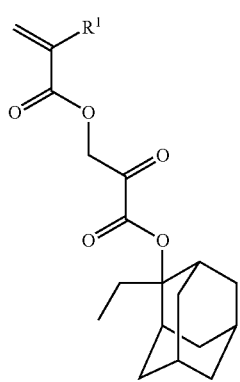
(i-1-19)
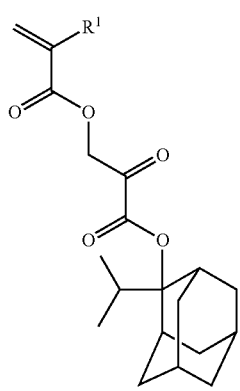
(i-1-20)
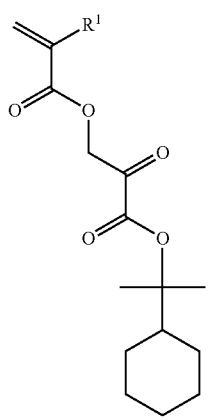
(i-1-21)
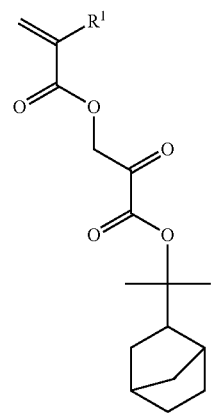
(i-1-22)
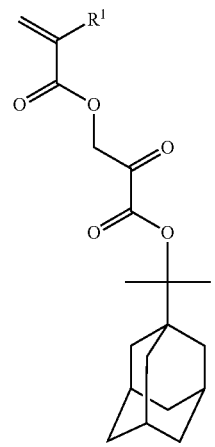
(i-1-23)
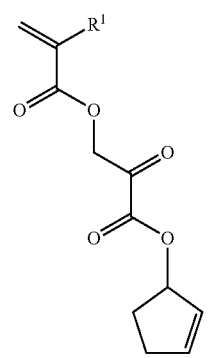
(i-1-24)
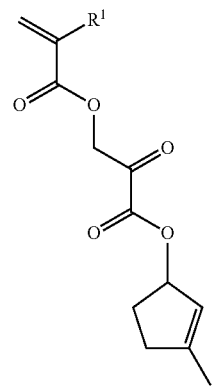

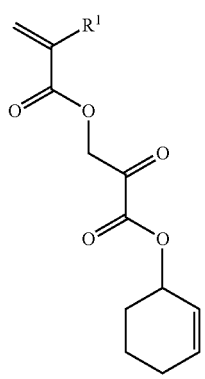
(i-1-25)
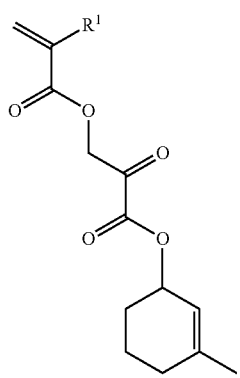
(i-1-26)
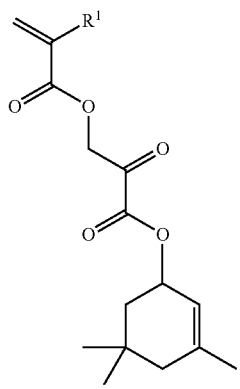
(i-1-27)
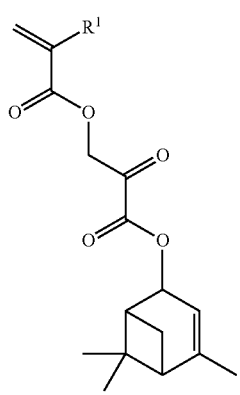
(i-1-28)
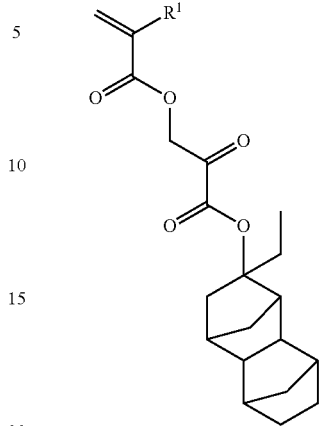
(i-1-29)
In the above formulae (i-1-1) to (i-1-29), $R^1$ is as defined in the above formula (1-1).
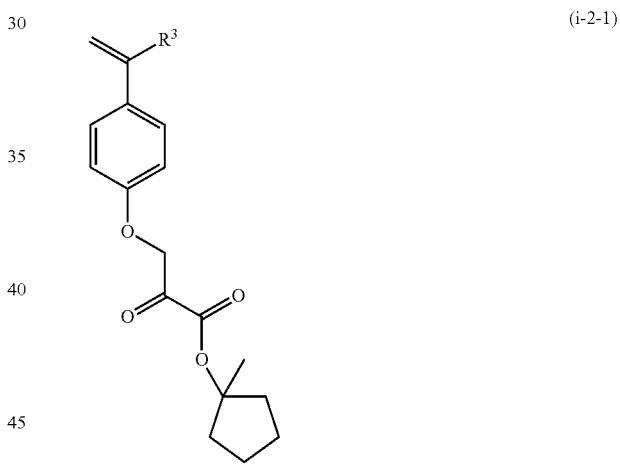
(i-2-1)
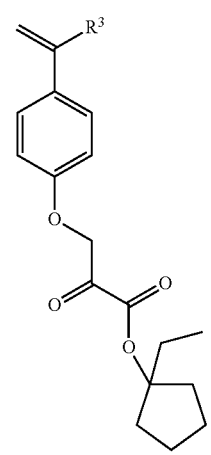
(i-2-2)

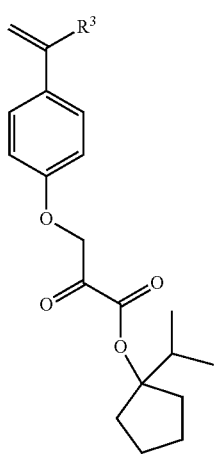
(i-2-3)
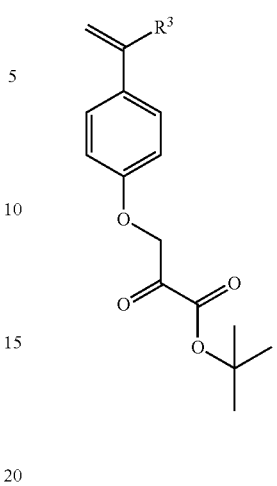
(i-2-6)
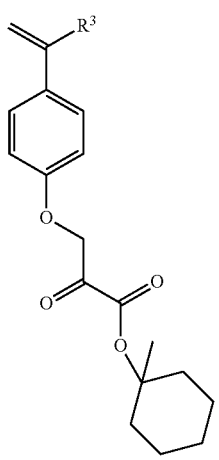
(i-2-4)
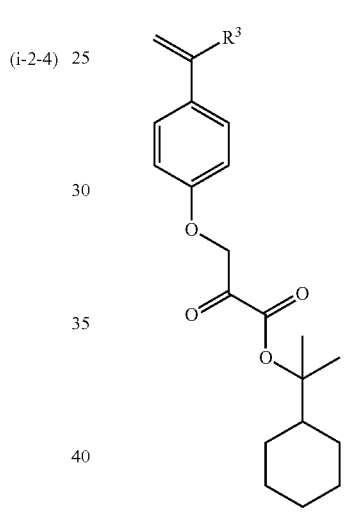
(i-2-7)
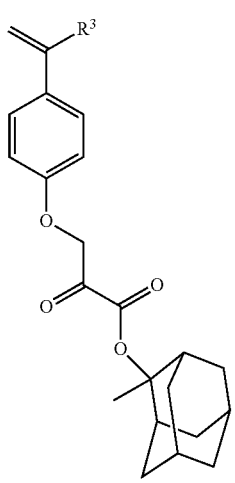
(i-2-5)
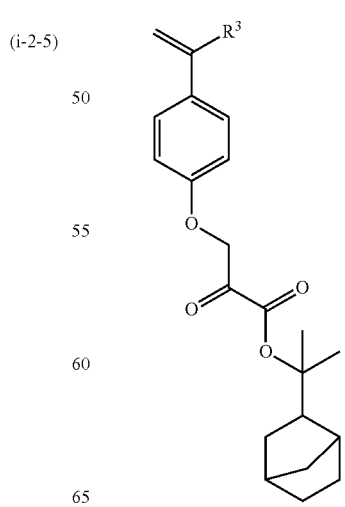
(i-2-8)

(i-2-9)
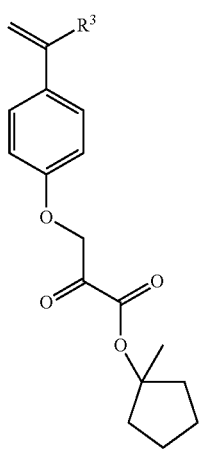
(i-2-10)
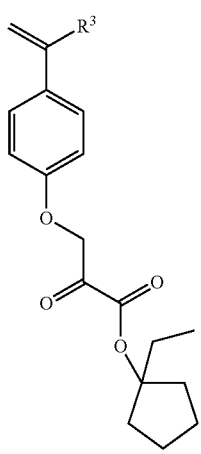
(i-2-11)
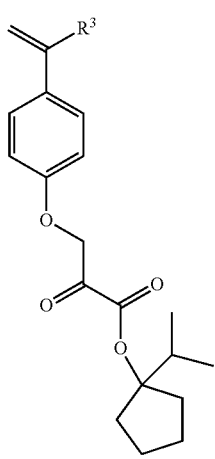
(i-2-12)
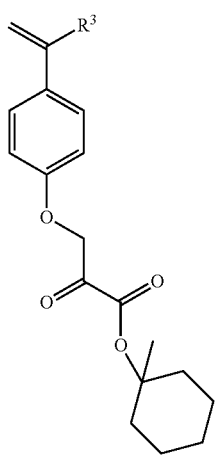
(i-2-13)
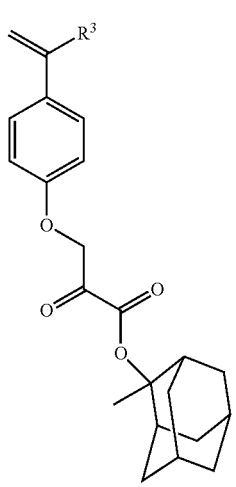
(i-2-14)
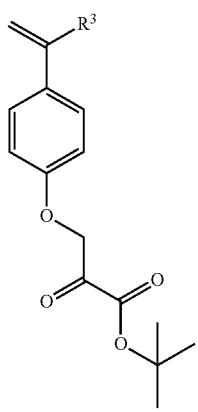

-continued

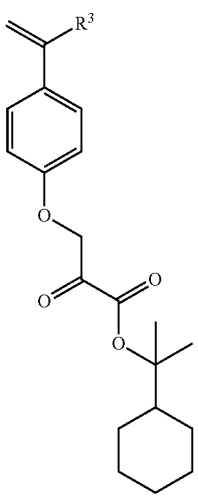
(i-2-15)

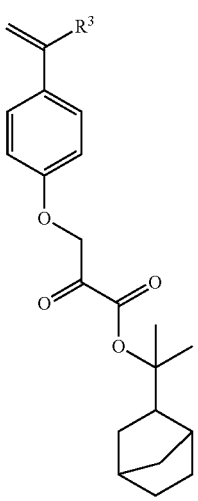
(i-2-16)

In the above formulae (i-2-1) to (i-2-16), $R^3$ is as defined in the above formula (1-2).

The production method of the compound (i) is exemplified by the followings:

in a case where the compound (i) is a compound represented by the following formula (i-1) (hereinafter, may be also referred to as "compound (i-1)"), a method is exemplified which includes the step of reacting a compound represented by the following formula (i-a) (hereinafter, may be also referred to as "compound (i-a)") with a compound represented by the following formula (i-b-1) (hereinafter, may be also referred to as "compound (i-b-1)"); and in a case where the compound (i) is a compound represented by the following formula (i-2) (hereinafter, may be also referred to as "compound (i-2)"), a method is exemplified which includes the step of reacting a compound represented by the following formula (i-a') (hereinafter, may be also referred to as "compound (i-a')") with a compound represented by the following formula (i-b-2) (hereinafter, may be also referred to as "compound (i-b-2)").

According to the aforementioned production method, the compound (i) can be produced conveniently in a favorable yield.

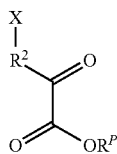
(i-a)

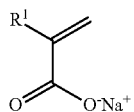
(i-b-1)

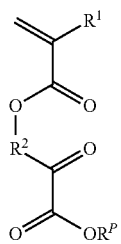
(i-1)

In the above formulae (i-a), (i-b-1) and (i-1), $R^P$ represents a hydrogen atom or a monovalent organic group; X represents a halogen atom; $R^1$ represents a hydrogen atom, or a substituted or unsubstituted alkyl group having 1 to 5 carbon atoms; and $R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or an cycloalkylene group having 3 to 20 carbon atoms by incorporating between adjacent two carbon atoms of, at least one selected from the group consisting of —CO—, —COO— and —$SO_2$O—.

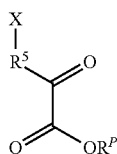
(i-a')

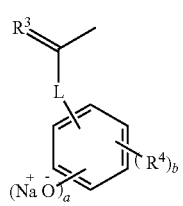
(i-b-2)

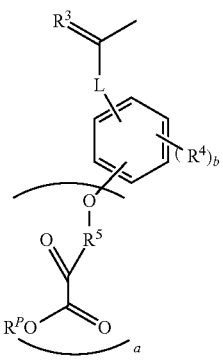

(i-2)

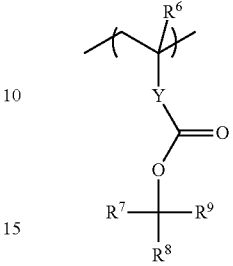

(2)

In the above formulae (i-a'), (i-b-2) and (i-2), $R^P$ represents a hydrogen atom or a monovalent organic group; X represents a halogen atom; $R^3$ represents a hydrogen atom, or a substituted or unsubstituted alkyl group having 1 to 5 carbon atoms; L represents a single bond, —COO— or —CONR$^N$—, wherein $R^N$ represents a hydrogen atom or a monovalent hydrocarbon group having 1 to 10 carbon atoms; $R^4$ represents an alkyl group having 1 to 5 carbon atoms, an alkoxy group having 1 to 5 carbon atoms or an acyl group having 2 to 5 carbon atoms; $R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms of, at least one selected from the group consisting of —CO—, —COO— and —SO$_2$O—; "a" is an integer of 1 to 5; and "b" is an integer of 0 to 4, wherein a sum of "a" and "b" is no greater than 5, and in a case where $R^P$, $R^4$ and $R^5$ are each present in a plurality of number, a plurality of $R^P$s may be each identical or different, a plurality of $R^4$s may be each identical or different and a plurality of $R^5$s may be each identical or different.

Examples of the halogen atom represented by X include a fluorine atom, a chlorine atom, a bromine atom, an iodine atom, and the like. Of these, in light of more proper reactivity of the compounds (i-a) and (i-a'), a chlorine atom and a bromine atom are preferred, and a bromine atom is more preferred.

The compound (i-a) is reacted with the compound (i-b-1) in a solvent such as a mixed solvent composed of tetrahydrofuran and water to obtain the compound (i-1). Alternatively, the compound (i-a') is similarly reacted with the compound (i-b-2) to obtain the compound (i-2).

The aforementioned compounds (i-a) and (i-a') can be obtained by reacting a halogenated compound that includes a —COCOOH group, such as 3-halopyruvic acid, with an alcohol compound that includes the $R^P$ group described in connection with the above formula (1), in the presence of a base such as dimethylaminopyridine, and a dehydrating agent such as 1-ethyl-3-[3-(dimethylamino)propyl]carbodiimide hydrochloride (EDCI).

Structural Unit (II)

The structural unit (II) is represented by the following formula (2). The group represented by —CR$^7$R$^8$R$^9$ in the structural unit (II) is an acid-labile group. Due to the polymer (A) having the structural unit (II), the radiation-sensitive resin composition has increased sensitivity, and consequently can improve the LWR performance, the resolution, the rectangularity of the cross-sectional shape, and the depth of focus.

In the above formula (2), $R^6$ represents a hydrogen atom, a fluorine atom, a methyl group or a trifluoromethyl group; Y represents a single bond, a carbonyloxycycloalkanediyl group having 4 to 20 carbon atoms, a carbonyloxycycloalkanediyloxy group having 4 to 20 carbon atoms, an arenediyl group having 6 to 20 carbon atoms, or a carbonyloxyarenediyl group having 7 to 20 carbon atoms; $R^7$ represents a monovalent chain hydrocarbon group having 1 to 10 carbon atoms or a monovalent alicyclic hydrocarbon group having 3 to 20 carbon atoms; and $R^8$ and $R^9$ each independently represent a monovalent chain hydrocarbon group having 1 to 10 carbon atoms or a monovalent alicyclic hydrocarbon group having 3 to 20 carbon atoms, or taken together represent an alicyclic structure having 3 to 20 carbon atoms, together with the carbon atom to which $R^8$ and $R^9$ bond.

Examples of the carbonyloxycycloalkanediyl group having 4 to 20 carbon atoms which may be represented by Y include:

monocyclic carbonyloxycycloalkanediyl groups such as a carbonyloxycyclopropanediyl group, a carbonyloxycyclobutanediyl group, a carbonyloxycyclopentanediyl group and a carbonyloxycyclohexanediyl group;

polycyclic carbonyloxycycloalkanediyl groups such as a carbonyloxynorbornanediyl group, a carbonyloxyadamantanediyl group, a carbonyloxytricyclodecanediyl group and a carbonyloxytetracyclododecanediyl group; and the like.

Examples of the carbonyloxycycloalkanediyloxy group having 4 to 20 carbon atoms which may be represented by Y include:

monocyclic carbonyloxycycloalkanediyloxy groups such as a carbonyloxycyclopropanediyloxy group, a carbonyloxycyclobutanediyloxy group, a carbonyloxycyclopentanediyloxy group and a carbonyloxycyclohexanediyloxy group;

polycyclic carbonyloxycycloalkanediyloxy groups such as a carbonyloxynorbornanediyloxy group, a carbonyloxyadamantanediyloxy group, a carbonyloxytricyclodecanediyloxy group and a carbonyloxytetracyclododecanediyloxy group; and the like.

Examples of the arenediyl group having 6 to 20 carbon atoms which may be represented by Y include a benzenediyl group, a toluenediyl group, a xylenediyl group, a mesitylenediyl group, a naphthalenediyl group, an anthracenediyl group, and the like.

Examples of the carbonyloxyarenediyl group having 7 to 20 carbon atoms which may be represented by Y include a carbonyloxybenzenediyl group, a carbonyloxytoluenediyl group, a carbonyloxyxylenediyl group, a carbonyloxymesityleneoxy group, a carbonyloxynaphthalenediyl group, a carbonyloxyanthracenediyl group, and the like.

Y represents preferably a single bond, a carbonyloxycycloalkanediyloxy group having 4 to 20 carbon atoms or an arenediyl group having 6 to 20 carbon atoms, more preferably a single bond, a polycyclic carbonyloxycycloalkanediyloxy group or a benzenediyl group, and still more preferably a single bond or a benzenediyl group.

In light of copolymerizability of a monomer that gives the structural unit (II), $R^6$ represents preferably a hydrogen atom or a methyl group, and more preferably a methyl group.

Examples of the monovalent chain hydrocarbon group having 1 to 10 carbon atoms which may be represented by $R^7$, $R^8$ or $R^9$ include:

alkyl groups such as a methyl group, an ethyl group, a n-propyl group and an i-propyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 20 carbon atoms which may be represented by $R^7$, $R^8$ or $R^9$ include:

monocyclic cycloalkyl groups such as a cyclopentyl group and a cyclohexyl group;

monocyclic cycloalkenyl groups such as a cyclopentenyl group and a cyclohexenyl group;

polycyclic cycloalkyl groups such as a norbornyl group, an adamantyl group and a tricyclodecyl group;

polycyclic cycloalkenyl groups such as a norbornenyl group and a tricyclodecenyl group; and the like.

Examples of the alicyclic structure having 3 to 20 carbon atoms which may be taken together represented by $R^8$ and $R^9$, together with the carbon atom to which $R^8$ and $R^9$ bond include:

monocyclic cycloalkane structures such as a cyclopropane structure, a cyclobutane structure, a cyclopentane structure, a cyclohexane structure, a cycloheptane structure and a cyclooctane structure;

polycyclic cycloalkane structures such as a norbornane structure, an adamantane structure, a tricyclodecane structure and a tetracyclododecane structure; and the like.

As the structural unit (II), structural units represented by the following formulae (2-1) to (2-7) (hereinafter, may be also referred to as "structural units (II-1) to (II-7)") are preferred.

(2-1)

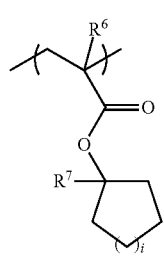

(2-2)

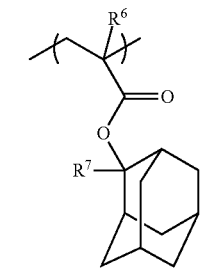

(2-3)

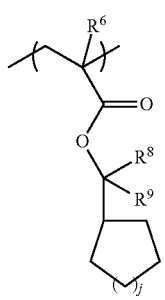

(2-4)

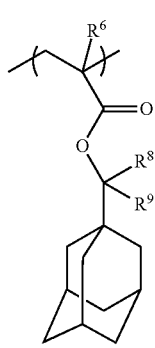

(2-5)

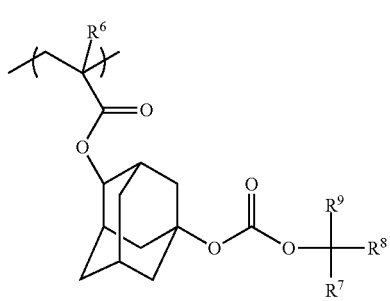

(2-6)

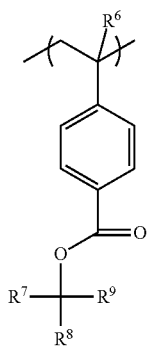

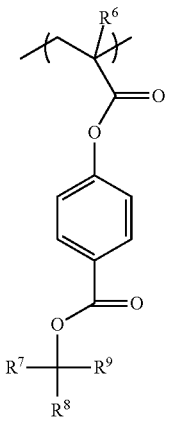
(2-7)
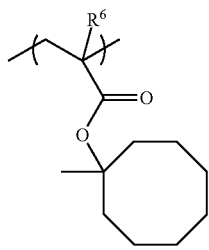
In the above formulae (2-1) to (2-7), $R^6$ to $R^9$ are as defined in the above formula (2); and i and j are each independently an integer of 1 to 4.
Examples of the structural units (II-1) to (II-7) include structural units represented by the following formulae, and the like.
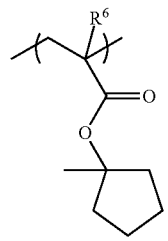 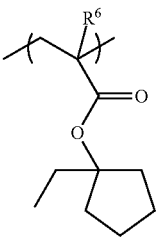 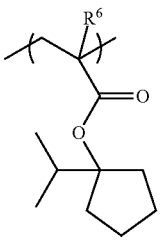
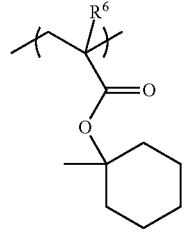 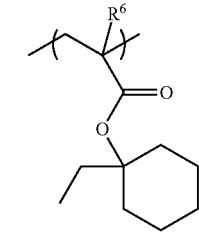
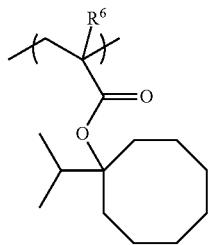 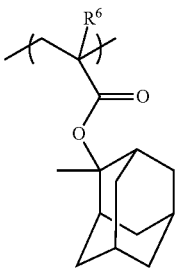
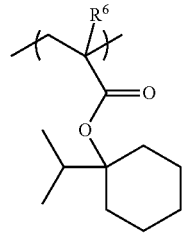 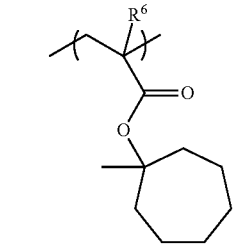
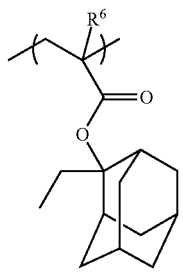 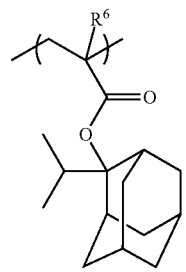
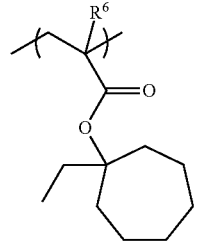 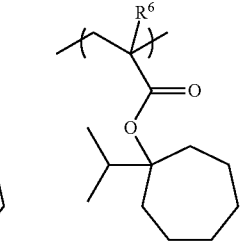
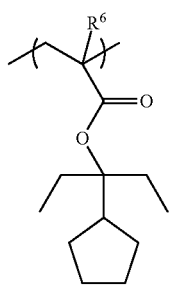 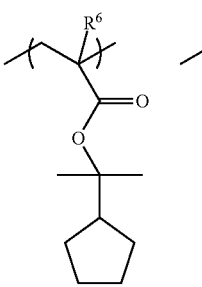
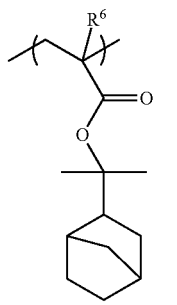 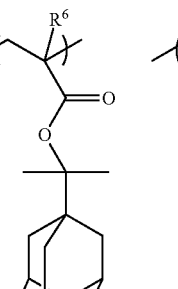

-continued
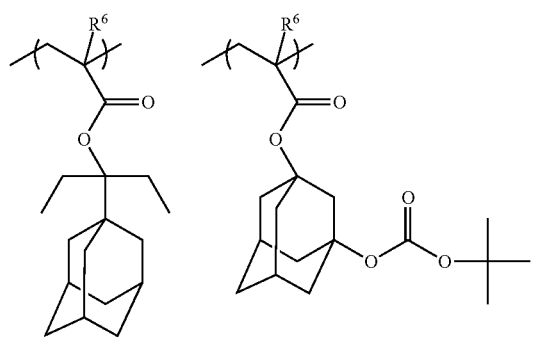
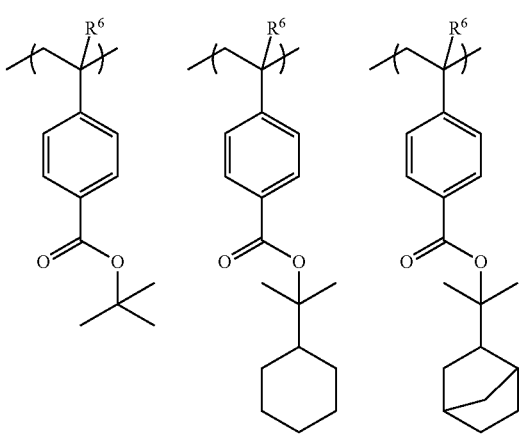
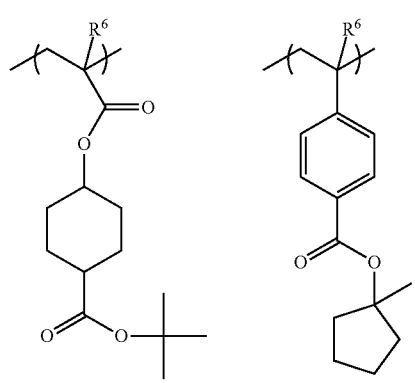
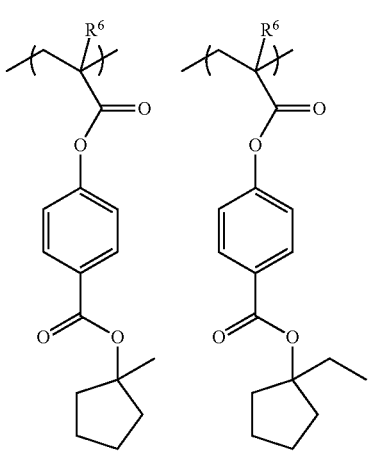
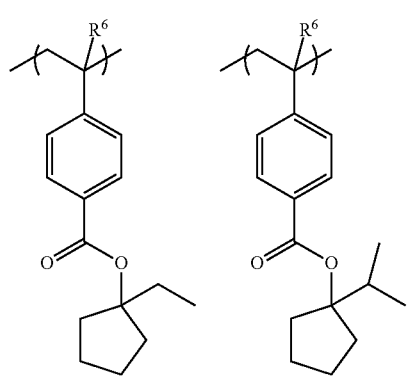
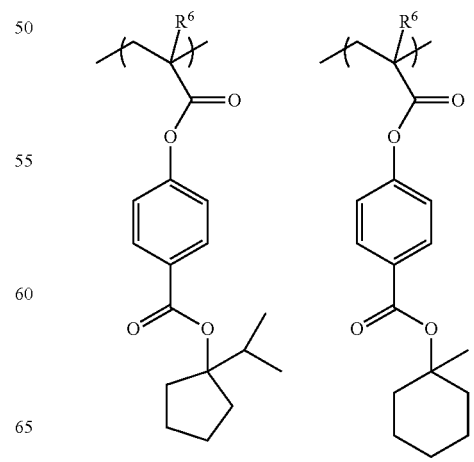
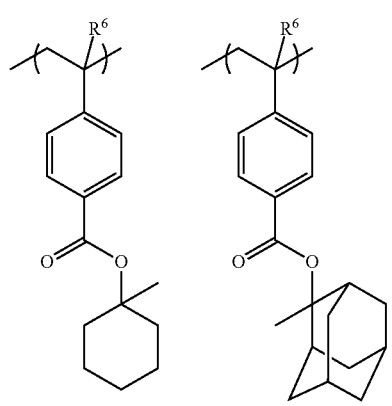

-continued

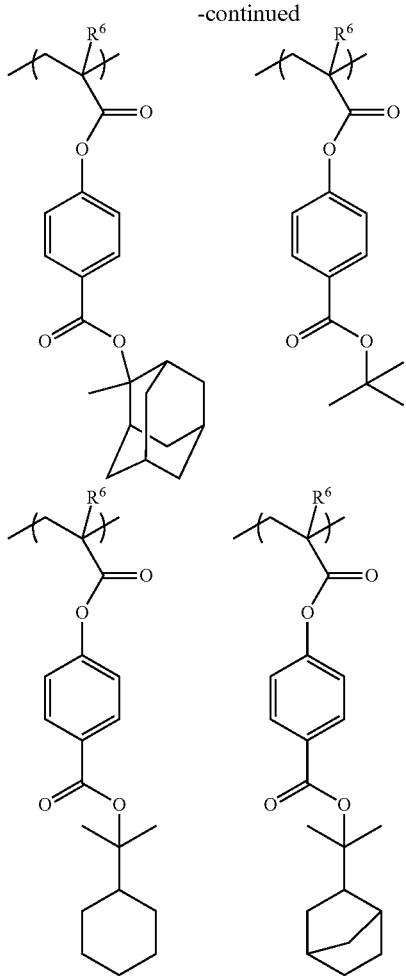

In the above formulae, $R^6$ is as defined in the above formula (2).

The structural unit (II) is preferably the structural unit (II-1), the structural unit (II-2), the structural unit (II-5) or the structural unit (II-6), more preferably a structural unit derived from 1-alkyl-1-cyclopentyl(meth)acrylate, a structural unit derived from 2-alkyl-2-adamantyl(meth)acrylate, a structural unit derived from 3-(t-alkyloxycarbonyloxy) adamantyl-1-yl(meth)acrylate, or a structural unit derived from p-(t-(cyclo)alkyloxycarbonyl)styrene.

The proportion of the structural unit (II) with respect to the total structural units constituting the polymer (A) is preferably 10 mol % to 80 mol %, more preferably 20 mol % to 75 mol %, still more preferably 30 mol % to 70 mol %, and particularly preferably 35 mol % to 60 mol %. When the aforementioned proportion falls within the above range, the sensitivity of the radiation-sensitive resin composition may be further improved, and consequently the LWR performance, the resolution, the rectangularity of the cross-sectional shape, and the depth of focus may be further improved. When the aforementioned proportion is less than the lower limit, pattern formability of the radiation-sensitive resin composition may be deteriorated. When the proportion is greater than the upper limit, adhesiveness of a resist pattern to a substrate may be deteriorated.

Structural Unit (III)

The structural unit (III) is a structural unit represented by at least one selected from the group consisting of the following formulae (3-1) to (3-4) (hereinafter, may be also referred to as "structural units (III-1) to (III-4)"). Due to the polymer (A) having the structural unit (III), the radiation-sensitive resin composition can achieve an improvement of adhesiveness of a resulting resist pattern to a substrate. In addition, in the case of a KrF exposure, an EUV exposure or an electron beam exposure, the sensitivity of the radiation-sensitive resin composition may be increased.

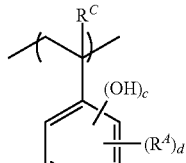
(3-1)

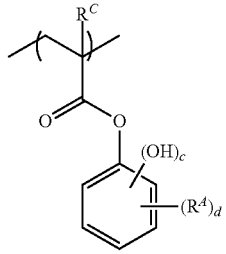
(3-2)

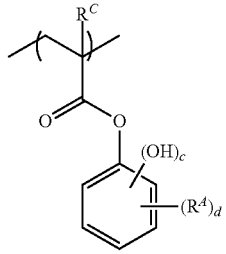
(3-3)

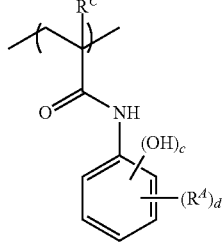
(3-4)

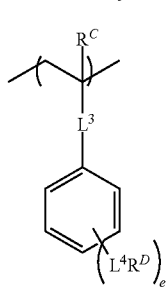

In the above formulae (3-1) to (3-4), $R^C$s each independently represent a hydrogen atom or an alkyl group having 1 to 5 carbon atoms.

In the above formulae (3-1) to (3-3), "c"s are each independently an integer of 1 to 3; $R^A$s each independently represent an alkyl group having 1 to 5 carbon atoms; and "d"s are each independently an integer of 0 to 4, wherein a sum of c and d is no greater than 5, and wherein in a case where $R^A$ is present in a plurality of number, a plurality of $R^A$s may be each identical or different.

In the above formula (3-4), $L^3$ and $L^4$ each independently represent a single bond, a methylene group, an alkylene group having 2 to 5 carbon atoms, a cycloalkylene group having 3 to 15 carbon atoms, an arylene group having 6 to 20 carbon atoms, or a divalent group obtained by combining a methylene group, an alkylene group having 2 to 5 carbon atoms, a cycloalkylene group having 3 to 15 carbon atoms or an arylene group having 6 to 20 carbon atoms with at least one selected from the group consisting of —O— and —CO—; $R^D$ represents a hydrogen atom, a carboxy group, a monovalent chain hydrocarbon group having 1 to 5 carbon atoms, an alkoxy group having 1 to 5 carbon atoms, an alkoxycarbonyl group having 2 to 5 carbon atoms, or a group that includes a hydroxy group at an end thereof and includes at least one fluorine atom or fluorinated alkyl group on a carbon atom adjacent to the hydroxy group; and e is an integer of 1 to 5, wherein in a case where $L^4$ and $R^D$ are each present in a plurality of number, a plurality of $L^4$s may be each identical or different and a plurality of $R^D$s may be each identical or different.

Examples of the alkyl group having 1 to 5 carbon atoms which may be represented by $R^A$ or $R^C$ include a methyl group, an ethyl group, a linear or branched propyl group, a linear or branched butyl group, a linear or branched pentyl group, and the like.

In light of the copolymerizability of a monomer that gives the structural unit (III), $R^C$ is preferably a hydrogen atom or a methyl group, and more preferably a hydrogen atom.

$R^B$ preferably represents a methyl group. Preferably, d is 0.

Examples of the alkylene group having 2 to 5 carbon atoms which may be represented by $L^3$ or $L^4$ include an ethylene group, a propylene group, a butylene group, a pentylene group, and the like.

Examples of the cycloalkylene group having 3 to 15 carbon atoms which may be represented by $L^3$ or $L^4$ include a cyclopropylene group, a cyclobutylene group, a cyclopentylene group, a cyclohexylene group, a norbornylene group, an adamantylene group, and the like.

Examples of the arylene group having 6 to 20 carbon atoms which may be represented by $L^3$ or $L^4$ include a phenylene group, a tolylene group, a xylylene group, a naphthylene group, an anthrylene group, and the like.

Examples of the divalent group, which may be represented by $L^3$ or $L^4$, obtained by combining a methylene group, an alkylene group having 2 to 5 carbon atoms, a cycloalkylene group having 3 to 15 carbon atoms or an arylene group having 6 to 20 carbon atoms with at least one selected from the group consisting of —O— and —CO— include (cyclo)alkyleneoxy groups, (cyclo)alkylenecarbonyl groups, (cyclo)alkylenecarbonyloxy groups, (cyclo)alkyleneoxycarbonyl groups, aryleneoxy groups, arylenecarbonyl groups, arylenecarbonyloxy groups, aryleneoxycarbonyl groups, and the like.

Examples of the monovalent chain hydrocarbon group having 1 to 5 carbon atoms which may be represented by $R^D$ include:

alkyl groups such as a methyl group, an ethyl group, a propyl group and a butyl group;

alkenyl groups such as an ethenyl group, a propenyl group and a butenyl group;

alkynyl groups such as an ethynyl group, a propynyl group and a butynyl group; and the like.

Examples of the alkoxy group having 1 to 5 carbon atoms which may be represented by $R^D$ include a methoxy group, an ethoxy group, a propoxy group, a butoxy group, a pentyloxy group, and the like.

Examples of the alkoxycarbonyl group having 1 to 5 carbon atoms which may be represented by $R^D$ include a methoxycarbonyl group, an ethoxycarbonyl group, a propoxycarbonyl group, and the like.

Examples of the group, which may be represented by $R^D$, that includes a hydroxy group at an end thereof and includes at least one fluorine atom or fluorinated alkyl group on a carbon atom adjacent to the hydroxy group include a hydroxy-di(trifluoromethyl)methyl group, a hydroxy-methyl-trifluoromethylmethyl group, a hydroxy-di(pentafluoroethyl)methyl group, and the like.

The structural unit (III) is preferably the structural unit (III-1) or the structural unit (III-4), and more preferably the structural unit (III-1).

The proportion of the structural unit (III) with respect to the total structural units constituting the polymer (A) is preferably 0 mol % to 50 mol %, and more preferably 0 mol % to 30 mol %. Due to the polymer (A) having the structural unit (III), the radiation-sensitive resin composition can achieve a further improvement of the adhesiveness of a resist pattern to a substrate. In addition, the sensitivity in a KrF exposure, an EUV exposure and an electron beam exposure can be further improved.

Structural Unit (IV)

The structural unit (IV) has at least one selected from the group consisting of a lactone structure, a cyclic carbonate structure and a sultone structure (except for those corresponding to structural unit (I)). Due to the polymer (A) further having the structural unit (IV), the solubility of the polymer (A) in a developer solution can be further adjusted, and consequently the radiation-sensitive resin composition can achieve an improvement of the LWR performance, the resolution, the rectangularity of the cross-sectional shape, and the depth of focus. In addition, adhesiveness of a resist pattern formed from the radiation-sensitive resin composition to the substrate can be improved.

Examples of the structural unit (IV) include structural units represented by the following formulae, and the like.

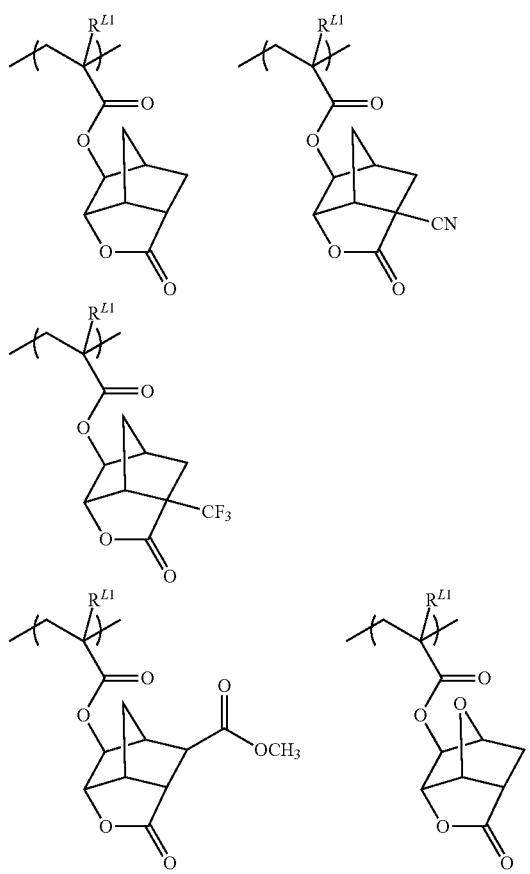

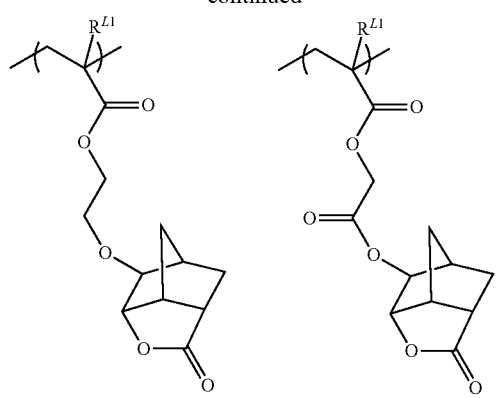
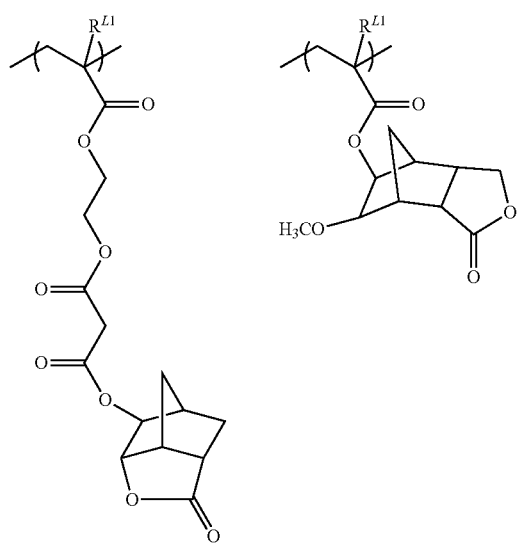
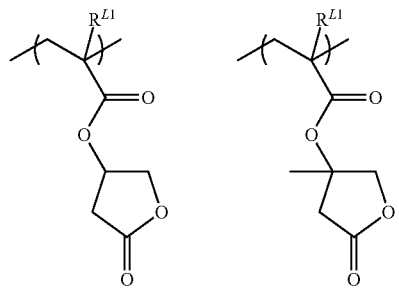
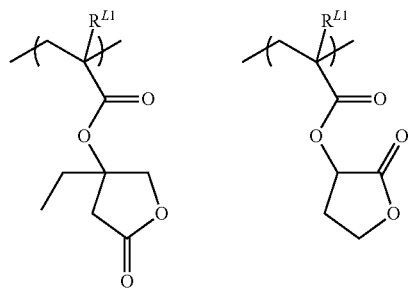
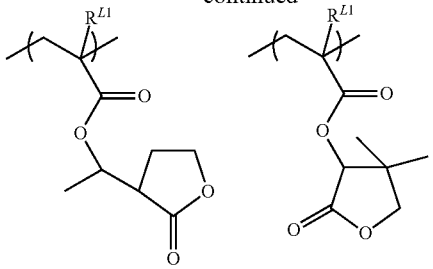
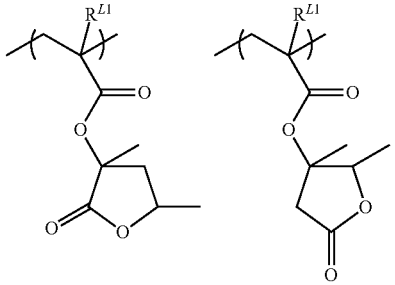
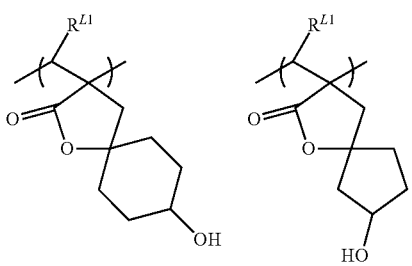
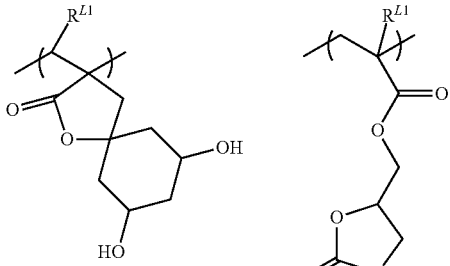
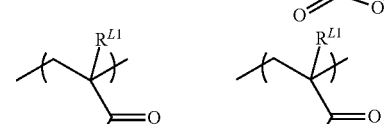
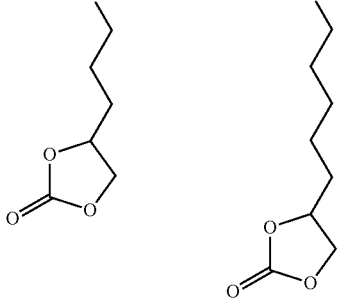

-continued
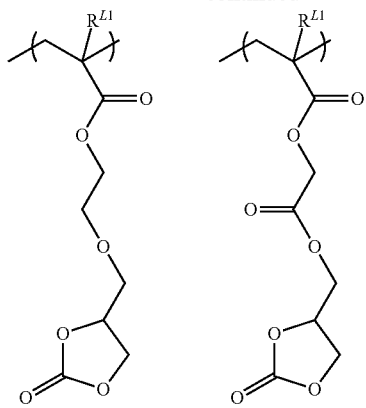
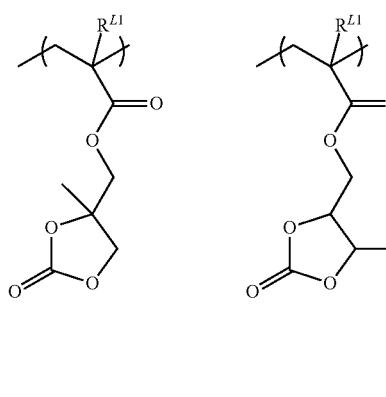
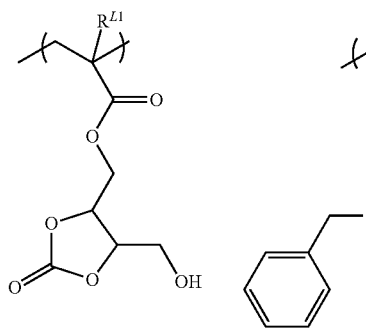
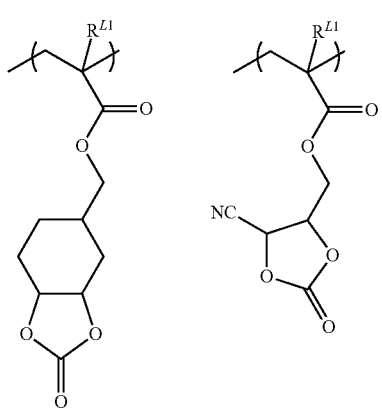
-continued
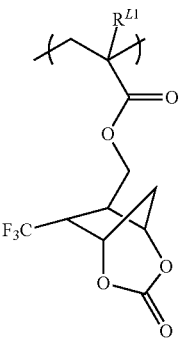
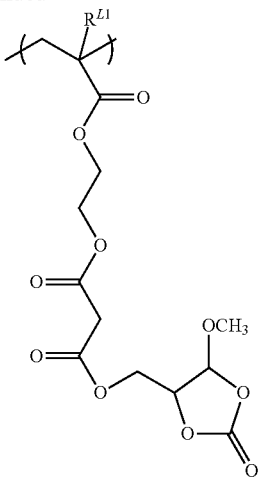
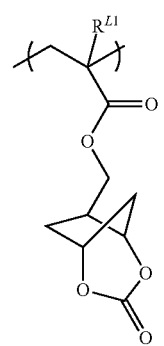
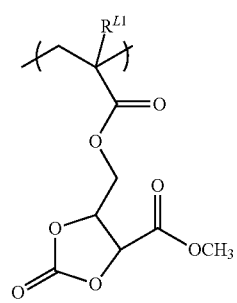
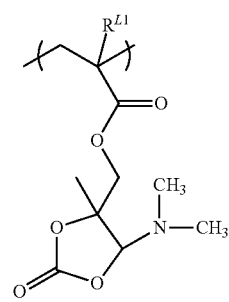
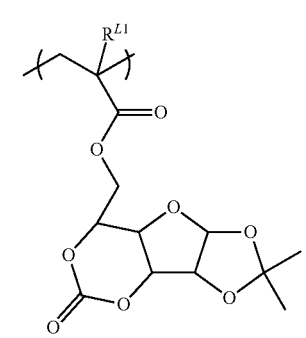
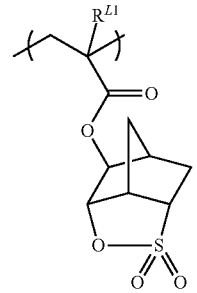
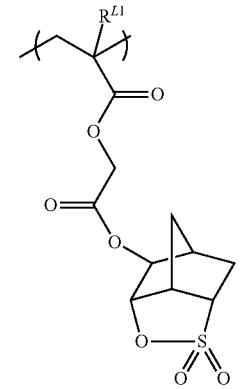

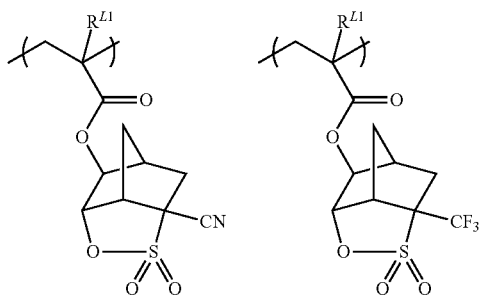
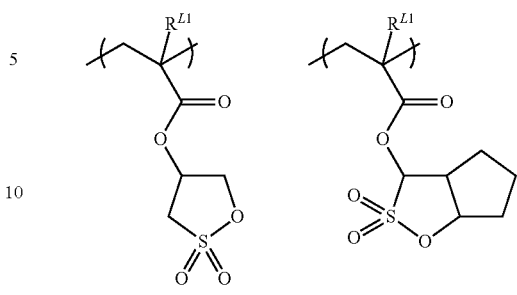
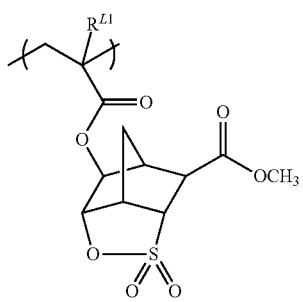

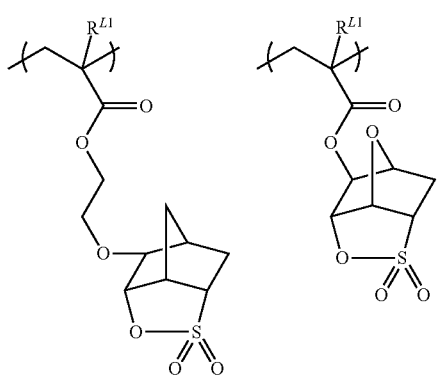

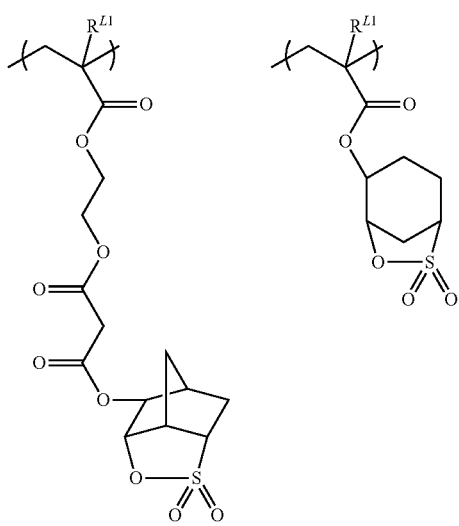

In the above formulae, $R^{L1}$ represents a hydrogen atom, a fluorine atom, a methyl group or a trifluoromethyl group.

Of these, the structural unit (IV) is preferably a structural unit that includes a norbornanelactone structure, a structural unit that includes a γ-butyrolactone structure, a structural unit that includes an ethylene carbonate structure, or a structural unit that includes a norbornanesultone structure, and more preferably a structural unit derived from norbornanelacton-yl(meth)acrylate, a structural unit derived from cyanonorbomanelacton-yl(meth)acrylate, a structural unit derived from oxynorbornanelacton-yl(meth)acrylate, a structural unit derived from butyrolacton-yl(meth)acrylate, or a structural unit derived from norbornanesulton-yl(meth)acrylate.

The proportion of the structural unit (IV) with respect to the total structural units constituting the polymer (A) is preferably 0 mol % to 70 mol %, more preferably 0 mol % to 60 mol %, and still more preferably 20 mol % to 55 mol %. When the aforementioned proportion falls within the above range, the radiation-sensitive resin composition can achieve a further improvement of the LWR performance, the resolution, the rectangularity of the cross-sectional shape, and the depth of focus. In addition, the adhesiveness of the resist pattern formed from the radiation-sensitive resin composition to a substrate can be further improved.

Structural Unit (V)

The structural unit (V) includes a hydroxy group (except for those corresponding to the structural unit (I)). Due to the polymer (A) further having the structural unit (V), the solubility of the polymer (A) in a developer solution can be further adjusted, and consequently the radiation-sensitive resin composition can achieve an improvement of the LWR performance, the resolution, the rectangularity of the cross-sectional shape, and the depth of focus.

Examples of the structural unit (V) include structural units represented by the following formulae, and the like.

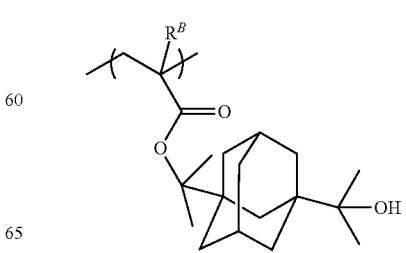

-continued
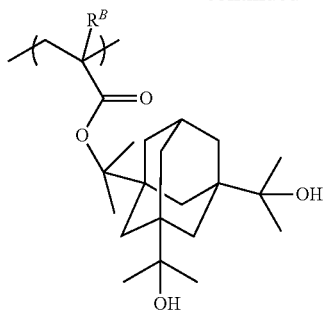
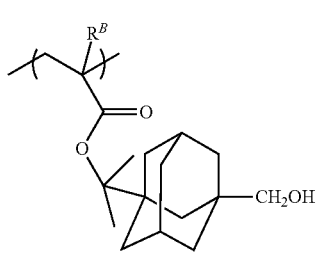
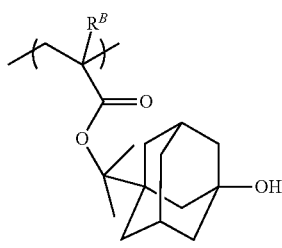
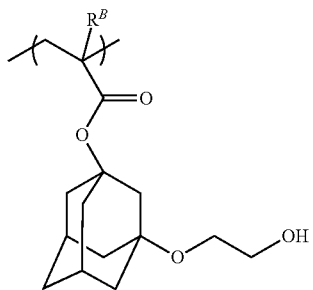
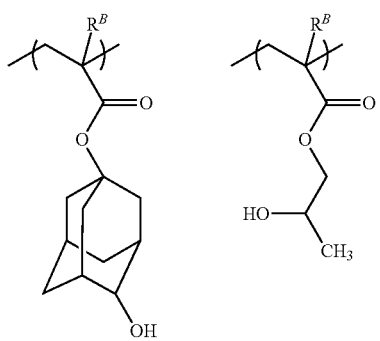
-continued
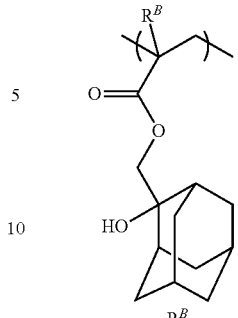
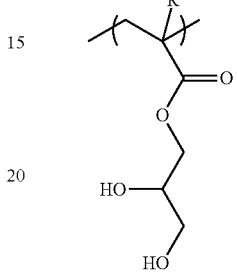
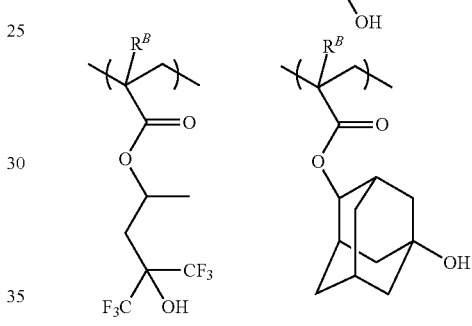
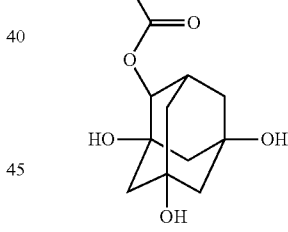
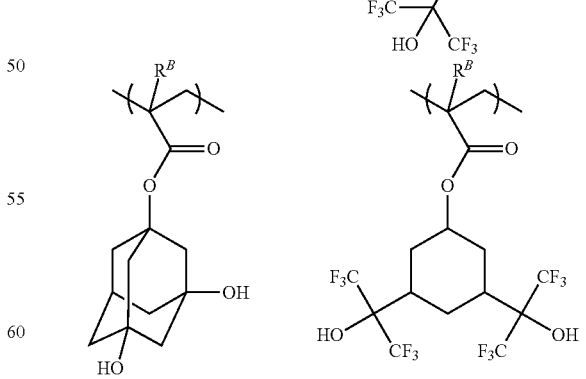
In the above formulae, $R^B$ represents a hydrogen atom, a fluorine atom, a methyl group or a trifluoromethyl group.
The proportion of the structural unit (V) with respect to the total structural units constituting the polymer (A) is preferably 0 mol % to 70 mol %, more preferably 0 mol % to 60 mol %, and still more preferably 20 mol % to 55 mol %. When the aforementioned proportion falls within the above range, the radiation-sensitive resin composition can achieve a further improvement of the LWR performance, the resolution, the rectangularity of the cross-sectional shape, and the depth of focus.

The polymer (A) may have other structural unit in addition to the structural units (I) to (V) described above. The other structural unit is exemplified by a structural unit that includes a ketonic carbonyl group, a cyano group, a carboxy group, a nitro group, an amino group or the like, etc. Of these, a structural unit that includes a ketonic carbonyl group is preferred, and a structural unit derived from oxoadamantyl (meth)acrylate is more preferred. The proportion of these structural units is preferably no greater than 30 mol %, and more preferably no greater than 20 mol %. Moreover, the other structural unit is also exemplified by a structural unit that includes a structure in which a hydrogen atom of a phenolic hydroxyl group is substituted with an acid-labile group, and the like. Examples of the acid-labile group include: alkyl groups having an atomic bonding on a tertiary carbon, such as a t-butyl group; alkoxydialkylmethyl groups having an atomic bonding on a tertiary carbon, such as a 1-methoxypropan-2-yl group; and the like. Of these, as the aforementioned structural unit, a structural unit derived from t-alkyloxystyrene and a structural unit derived from alkoxydialkylmethoxystyrene are preferred, and a structural unit derived from t-butoxystyrene is more preferred. The proportion of these structural units is preferably no greater than 80 mol %, and more preferably no greater than 60 mol %. The polymer (A) may have other structural unit in addition to the aforementioned structural units.

The content of the polymer (A) with respect to the total solid content of the radiation-sensitive resin composition is preferably no less than 25% by mass. When the content of the polymer (A) falls within the above range, the radiation-sensitive resin composition enables further superior LWR performance, resolution, rectangularity of the cross-sectional shape, and depth of focus to be achieved. When the content of the polymer (A) is below the above range, performances of the radiation-sensitive resin composition, such as the LWR performance, the resolution, the rectangularity of the cross-sectional shape, and the depth of focus, are likely to be deteriorated. It is to be noted that the "total solid content" as referred to means the sum of the entirety of all components, excluding the solvent, of the radiation-sensitive resin composition. The content of the polymer (A) with respect to the total solid content of the radiation-sensitive resin composition is more preferably no less than 40% by mass, still more preferably no less than 60% by mass, particularly preferably no less than 80% by mass, and further particularly preferably no less than 85% by mass.

Synthesis Method of Polymer (A)

The polymer (A) can be synthesized, for example, by polymerizing monomer(s) that give(s) each structural unit in an appropriate solvent with the use of a radical polymerization initiator, or the like.

The radical polymerization initiator is exemplified by: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Of these, AIBN and dimethyl 2,2'-azobisisobutyrate are preferred, and AIBN is more preferred. These radical initiators may be used either alone, or as a mixture of two or more types thereof.

Examples of the solvent for use in the polymerization include:

alkanes such as n-pentane, n-hexane, n-heptane, n-octane, n-nonane and n-decane;

cycloalkanes such as cyclohexane, cycloheptane, cyclooctane, decalin and norbomane;

aromatic hydrocarbons such as benzene, toluene, xylene, ethylbenzene and cumene;

halogenated hydrocarbons such as chlorobutanes, bromohexanes, dichloroethanes, hexamethylene dibromide and chlorobenzene;

saturated carboxylic acid esters such as ethyl acetate, n-butyl acetate, i-butyl acetate and methyl propionate;

ketones such as acetone, methyl ethyl ketone, 4-methyl-2-pentanone and 2-heptanone;

ethers such as tetrahydrofuran, dimethoxyethanes and diethoxyethanes;

alcohols such as methanol, ethanol, 1-propanol, 2-propanol and 4-methyl-2-pentanol; and the like. These solvents for use in the polymerization may be used alone, or two or more types thereof may be used in combination.

The reaction temperature in the polymerization is typically 40° C. to 150° C., and preferably 50° C. to 120° C. The reaction time period is typically 1 hour to 48 hrs, and preferably 1 hour to 24 hrs.

Although the polystyrene equivalent weight average molecular weight (Mw) of the polymer (A) as determined by gel permeation chromatography (GPC) is not particularly limited, the Mw of the polymer (A) is preferably no less than 1,000 and no greater than 50,000, more preferably no less than 2,000 and no greater than 30,000, still more preferably no less than 3,000 and no greater than 20,000, and particularly preferably no less than 5,000 and no greater than 15,000. When the Mw of the polymer (A) falls within the above range, coating properties and inhibitory ability of development defects of the radiation-sensitive resin composition may be improved. When the Mw of the polymer (A) is less than the above lower limit, a resist film exhibiting sufficient heat resistance may not be obtained. When the Mw of the polymer (A) is greater than the upper limit, developability of the resist film may be deteriorated.

The ratio (Mw/Mn) of the Mw to the polystyrene equivalent number average molecular weight (Mn) as determined by GPC of the polymer (A) is typically no less than 1 and no greater than 5, preferably no less than 1 and no greater than 3, and still more preferably no less than 1 and no greater than 2.

The Mw and the Mn of the polymer as referred to herein mean a value determined using gel permeation chromatography (GPC) under the following conditions:

GPC columns: G2000 HXL×2, G3000 HXL×1, and G4000 HXL×1 (all manufactured by Tosoh Corporation);

column temperature: 40° C.;

elution solvent: tetrahydrofuran (manufactured by Wako Pure Chemical Industries, Ltd.);

flow rate: 1.0 mL/min;

sample concentration: 1.0% by mass;

amount of injected sample: 100 μL;

detector: differential refractometer; and standard substance: mono-dispersed polystyrene.

The content of the low-molecular weight matter in the polymer (A) is preferably no greater than 0.5% by mass, more preferably no greater than 0.2% by mass, and still more preferably no greater than 0.1% by mass. When the content of the low-molecular weight matter in the polymer (A) falls within the above range, the inhibitory ability of development defects of the radiation-sensitive resin composition can be improved. It is to be noted that the low-molecular weight matter in the polymer as referred to means matter having a molecular weight of no greater than 1,000.

The content (% by mass) of the low-molecular weight matter (i.e., matter having a molecular weight of no greater than 1,000) of the polymer as referred to herein is a value determined by high performance liquid chromatography (HPLC) under the following conditions:

HPLC column: Intersil ODS-25 µm, 4.6 mmφ×250 mm (manufactured by GL Sciences, Inc.);

elution solvent: acrylonitrile/0.1% by mass aqueous phosphoric acid solution;

flow rate: 1.0 mL/min;

sample concentration: 1.0% by mass;

amount of injected sample: 100 µL; and detector: differential refractometer.

(B) Acid Generator

The acid generator (B) is a substance that generates an acid upon an exposure. The acid thus generated allows an acid-labile group included in the polymer (A), or a polymer (E) described later or the like to be dissociated, thereby generating a carboxy group or the like. As a result, the solubility of these polymers in a developer solution is altered, and consequently a resist pattern can be formed from the radiation-sensitive resin composition. The acid generator (B) may be contained in the radiation-sensitive resin composition either in the form of a low molecular weight compound described later (hereinafter, may be also referred to as "(B) acid generating agent" or "(B) acid generating agent", as appropriate), or in the form of an acid generating group incorporated as a part of the polymer, or may be in both of these forms.

The acid generating agent (B) is exemplified by an onium salt compound, an N-sulfonyloxyimide compound, a halogen-containing compound, a diazo ketone compound, and the like.

The onium salt compound is exemplified by a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)-hexane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate, 1-(4-n-butoxynaphthalen-1-yl) tetrahydrothiophenium camphorsulfonate, 1-(6-n-butoxynaphthalen-2-yl)tetrahydrothiophenium trifluoromethanesulfonate, 1-(6-n-butoxynaphthalen-2-yl) tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl) tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy) bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$] dodecanyl)-1,1-difluoroethanesulfonyloxy)bicyclo[2.2.1] hept-5-ene-2,3-dicarboxyimide, N-(camphorsulfonyloxy) bicyclo[2.2.1]hept-5-ene-2,3-dicarboxyimide, and the like.

The acid generating agent (B) is preferably a compound represented by the following formula (4). It is presumed that when the acid generating agent (B) has the following structure, the diffusion length of an acid generated upon an exposure in the resist film would be decreased more properly due to an interaction of the acid with a polar structure included in the polymer (A) or the polymer (E), and as a result, the radiation-sensitive resin composition can achieve a further improvement of the LWR performance, the resolution, the rectangularity of the cross-sectional shape and the depth of focus.

$$R^{10}-R^{11}-SO_3^-X^+ \qquad (4)$$

In the above formula (4), $R^{10}$ represents a monovalent group that includes an alicyclic structure having 6 or more ring atoms, or a monovalent group that includes an aliphatic heterocyclic structure having 6 or more ring atoms; $R^{11}$ represents a fluorinated alkanediyl group having 1 to 10 carbon atoms; and $X^+$ represents a monovalent photodegradable onium cation.

The "number of ring atoms" as referred to in regard to $R^{10}$ means the number of the atoms constituting the ring of the alicyclic structure or the aliphatic heterocyclic structure, and in regard to a polycyclic alicyclic structure and a polycyclic aliphatic heterocyclic structure, the "number of ring atoms" means the number of the atoms constituting the polycyclic structure.

Examples of the monovalent group that includes an alicyclic structure having 6 or more ring atoms, which may be represented by $R^{10}$, include:

monocyclic cycloalkyl groups such as a cyclooctyl group, a cyclononyl group, a cyclodecyl group and a cyclododecyl group;

monocyclic cycloalkenyl groups such as a cyclooctenyl group and a cyclodecenyl group;

polycyclic cycloalkyl groups such as a norbornyl group, an adamantyl group, a tricyclodecyl group and a tetracyclododecyl group;

polycyclic cycloalkenyl groups such as a norbornenyl group and a tricyclodecenyl group; and the like.

Examples of the monovalent group that includes an aliphatic heterocyclic structure having 6 or more ring atoms, which may be represented by $R^{10}$, include:

groups that include a lactone structure, such as a norbornanelacton-yl group;

groups that include a sultone structure, such as a norbornanesulton-yl group;

oxygen atom-containing heterocyclic groups such as an oxacycloheptyl group and an oxanorbornyl group;

nitrogen atom-containing heterocyclic groups such as an azacyclohexyl group, an azacycloheptyl group and a diazabicyclooctan-yl group;

sulfur atom-containing heterocyclic groups such as a thiacycloheptyl group and a thianorbornyl group; and the like.

In light of attaining a more proper diffusion length of the acid described above, the number of ring atoms of the group represented by $R^{10}$ is preferably no less than 8, more preferably 9 to 15, and still more preferably 10 to 13.

Of these, $R^{10}$ represents preferably a monovalent group that includes an alicyclic structure having 9 or more ring atoms, or a monovalent group that includes an aliphatic heterocyclic structure having 9 or more ring atoms, more preferably an adamantyl group, a hydroxyadamantyl group, a norbomanelacton-yl group, or a 5-oxo-4-oxatricyclo [4.3.1.1$^{3,8}$]undecan-yl group, and still more preferably an adamantyl group.

Examples of the fluorinated alkanediyl group having 1 to 10 carbon atoms which is represented by $R^{11}$ include groups obtained by substituting with a fluorine atom, at least one hydrogen atom included in an alkanediyl group having 1 to 10 carbon atoms such as a methanediyl group, an ethanediyl group and a propanediyl group; and the like.

Of these, a fluorinated alkanediyl group in which one or more fluorine atoms bond to a carbon atom adjacent to a $SO_3^-$ group is preferred, and a fluorinated alkanediyl group in which two fluorine atoms bond to a carbon atom adjacent to a $SO_3^-$ group is more preferred, and a 1,1-difluoromethanediyl group, a 1,1-difluoroethanediyl group, a 1,1,3,3,3-pentafluoro-1,2-propanediyl group, a 1,1,2,2-tetrafluoroethanediyl group, a 1,1,2,2-tetrafluorobutanediyl group and a 1,1,2,2-tetrafluorohexanediyl group are still more preferred.

The monovalent photodegradable onium cation represented by $X^+$ is a cation that is degraded by irradiation with an exposure light. At light-exposed sites, a sulfonic acid is generated from a proton generated upon the degradation of the photodegradable onium cation and a sulfonate anion.

Examples of the monovalent photodegradable onium cation represented by $X^+$ include radiation-degradable onium cations that contain an element such as S, I, O, N, P, Cl, Br, F, As, Se, Sn, Sb, Te and Bi. Examples of the cation that contains S (sulfur) as the element include sulfonium cations, tetrahydrothiophenium cations and the like, and examples of the cation that contains I (iodine) as the element include iodonium cations and the like. Of these, a sulfonium cation represented by the following formula (X-1), a tetrahydrothiophenium cation represented by the following formula (X-2), and an iodonium cation represented by the following formula (X-3) are preferred.

(X-1)

(X-2)

(X-3)

In the above formula (X-1), $R^{a1}$, $R^{a2}$ and $R^{a3}$ each independently represent a substituted or unsubstituted linear or branched alkyl group having 1 to 12 carbon atoms, a substituted or unsubstituted aromatic hydrocarbon group having 6 to 12 carbon atoms, $-OSO_2-R^P$ or $-SO_2-R^Q$, or two or more of these groups taken together represent a ring structure; $R^P$ and $R^Q$ each independently represent a substituted or unsubstituted linear or branched alkyl group having 1 to 12 carbon atoms, a substituted or unsubstituted alicyclic hydrocarbon group having 5 to 25 carbon atoms, or a substituted or unsubstituted aromatic hydrocarbon group having 6 to 12 carbon atoms; and k1, k2 and k3 are each independently an integer of 0 to 5, wherein $R^{a1}$ to $R^{a3}$, and $R^P$ and $R^Q$ are each present in a plurality of number, a plurality of $R^{a1}$s to $R^{a3}$s may be each identical or different, a plurality of $R^P$s may be each identical or different and a plurality of $R^Q$s may be each identical or different.

In the above formula (X-2), $R^{b1}$ represents a substituted or unsubstituted linear or branched alkyl group having 1 to 8 carbon atoms, or a substituted or unsubstituted aromatic hydrocarbon group having 6 to 8 carbon atoms; k4 is an integer of 0 to 7, wherein in a case where $R^{b1}$ is present in a plurality of number, a plurality of $R^{b1}$s are identical or different, and a plurality of $R^{b1}$ may taken together represent a ring structure; $R^{b2}$ represents a substituted or unsubstituted linear or branched alkyl group having 1 to 7 carbon atoms, or a substituted or unsubstituted aromatic hydrocarbon group having 6 or 7 carbon atoms; k5 is an integer of 0 to 6, wherein in a case where $R^{b2}$ is present in a plurality of number, a plurality of $R^{b2}$s may be identical or different, and a plurality of $R^{b2}$ may taken together represent a ring structure; and t is an integer of 0 to 3.

In the above formula (X-3), $R^{c1}$ and $R^{c2}$ each independently represent a substituted or unsubstituted linear or branched alkyl group having 1 to 12 carbon atoms, a substituted or unsubstituted aromatic hydrocarbon group having 6 to 12 carbon atoms, —OSO$_2$—R$^R$ or —SO$_2$—R$^S$, or two or more of these groups taken together represent a ring structure; R$^R$ and R$^S$ each independently represent a substituted or unsubstituted linear or branched alkyl group having 1 to 12 carbon atoms, a substituted or unsubstituted alicyclic hydrocarbon group having 5 to 25 carbon atoms, or a substituted or unsubstituted aromatic hydrocarbon group having 6 to 12 carbon atoms; and k6 and k7 are each independently an integer of 0 to 5, wherein in a case where $R^{c1}$, $R^{c2}$, R$^R$ and R$^S$ are each present in a plurality of number, a plurality of $R^{c1}$s may be each identical or different, a plurality of $R^{c2}$s may be each identical or different, a plurality of R$^R$s may be each identical or different and a plurality of R$^S$s may be each identical or different.

Examples of the unsubstituted linear alkyl group which may be represented by $R^{a1}$ to $R^{a3}$, $R^{b1}$, $R^{b2}$, $R^{c1}$ or $R^{c2}$ include a methyl group, an ethyl group, a n-propyl group, a n-butyl group, and the like.

Examples of the unsubstituted branched alkyl group which may be represented by $R^{a1}$ to $R^{a3}$, $R^{b1}$, $R^{b2}$, $R^{c1}$ or $R^{c2}$ include an i-propyl group, an i-butyl group, a sec-butyl group, a t-butyl group, and the like.

Examples of the unsubstituted aromatic hydrocarbon group which may be represented by $R^{a1}$ to $R^{a3}$, $R^{c1}$ or $R^{c2}$ include: aryl groups such as a phenyl group, a tolyl group, a xylyl group, a mesityl group and a naphthyl group; aralkyl groups such as a benzyl group and a phenethyl group; and the like.

Examples of the unsubstituted aromatic hydrocarbon group which may be represented by $R^{b1}$ or $R^{b2}$ include a phenyl group, a tolyl group, a benzyl group, and the like.

Examples of the substituent which may substitute for a hydrogen atom included in the alkyl group and the aromatic hydrocarbon group include: halogen atoms such as a fluorine atom, a chlorine atom, a bromine atom and an iodine atom; a hydroxy group; a carboxy group; a cyano group; a nitro group; an alkoxy group; an alkoxycarbonyl group; an alkoxycarbonyloxy group; an acyl group; an acyloxy group; and the like.

Of these, halogen atoms are preferred, and a fluorine atom is more preferred.

$R^{a1}$ to $R^{a3}$, $R^{b1}$, $R^{b2}$, $R^{c1}$ and $R^{c2}$ represent preferably an unsubstituted linear or branched alkyl group, a fluorinated alkyl group, an unsubstituted monovalent aromatic hydrocarbon group, —OSO$_2$—R'', or —SO$_2$—R'', more preferably a fluorinated alkyl group, an unsubstituted monovalent aromatic hydrocarbon group, and still more preferably a fluorinated alkyl group. R'' represents an unsubstituted monovalent alicyclic hydrocarbon group or an unsubstituted monovalent aromatic hydrocarbon group.

In the above formula (X-1), k1, k2 and k3 are preferably an integer of 0 to 2, more preferably 0 or 1, and still more preferably 0.

In the above formula (X-2), k4 is preferably an integer of 0 to 2, more preferably 0 or 1, and still more preferably 1; and k5 is preferably an integer of 0 to 2, more preferably 0 or 1, and still more preferably 0.

In the above formula (X-3), k6 and k7 are preferably an integer of 0 to 2, more preferably 0 or 1, and still more preferably 0.

Examples of the acid generating agent represented by the above formula (4) include compounds represented by the following formulae (4-1) to (4-11) (hereinafter, may be also referred to as "compounds (4-1) to (4-11)"), and the like.

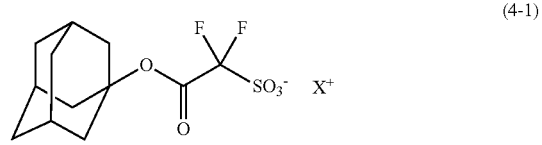

(4-1)

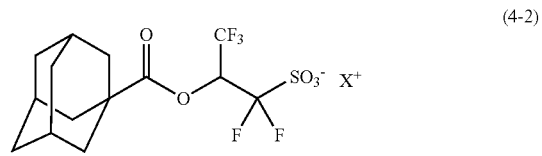

(4-2)

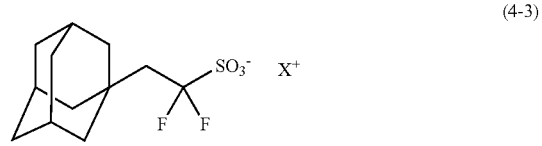

(4-3)

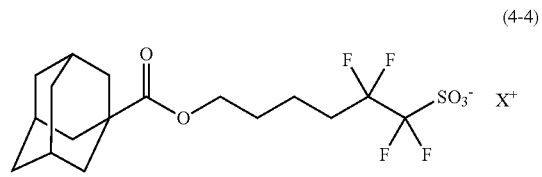

(4-4)

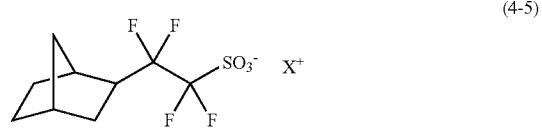

(4-5)

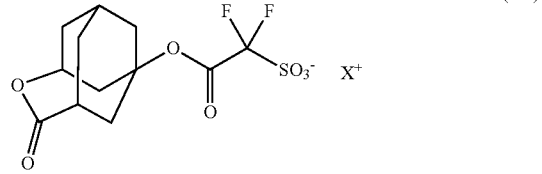

(4-6)

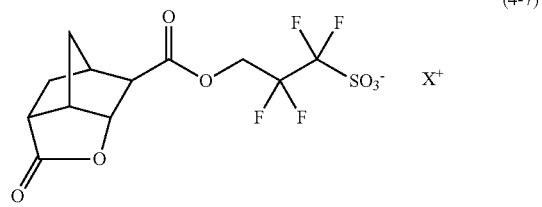

(4-7)

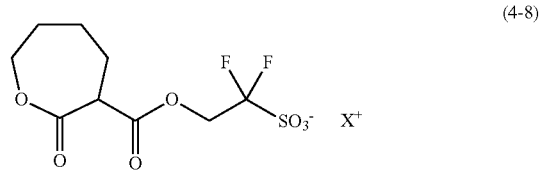

(4-8)

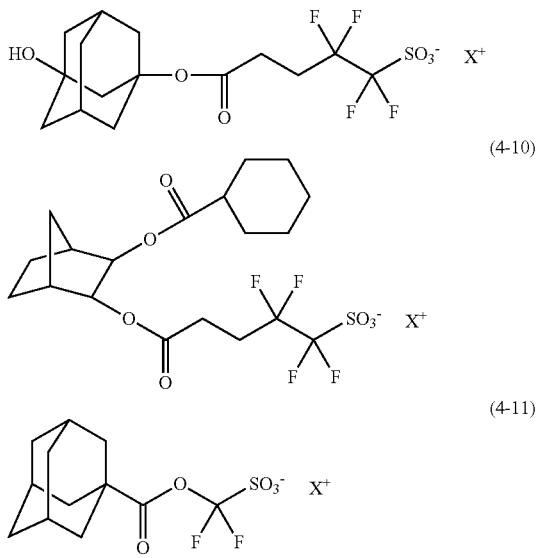

(4-9)

(4-10)

(4-11)

Of these, the acid generating agent (B) is preferably an onium salt compound, more preferably a sulfonium salt, still more preferably a sulfonium salt containing an anion that includes an adamantane structure, a sulfonium salt containing an anion that includes a norbornanesultone structure, a sulfonium salt containing an anion that includes a sulfonamide structure, and particularly preferably the compound (4-2).

In a case where the acid generator (B) is the acid generating agent (B), in light of ensuring the sensitivity and developability of the radiation-sensitive resin composition, the content of the acid generator (B) with respect to 100 parts by mass of the polymer (A) is preferably no less than 0.1 parts by mass and no greater than 30 parts by mass, more preferably no less than 0.5 parts by mass and no greater than 20 parts by mass, still more preferably no less than 1 parts by mass and no greater than 15 parts by mass, and particularly preferably no less than 3 parts by mass and no greater than 15 parts by mass. When the content of the acid generating agent (B) falls within the above range, the sensitivity and developability of the radiation-sensitive resin composition may be further increased. One, or two or more types of the acid generator (B) may be used.

(C) Organic Solvent

The radiation-sensitive resin composition typically contains (C) an organic solvent. The organic solvent (C) is not particularly limited as long as it is capable of dissolving or dispersing at least the polymer (A) and the acid generator (B), as well as the acid diffusion controller (D) and the like contained as desired.

The organic solvent (C) is exemplified by an alcohol solvent, an ether solvent, a ketone organic solvent, an amide solvent, an ester organic solvent, a hydrocarbon solvent, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole (methyl phenyl ether); and the like.

Examples of the ketone solvent include:

chain ketone solvents such as acetone, methyl ethyl ketone, methyl n-propyl ketone, methyl n-butyl ketone, diethyl ketone, methyl iso-butyl ketone, 2-heptanone (methyl n-pentyl ketone), ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonylacetone, and acetophenone; and the like.

Examples of the amide solvent include:

cyclic amide solvents such as N,N'-dimethylimidazolidinone and N-methylpyrrolidone;

chain amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

carbonate solvents such as dimethyl carbonate and diethyl carbonate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, methyl lactate, ethyl lactate, n-butyl lactate, n-amyl lactate, diethyl malonate, dimethyl phthalate and diethyl phthalate; and the like.

Examples of the hydrocarbon solvent include:

aliphatic hydrocarbon solvents such as n-pentane, isopentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Of these, an ester solvent and a ketone solvent are preferred, a polyhydric alcohol partial ether acetate solvent and a cyclic ketone solvent are more preferred, and propylene glycol monomethyl ether acetate and cyclohexanone are still more preferred. The radiation-sensitive resin composition may contain one, or two or more types of the organic solvent (C).

(D) Acid Diffusion Controller

The radiation-sensitive resin composition according to the embodiment of the present invention may contain (D) an acid diffusion controller, as needed.

The acid diffusion controller (D) exerts the effect of controlling a diffusion phenomenon of the acid generated from the acid generator (B) upon an exposure in the resist film, and inhibiting unfavorable chemical reactions in unexposed regions; as a result, storage stability of the resulting radiation-sensitive resin composition is further improved, and a resolution for use as a resist is further improved, while inhibiting variations of the line widths of the resist pattern caused by variations of post-exposure delay from the exposure until a development treatment, which enables the radiation-sensitive resin composition with superior process stability to be obtained. The acid diffusion controller (D) may be contained in the radiation-sensitive resin composition either in the form of a free compound (hereinafter, may be also referred to as "(D) acid diffusion control agent" or "acid diffusion control agent (D)", as appropriate), or in the form incorporated as a part of the polymer, or may be in both of these forms.

The acid diffusion control agent (D) is exemplified by a compound represented by the following formula (5a) (hereinafter, may be also referred to as "nitrogen-containing compound (I)"), a compound having two nitrogen atoms within a single molecule (hereinafter, may be also referred to as "nitrogen-containing compound (II)"), a compound having three nitrogen atoms within a single molecule (hereinafter, may be also referred to as "nitrogen-containing compound (III)"), an amide group-containing compound, a urea compound, a nitrogen-containing heterocyclic compound, and the like.

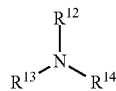
(5a)

In the above formula (5a), $R^{12}$, $R^{13}$ and $R^{14}$ each independently represent a hydrogen atom, an unsubstituted or substituted linear, branched or cyclic alkyl group, an unsubstituted or substituted aryl group or an unsubstituted or substituted aralkyl group.

Examples of the nitrogen-containing compound (I) include: monoalkylamines such as n-hexylamine; dialkylamines such as di-n-butylamine; trialkylamines such as triethylamine and tri-n-pentylamine; aromatic amines such as aniline; and the like.

Examples of the nitrogen-containing compound (II) include ethylenediamine, N,N,N',N'-tetramethylethylenediamine, and the like.

Examples of the nitrogen-containing compound (III) include: polyamine compounds such as polyethyleneimine and polyallylamine; polymers of dimethylaminoethylacrylamide, etc.; and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include: pyridines such as pyridine and 2-methylpyridine; morpholines such as N-propylmorpholine and N-(undecan-1-ylcarbonyloxyethyl)morpholine; pyrazine, and pyrazole; and the like.

A nitrogen-containing organic compound that includes an acid-labile group may also be used as the nitrogen-containing organic compound. Examples of the nitrogen-containing organic compound that includes an acid-labile group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-t-butoxycarbonyl-4-hydroxypiperidine, N-t-amyloxycarbonyl-4-hydroxypiperidine, and the like.

In addition, as the acid diffusion control agent (D), a photodegradable base which is sensitized upon an exposure to generate a weak acid can be used. The photodegradable base is exemplified by an onium salt compound which is degraded upon an exposure and loses its acid diffusion controllability, and the like. Examples of the onium salt compound include a sulfonium salt compound represented by the following formula (5b-1), an iodonium salt compound represented by the following formula (5b-2), and the like.

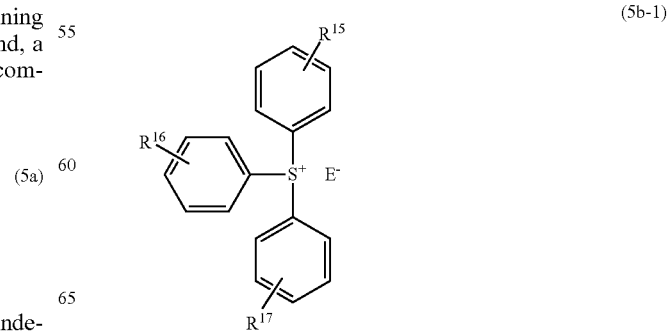
(5b-1)

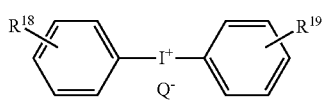

(5b-2)

In the above formulae (5b-1) and (5b-2), $R^{15}$ to $R^{19}$ each independently represent a hydrogen atom, an alkyl group, an alkoxy group, a hydroxy group or a halogen atom; $E^-$ and $Q^-$ each independently represent $OH^-$, $R^\beta$—$COO^-$, $R^\beta$—$SO_3^-$ or an anion represented by the following formula (5b-3), wherein $R^\beta$ represents an alkyl group, an aryl group or an aralkyl group.

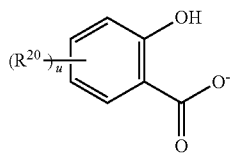

(5b-3)

In the above formula (5b-3), $R^{20}$ represents a linear or branched alkyl group having 1 to 12 carbon atoms, or a linear or branched alkoxyl group having 1 to 12 carbon atoms, wherein a part or all of hydrogen atoms included in the linear or branched alkyl group or the linear or branched alkoxyl group may be substituted with a fluorine atom; and u is an integer of 0 to 2.

Examples of the photodegradable base include compounds represented by the following formulae, and the like.

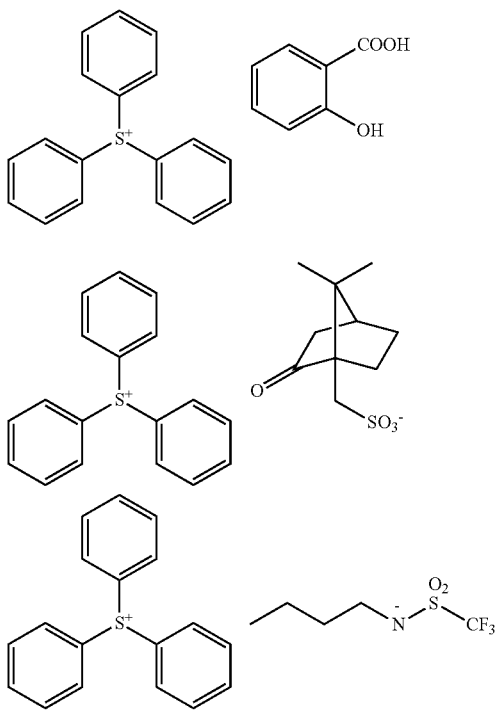

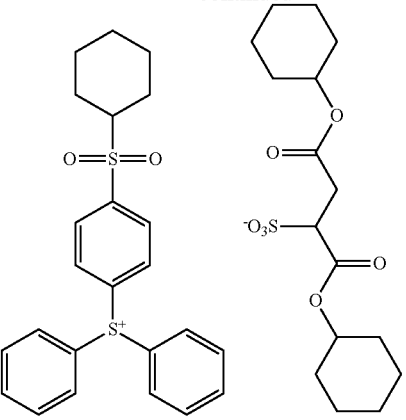

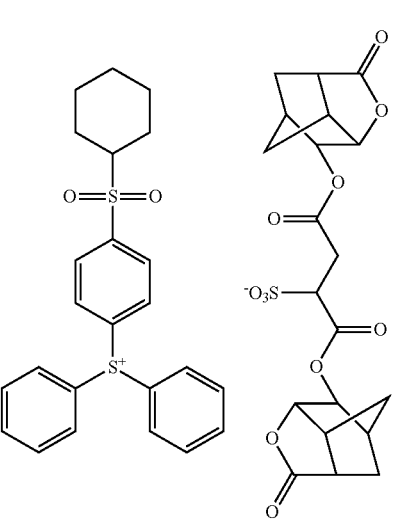

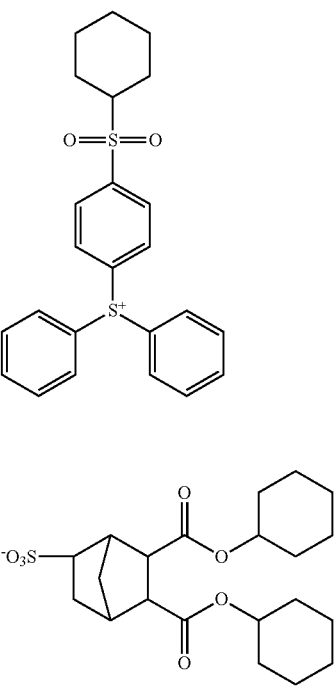

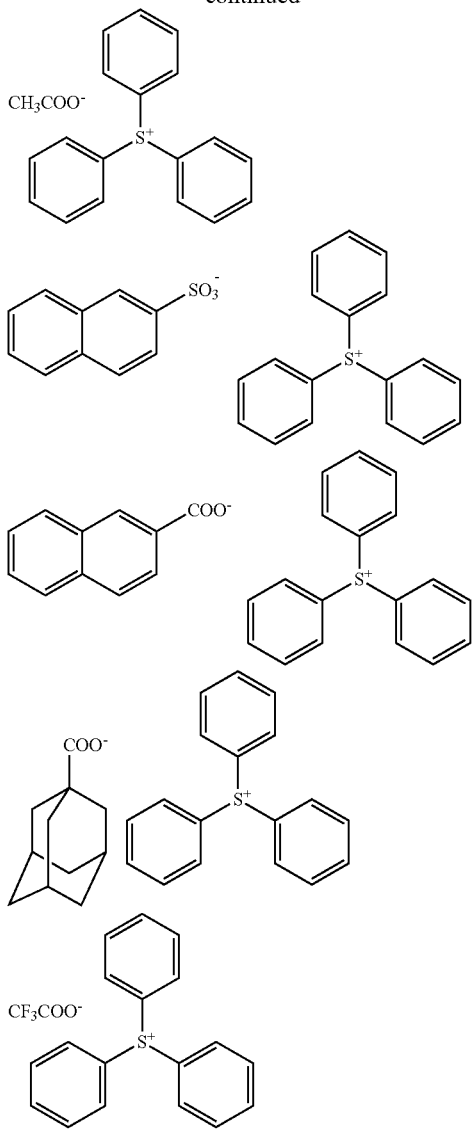

Of these, as the photodegradable base, a sulfonium salt is preferred, a triarylsulfonium salt is more preferred, and triphenylsulfonium salicylate and triphenylsulfonium 10-camphorsulfonate are still more preferred.

In the case of the acid diffusion controller (D) being (D) an acid diffusion control agent, the content of the acid diffusion controller (D) with respect to 100 parts by mass of the polymer (A) is preferably 0 parts by mass to 20 parts by mass, more preferably 0.1 parts by mass to 15 parts by mass, still more preferably 0.3 parts by mass to 10 parts by mass, and particularly preferably 0.5 parts by mass to 5 parts by mass. When the content of the acid diffusion control agent (D) is greater than the upper limit, the sensitivity of the radiation-sensitive resin composition may be deteriorated.

(E) Polymer

The polymer (E) is an acid-labile group-containing polymer (except for those corresponding to the polymer (A)). In the case of the polymer (A) not including an acid-labile group, the radiation-sensitive resin composition needs to contain the polymer (E). The polymer (E) preferably has a structural unit that includes an acid-labile group. Examples of the structural unit that includes an acid-labile group include structural units similar to those exemplified in connection with the structural unit (II) of the polymer (A), and the like.

The polymer (E) is exemplified by a polymer having the structural units (II) to (V) of the polymer (A) and other structural unit, and the like.

In the case of the polymer (A) not including the acid-labile group, the content of the polymer (E) with respect to 100 parts by mass of the polymer (A) is preferably 20 parts by mass to 200 parts by mass, and more preferably 50 parts by mass to 150 parts by mass.

(F) Polymer

The polymer (F) is a fluorine atom-containing polymer (except for those corresponding to the polymer (A)). When the radiation-sensitive resin composition according to the embodiment of the present invention contains the polymer (F), in forming a resist film, the polymer (F) tends to be unevenly distributed in the vicinity of the surface of the resist film due to oil repellent characteristics of the fluorine-containing polymer in the film, and thus elution of the acid generating agent, the acid diffusion control agent and the like into a liquid immersion medium can be inhibited during an exposure through the liquid immersion medium. In addition, due to water repellent characteristics of the polymer (F), an advancing contact angle of a liquid immersion medium on a resist film can be controlled to fall within a desired range, whereby formation of bubble defects can be inhibited. Furthermore, a larger receding contact angle of a liquid immersion medium on a resist film is attained, thereby enabling an exposure by high-speed scanning without being accompanied by residual water beads. Thus, when the radiation-sensitive resin composition contains the polymer (F), a resist film suitable for a liquid immersion lithography process can be formed.

The polymer (F) is not particularly limited as long as the polymer (F) contains a fluorine atom; however, it is preferred that the polymer (F) has a higher percentage content (% by mass) of fluorine atoms than that of the polymer (A) in the radiation-sensitive resin composition. When the polymer (F) has a higher percentage content of fluorine atoms than that of the polymer (A), a higher degree of the aforementioned uneven distribution is attained, leading to an improvement of characteristics such as water repellency and elution inhibitory ability of the resulting resist film.

The percentage content of fluorine atoms of the polymer (F) is preferably no less than 1% by mass, more preferably 2% by mass to 60% by mass, still more preferably 4% by mass to 40% by mass, and particularly preferably 7% by mass to 30% by mass. When the percentage content of fluorine atoms of the polymer (F) is less than lower limit, the hydrophobicity of the surface of the resist film may be deteriorated. It is to be noted that the percentage content (% by mass) of fluorine atoms of the polymer can be calculated based on the structure of the polymer determined by $^{13}$C-NMR spectroscopy.

The polymer (F) preferably has at least one selected from the group consisting of the following structural units (Fa) and (Fb). The polymer (F) may have each one, or two or more types of the structural unit (Fa) and/or the structural unit (Fb).

Structural Unit (Fa)

The structural unit (Fa) is represented by the following formula (6a). When the polymer (F) has the structural unit (Fa), the percentage content of fluorine atoms of the polymer (F) can be adjusted.

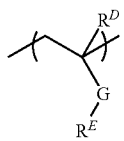

(6a)

In the above formula (6a), $R^D$ represents a hydrogen atom, a methyl group or a trifluoromethyl group; G represents a single bond, an oxygen atom, a sulfur atom, —CO—O—, —SO$_2$—O—NH—, —CO—NH— or —O—CO—NH—; $R^E$ represents a monovalent chain hydrocarbon group having 1 to 6 carbon atoms and at least one fluorine atom, or a monovalent aliphatic cyclic hydrocarbon group having 4 to 20 carbon atoms and at least one fluorine atom.

Examples of the chain hydrocarbon group having 1 to 6 carbon atoms and at least one fluorine atom, which may be represented by $R^E$, include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the aliphatic cyclic hydrocarbon group having 4 to 20 carbon atoms and at least one fluorine atom, which may be represented by $R^E$, include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of a monomer that gives the structural unit (Fa) include (meth)acrylic acid trifluoromethyl ester, (meth)acrylic acid 2,2,2-trifluoroethyl ester, (meth)acrylic acid 2,2,2-trifluoroethyloxycarbonylmethyl ester, (meth)acrylic acid perfluoroethyl ester, (meth)acrylic acid perfluoro-n-propyl ester, (meth)acrylic acid perfluoro-i-propyl ester, (meth)acrylic acid perfluoro-n-butyl ester, (meth)acrylic acid perfluoro-i-butyl ester, (meth)acrylic acid perfluoro-t-butyl ester, (meth)acrylic acid 2-(1,1,1,3,3,3-hexafluoropropyl) ester, (meth)acrylic acid 1-(2,2,3,3,4,4,5,5-octafluoropentyl) ester, (meth)acrylic acid perfluorocyclohexylmethyl ester, (meth)acrylic acid 1-(2,2,3,3,3-pentafluoropropyl) ester, (meth)acrylic acid monofluorocyclopentyl ester, (meth)acrylic acid difluorocyclopentyl ester, (meth)acrylic acid perfluorocyclopentyl ester, (meth)acrylic acid monofluorocyclohexyl ester, (meth)acrylic acid difluorocyclopentyl ester, (meth)acrylic acid perfluorocyclohexylmethyl ester, (meth)acrylic acid fluoronorbornyl ester, (meth)acrylic acid fluoroadamantyl ester, (meth)acrylic acid fluorobornyl ester, (meth)acrylic acid fluoroisobornyl ester, (meth)acrylic acid fluorotricyclodecyl ester, (meth)acrylic acid fluorotetracyclodecyl ester, and the like.

Of these, (meth)acrylic acid 2,2,2-trifluoroethyloxycarbonylmethyl ester is preferred.

The proportion of the structural unit (Fa) with respect to the total structural units constituting the polymer (F) is preferably 5 mol % to 95 mol %, more preferably 10 mol % to 90 mol %, and still more preferably 30 mol % to 85 mol %. When the proportion of the structural unit (Fa) falls within the above range, a larger dynamic contact angle can be achieved on the surface of the resist film in the exposure through a liquid immersion medium.

Structural Unit (Fb)

The structural unit (Fb) is represented by the following formula (6b). When the polymer (F) has the structural unit (Fb), the hydrophobicity thereof may be enhanced, leading to a further increase of a dynamic contact angle on the surface of the resist film formed from the radiation-sensitive resin composition.

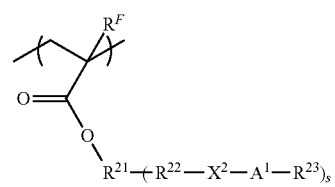

(6b)

In the above formula (6b), $R^F$ represents a hydrogen atom, a methyl group or a trifluoromethyl group; $R^{21}$ represents a hydrocarbon group having 1 to 20 carbon atoms and having a valency of (s+1), which may further include an oxygen atom, a sulfur atom, —NR'—, a carbonyl group, —CO—O— or —CO—NH-bound at an end of $R^{21}$ on the $R^{22}$ side; $R^1$ represents a hydrogen atom or a monovalent organic group; $R^{22}$ represents a single bond, a divalent chain hydrocarbon group having 1 to 10 carbon atoms or a divalent aliphatic cyclic hydrocarbon group having 4 to 20 carbon atoms; $X^2$ represents a divalent chain hydrocarbon group having 1 to 20 carbon atoms and at least one fluorine atom; $A^1$ represents an oxygen atom, —NR''—, —CO—O—* or —SO$_2$—O—*, wherein R'' represents a hydrogen atom or a monovalent organic group, and * denotes a binding site to $R^{21}$; $R^{23}$ represents a hydrogen atom or a monovalent organic group; and s is an integer of 1 to 3, wherein in a case where s is 2 or 3, a plurality of $R^{22}$s may be each identical or different, a plurality of $X^2$s may be each identical or different, a plurality of $A^1$s may be each identical or different and a plurality of $R^{23}$s may be each identical or different.

It is preferred that $R^{23}$ represents a hydrogen atom in light of the possibility of the improvement of the solubility of the polymer (F) in an alkaline developer solution.

Examples of the monovalent organic group which may be represented by $R^{23}$ include: hydrocarbon groups having 1 to 30 carbon atoms and optionally including an acid-labile group, an alkali-labile group or a substituent; and the like.

Examples of the structural unit (Fb) include structural units represented by the following formulae (6b-1) to (6b-3), and the like.

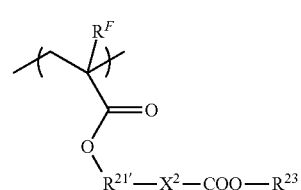

(6b-1)

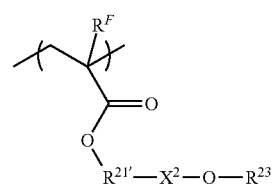

(6b-2)

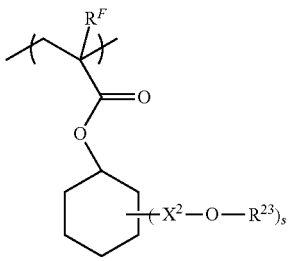
(6b-3)

In the above formulae (6b-1) to (6b-3), $R^{21'}$ represents a linear, branched or cyclic saturated or unsaturated hydrocarbon divalent group having 1 to 20 carbon atoms; and $R^F$, $X^2$, $R^{23}$ and s are as defined in the above formula (6b), wherein in a case where s is 2 or 3, a plurality of $X^2$s may be each identical or different, and a plurality of $R^{23}$s may be each identical or different.

The proportion of the structural unit (6b) with respect to the total structural units constituting the polymer (F) is preferably 0 mol % to 90 mol %, more preferably 5 mol % to 85 mol %, and still more preferably 10 mol % to 80 mol %. When the proportion of the structural unit (6b) falls within the above range, the degree of a decrease of a dynamic contact angle on the surface of the resist film formed from the radiation-sensitive resin composition in a development with an alkali may be increased.

Structural Unit (Fc)

The polymer (F) may have, in addition to the structural units (Fa) and (Fb), a structural unit that includes an acid-labile group (hereinafter, may be also referred to as "structural unit (Fc)") (except for those corresponding to the structural unit (Fb)). When the polymer (F) has the structural unit (Fc), the configuration of the resulting resist pattern may be more favorable. Examples of the structural unit (Fc) include the structural unit (II) mentioned hereinabove in connection with the polymer (A), and the like.

The proportion of the structural unit (Fc) with respect to the total structural units constituting the polymer (F) is preferably 5 mol % to 90 mol %, more preferably 10 mol % to 70 mol %, still more preferably 15 mol % to 60 mol %, and particularly preferably 15 mol % to 50 mol %. When the proportion of the structural unit (Fc) is less than the lower limit, formation of development defects in the resist pattern may not be sufficiently inhibited. When the proportion of the structural unit (Fc) is greater than the upper limit, the hydrophobicity of the surface of the resulting resist film may be decreased.

Other Structural Unit

Also, the polymer (F) may have, in addition to the aforementioned structural units, other structural unit, for example: a structural unit that includes an alkali-soluble group; a structural unit that includes at least one structure selected from the group consisting of a lactone structure, a cyclic carbonate structure and a sultone structure; a structural unit that includes an alicyclic group; and the like. Examples of the alkali-soluble group include a carboxy group, a sulfonamide group, a sulfo group, and the like. Examples of the structural unit that includes at least one structure selected from the group consisting of a lactone structure, a cyclic carbonate structure and a sultone structure include the structural unit (IV) mentioned hereinabove in connection with the polymer (A), and the like.

The proportion of the other structural unit with respect to the total structural units constituting the polymer (F) is typically no greater than 30 mol %, and preferably no greater than 20 mol %. When the proportion of the other structural unit is greater than the upper limit, the pattern formability of the radiation-sensitive resin composition may be deteriorated.

The content of the polymer (F) in the radiation-sensitive resin composition with respect to 100 parts by mass of the polymer (A) is preferably 0 to 20 parts by mass, more preferably 0.5 parts by mass to 15 parts by mass, and still more preferably 1 parts by mass to 10 parts by mass. When the content of the polymer (F) is greater than the upper limit, the pattern formability of the radiation-sensitive resin composition may be deteriorated.

Other Optional Components

The radiation-sensitive resin composition may contain other optional component in addition to the aforementioned components (A) to (F). Examples of the other optional component include an uneven distribution accelerator, a surfactant, an alicyclic skeleton-containing compound, a sensitizing agent, and the like. These other optional components each may be used either alone or in combination of two or more types thereof.

Uneven Distribution Accelerator

The uneven distribution accelerator exerts the effect of more efficiently segregating the polymer (F) on the surface of the resist film, for example, in a case where the radiation-sensitive resin composition contains the polymer (F). When the radiation-sensitive resin composition contains this uneven distribution accelerator, the amount of the polymer (F) added can be decreased than before. Therefore, elution of the component(s) from the resist film into a liquid immersion liquid is further inhibited, and quicker liquid immersion lithography is enabled by high-speed scanning, without impairing basic characteristics for use as a resist, in terms of, e.g., the LWR, the development defects and the pattern collapse resistance. As a result, the hydrophobicity of the surface of the resist film that prevents defects derived from liquid immersion such as watermark defects can be increased. As the uneven distribution accelerator, a low-molecular weight compound having a relative permittivity of no less than 30 and no greater than 200, and having a boiling point at 1 atmospheric pressure of no less than 100° C. may be used. Specifically, such a compound is exemplified by a lactone compound, a carbonate compound, a nitrile compound, a polyhydric alcohol, and the like.

Specific examples of the lactone compound include γ-butyrolactone, valerolactone, mevalonic lactone, norbornane-lactone, and the like.

Specific examples of the carbonate compound include propylene carbonate, ethylene carbonate, butylene carbonate, vinylene carbonate, and the like.

Specific examples of the nitrile compound include succinonitrile, and the like. Specific examples of the polyhydric alcohol include glycerin, and the like.

The content of the uneven distribution accelerator with respect to 100 parts by mass of the total amount of the polymer(s) in the radiation-sensitive resin composition is preferably 10 parts by mass to 500 parts by mass, and more preferably 30 to 300 parts by mass.

Surfactant

The surfactant exerts the effect of improving coating properties, striation, developability, and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; commercially available products such as KP341 (manufactured by Shin-Etsu Chemical Co., Ltd.), Polyflow No. 75 and Polyflow No. 95 (each manufactured by Kyoeisha Chemical Co., Ltd.), EFTOP EF301, EFTOP EF303 and EFTOP EF352 (each manufactured by Tochem Products Co. Ltd.), Megaface F171 and Megaface F173 (each manufactured by DIC), Fluorad FC430 and Fluorad FC431 (each manufactured by Sumitomo 3M Limited), ASAHI GUARD AG710, and Surflon S-382, Surflon SC-101, Surflon SC-102, Surflon SC-103, Surflon SC-104, Surflon SC-105 and Surflon SC-106 (each manufactured by Asahi Glass Co., Ltd.); and the like. The content of the surfactant in the radiation-sensitive resin composition is typically no greater than 2 parts by mass with respect to 100 parts by mass of the polymer (A).

Alicyclic Skeleton-Containing Compound

The alicyclic skeleton-containing compound exerts the effect of improving dry-etching resistance, a pattern configuration, adhesiveness to a substrate, and the like.

Sensitizing Agent

The sensitizing agent exhibits the action of increasing the amount of the acid produced from the acid generating agent (B) or the like, and exerts the effect of improving "apparent sensitivity" of the radiation-sensitive resin composition. Examples of the sensitizing agent include carbazoles, acetophenones, benzophenones, naphthalenes, phenols, biacetyl, eosin, rose bengal, pyrenes, anthracenes, phenothiazines, and the like. These sensitizing agents may be used either alone, or two or more types thereof may be used in combination. The content of the sensitizing agent in the radiation-sensitive resin composition is typically no greater than 2 parts by mass with respect to 100 parts by mass of the polymer (A).

Preparation Method of Radiation-Sensitive Resin Composition

The radiation-sensitive resin composition may be prepared, for example, by mixing the polymer (A) and the acid generator (B), as well as the acid diffusion control agent (D), the polymer (E), the polymer (F) and the optional component which are contained as needed, with the organic solvent (C) in a certain ratio. After the mixing, the radiation-sensitive resin composition is preferably filtered through a filter with a pore size of about 0.2 µm, for example. The solid content concentration of the radiation-sensitive resin composition is typically 0.1% by mass to 50% by mass, preferably 0.5% by mass to 30% by mass, and more preferably 1% by mass to 20% by mass.

The radiation-sensitive resin composition may be used for positive-pattern formation in which an alkaline developer solution is employed, and negative-pattern formation in which a developer solution that contains an organic solvent is employed. Of these, when used in the negative-pattern formation in which a developer solution that contains an organic solvent is employed, the radiation-sensitive resin composition can attain a higher resolution.

Resist Pattern-Forming Method

A resist pattern-forming method according to another embodiment of the present invention includes:

providing a resist film by using the radiation-sensitive resin composition according to the embodiment of the present invention (hereinafter, may be also referred to as "resist film-providing step");

exposing the resist film (hereinafter, may be also referred to as "exposure step"); and developing the exposed resist film (hereinafter, may be also referred to as "development step").

According to the resist pattern-forming method, since the radiation-sensitive resin composition described above is used, a resist pattern exhibiting a small LWR, a high resolution, and superior rectangularity of the cross-sectional shape can be formed while a great depth of focus EL is exhibited. Hereinafter, each step will be explained.

Resist Film-Providing Step

In this step, a resist film is provided using the radiation-sensitive resin composition. The substrate on which the resist film is provided may be exemplified by a conventionally well-known substrate such as a silicon wafer and a wafer coated with silicon dioxide or aluminum, and the like. In addition, an organic or inorganic antireflective film disclosed in, for example, Japanese Examined Patent Application, Publication No. H6-12452, Japanese Unexamined Patent Application, Publication No. S59-93448, or the like may be provided on the substrate. An application method is exemplified by spin coat (spin-coating), cast coating, roll coating, and the like. After the application, prebaking (PB) may be executed as needed for allowing a solvent in the coating film to be evaporated. The temperature for PB is typically 60° C. to 140° C., and preferably 80° C. to 120° C. The time period for PB is typically 5 sec to 600 sec, and preferably 10 sec to 300 sec. The film thickness of the resist film provided is preferably 10 nm to 1,000 nm, and more preferably 10 nm to 500 nm.

In order to prevent influences of basic impurities etc., included in the environment atmosphere, a protective film may be provided on the resist film, as disclosed in, for example, Japanese Unexamined Patent Application, Publication No. H5-188598, or the like. Furthermore, in order to prevent an outflow of the acid generator or the like from the resist film, a protective film for liquid immersion may be provided on the resist film, as disclosed in, for example, Japanese Unexamined Patent Application, Publication No. 2005-352384, or the like. It is to be noted that these techniques may be used in combination.

Exposure Step

In this step, the resist film provided in the resist film-providing step is exposed by irradiating the resist film with exposure light through a photomask (through a liquid immersion medium such as water, as needed). Examples of the exposure light include: electromagnetic waves such as visible light rays, ultraviolet rays, far ultraviolet rays, extreme ultraviolet rays (13.5 nm, EUV), X-rays and γ-rays; charged particle rays such as electron beams and α-rays; and the like, in accordance with the line width of the intended pattern. Of these, far ultraviolet rays, EUV, and electron beams are preferred, an ArF excimer laser beam (wavelength: 193 nm), a KrF excimer laser beam (wavelength: 248 nm), EUV, and electron beams are more preferred, and an ArF excimer laser beam and EUV, electron beams are still more preferred.

In a case where the exposure is executed through a liquid immersion liquid, examples of the liquid immersion liquid for use in the exposure include water, fluorine-containing inert liquids, and the like. It is preferred that the liquid immersion liquid is transparent to an exposure wavelength, and has a temperature coefficient of the refractive index as small as possible so that distortion of an optical image projected onto the film is minimized. In particular, when an ArF excimer laser beam (wavelength: 193 nm) is used as an exposure light source, it is preferred to use water in light of availability and ease of handling thereof in addition to the aforementioned considerations. When water is used, a slight amount of an additive which reduces the surface tension of water and imparts enhanced surfactant power may be added.

It is preferred that the additive hardly dissolves a resist film on a wafer and has a negligible influence on an optical coating of an inferior face of a lens. The water for use is preferably distilled water.

It is preferred that post exposure baking (PEB) is carried out after the exposure to promote dissociation of the acid-labile group included in the polymer (A), etc. mediated by the acid generated from the acid generator (B) upon the exposure at exposed sites of the resist film. This PEB produces a difference in the solubility of the resist film in a developer solution between the light-exposed sites and light-unexposed sites. The temperature for PEB is typically 50° C. to 180° C., and preferably 80° C. to 130° C. The time period for PEB is typically 5 sec to 600 sec, and preferably 10 sec to 300 sec.

Development Step

In this step, the resist film exposed in the exposure step is developed using a developer solution. This permits a predetermined resist pattern to be formed. Examples of the developer solution include alkaline developer solutions, developer solutions that contain an organic solvent, and the like. The developer solution may be selected in accordance with a pattern configuration to be formed. A positive resist pattern can be formed by projecting a mask pattern on the resist film upon an exposure, developing with an aqueous alkaline solution, a region irradiated with a greater irradiation light intensity, and thereby dissolving and removing a light-exposed site corresponding to a given threshold value or greater. On the other hand, a negative resist pattern can be formed by projecting a mask pattern on the resist film upon an exposure, developing a region irradiated with a lower irradiation light intensity with a liquid that contains an organic solvent, and thereby dissolving and removing a light-exposed site corresponding to a given threshold value or lower. The development may be carried out by using these developer solutions in combination in accordance with a desired resolution and/or pattern configuration.

Examples of the alkaline developer solution include aqueous alkaline solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene and 1,5-diazabicyclo-[4.3.0]-5-nonene, and the like.

Examples of the organic solvent which may be contained in the organic solvent-containing developer solution described above include one, or two or more types of the solvents exemplified in connection with the organic solvent (C) of the aforementioned radiation-sensitive resin composition, and the like. Of these, the ether solvent, the ester solvent and the ketone solvent are preferred. The ether solvent is preferably an aromatic group-containing ether solvent, and more preferably anisole.

The ester solvent is preferably an acetic acid ester solvent, and more preferably n-butyl acetate. The ketone solvent is preferably a chain ketone solvent, and more preferably 2-heptanone.

The content of the organic solvent in the developer solution is preferably no less than 80% by mass, more preferably no less than 90% by mass, still more preferably no less than 95% by mass, and particularly preferably no less than 99% by mass. When the content of the organic solvent in the developer solution falls within the above range, a contrast between the light-exposed site and the light-unexposed site can be improved, and consequently a resist pattern exhibiting a smaller LWR and CDU can be formed while a greater EL is exhibited. It is to be noted that a component other than the organic solvent is exemplified by water, silicon oil, and the like.

A surfactant may be added to the developer solution in an appropriate amount as needed. As the surfactant, for example, an ionic or nonionic fluorochemical surfactant and/or silicon surfactant, and the like may be used.

Examples of the development method include: a dipping method in which the substrate is immersed for a given time period in the developer solution charged in a container; a puddle method in which the developer solution is placed to form a dome-shaped bead by way of the surface tension on the surface of the substrate for a given time period to conduct a development; a spraying method in which the developer solution is sprayed onto the surface of the substrate; a dynamic dispensing method in which the developer solution is continuously applied onto the substrate that is rotated at a constant speed while scanning with a developer solution-application nozzle at a constant speed; and the like.

After the development, rinsing is preferably conducted using a rinse agent such as water and alcohol, followed by drying. The method for the rinsing is exemplified by: a spin-coating method in which the rinse agent is continuously applied onto the substrate that is rotated at a constant speed; a dipping method in which the substrate is immersed for a given time period in the rinse agent charged in a container; a spraying method in which the rinse agent is sprayed onto the surface of the substrate; and the like.

EXAMPLES

Hereinafter, the present invention is explained in detail by way of Examples, but the present invention is not in any way limited to these Examples. Measuring methods for various types of physical properties are shown below.

Weight Average Molecular Weight (Mw), Number Average Molecular Weight (Mn) and Dispersity Index (Mw/Mn)

The Mw and the Mn of the polymer were determined by gel permeation chromatography (GPC) using GPC columns (G2000 HXL×2, G3000 HXL×1, and G4000 HXL×1; manufactured by Tosoh Corporation), a differential refractometer as a detector, and mono-dispersed polystyrene as a standard under analytical conditions involving a flow rate of 1.0 mL/min, an elution solvent of tetrahydrofuran, a sample concentration of 1.0% by mass, an amount of injected sample of 100 μL, and a column temperature of 40° C. Moreover, the dispersity index (Mw/Mn) was calculated based on the results of the determination of the Mw and the Mn.

Content of Low-Molecular Weight Matter

The content (% by mass) of the low-molecular weight matter (i.e., matter having a molecular weight of no greater than 1,000) in the polymer (A) was determined by high performance liquid chromatography (HPLC) using an HPLC column (Intersil ODS-25 μm, 4.6 mmϕ×250 mm) manufactured by GL Sciences, Inc., under the following conditions:

elution solvent: acrylonitrile/0.1% by mass aqueous phosphoric acid solution;

flow rate: 1.0 mL/min;

sample concentration: 1.0% by mass;

amount of injected sample: 100 μL; and detector: differential refractometer.

13C-NMR Analysis

13C-NMR analysis for determining the proportion (mol %) of each structural unit contained in the polymer was carried out using a nuclear magnetic resonance apparatus (JNM-ECX400, manufactured by JEOL, Ltd.) and deuterochloroform as a solvent for measurement.

Synthesis of Compound

Synthesis Example 1: Synthesis of Compound (M-1)

A compound represented by the following formula (M-1) was synthesized in accordance with the following reaction scheme.

Into a 500 mL eggplant-shaped flask were charged 9.21 g (55.5 mmol) of 3-bromopyruvic acid, 10.6 g (55.5 mmol) of 1-ethyl-3-[3-(dimethylamino)propyl]carbodiimide hydrochloride (EDCI), 6.78 g (55.5 mmol) of dimethylaminopyridine (DMAP) and 150 mL of dichloromethane as a solvent, and then the mixture was stirred. To this, 50 mL of a solution of 5.67 g (55.5 mmol) of 3-hydroxy-γ-butyrolactone in dichloromethane was slowly added dropwise at room temperature. After stirring at room temperature for 48 hrs, the reaction was stopped using dilute hydrochloric acid, and then the dichloromethane phase was collected. After concentration, purification by column chromatography was conducted to obtain 9.89 g (yield: 71%) of a 3-bromopyruvic acid ester product.

Subsequently, 30.0 g of tetrahydrofuran and 20.0 g of water were added as a solvent to 5.0 g (19.9 mmol) of the 3-bromopyruvic acid ester product obtained above and 4.30 g (39.8 mmol) of sodium methacrylate, and the mixture was stirred at 60° C. for 20 hrs. After washed by liquid separation, the mixture was concentrated and purified by column chromatography to obtain 3.47 g (yield: 68%) of a compound (M-1).

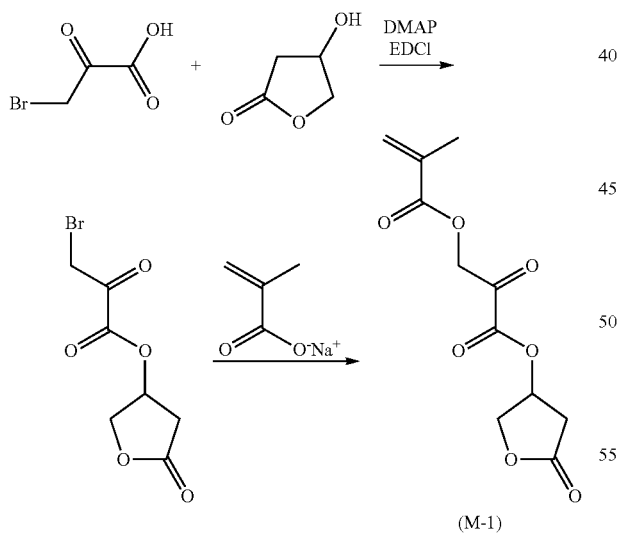

(M-1)

Synthesis Examples 2 to 39: Synthesis of Compounds (M-2) to (M-39)

Compounds represented by the following formulae (M-2) to (M-39) were synthesized by appropriately selecting a precursor and conducting an operation similar to that of Example 1.

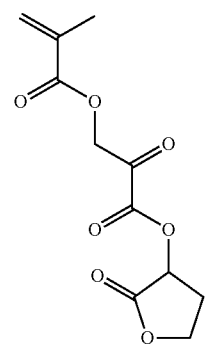

(M-2)

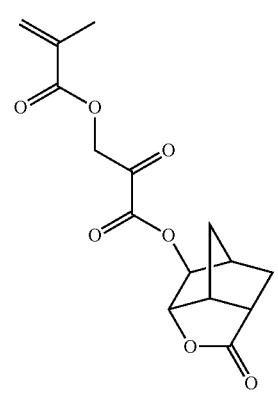

(M-3)

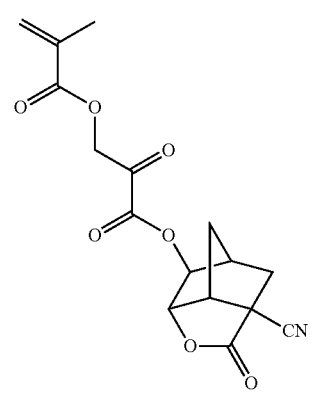

(M-4)

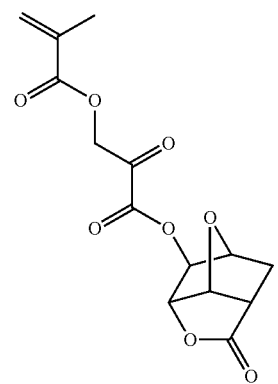

(M-5)

(M-6) 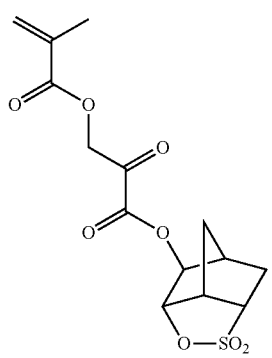
(M-7) 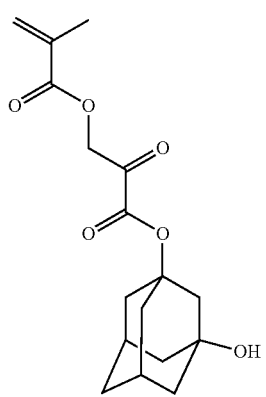
(M-8) 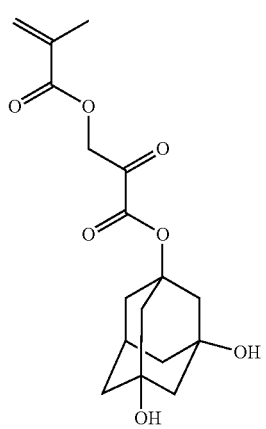
(M-9) 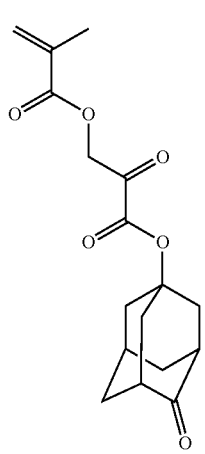
(M-10) 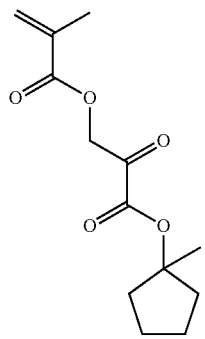
(M-11) 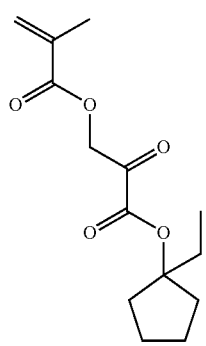
(M-12) 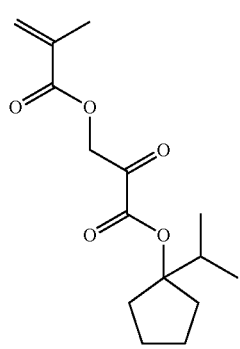
(M-13) 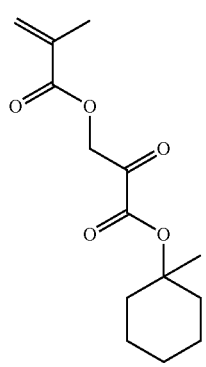

(M-14) 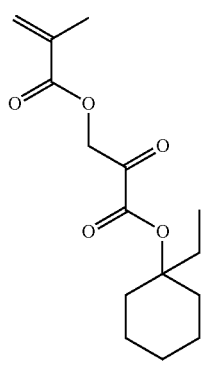
(M-15) 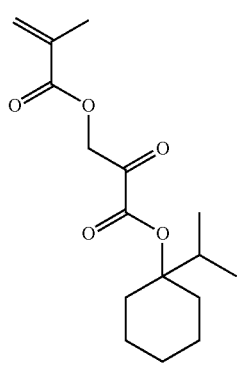
(M-16) 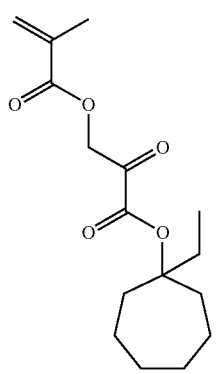
(M-17) 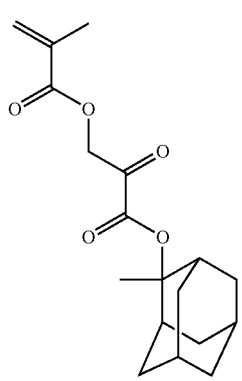
(M-18) 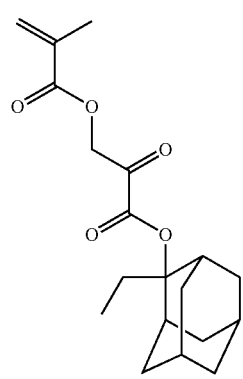
(M-19) 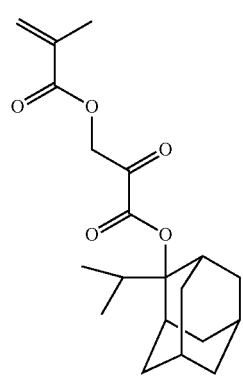
(M-20) 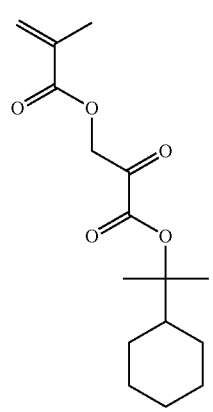
(M-21) 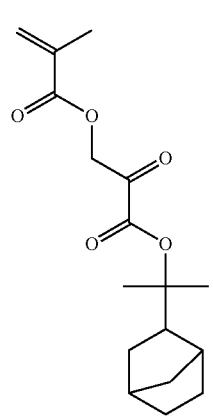

(M-22)
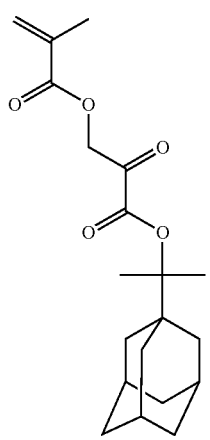
(M-23)
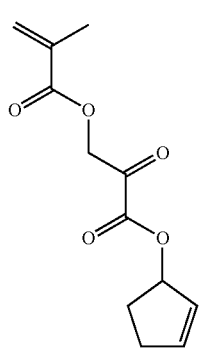
(M-24)
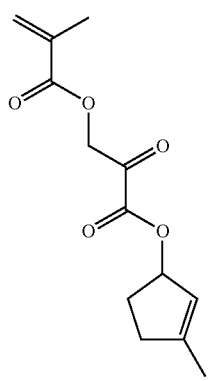
(M-25)
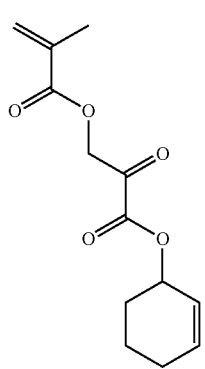
(M-26)
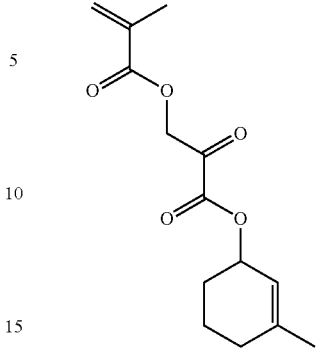
(M-27)
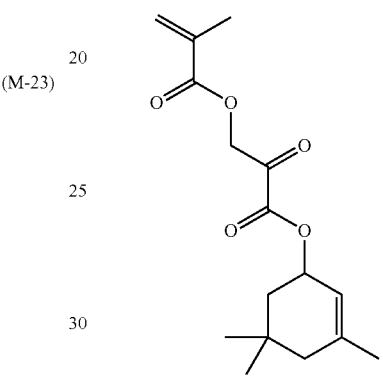
(M-28)
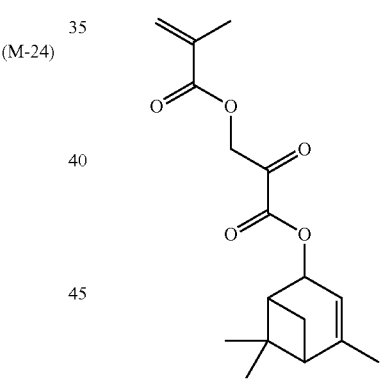
(M-29)
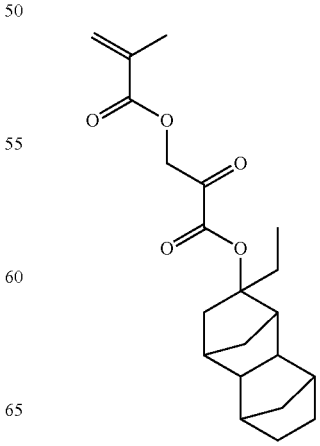

(M-30)
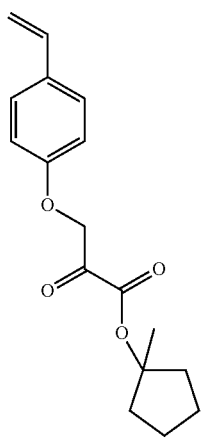
(M-31)
(M-32)
(M-33)
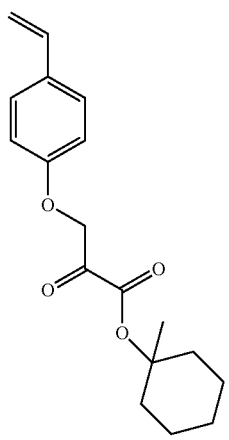
(M-34)
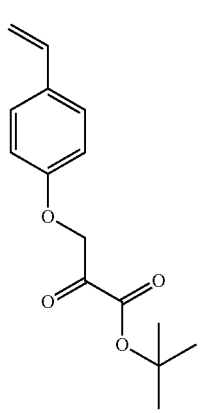
(M-35)
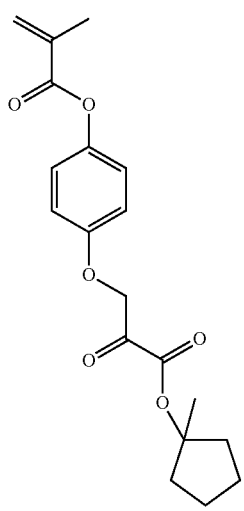

(M-36) 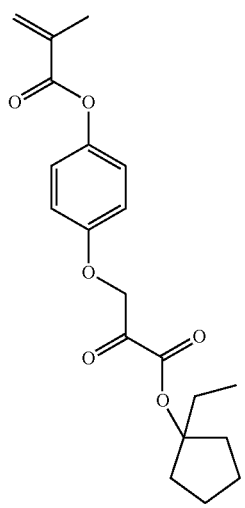
(M-37) 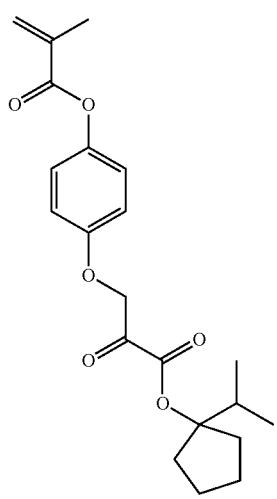
(M-38) 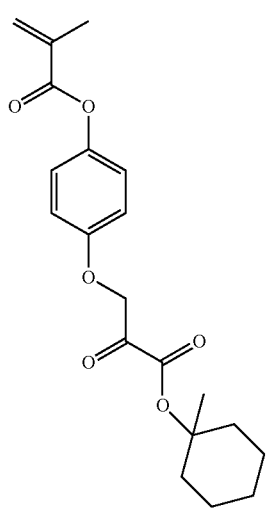
(M-39) 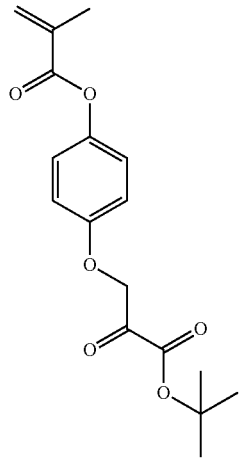
Synthesis of Polymer
Monomers which were used in the synthesis of polymers and are other than the aforementioned monomers are shown below.
(M-40) 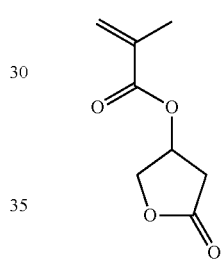
(M-41) 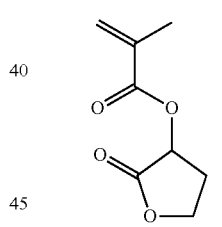
(M-42) 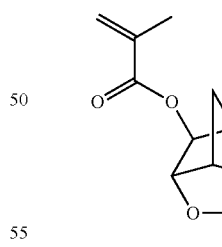
(M-43) 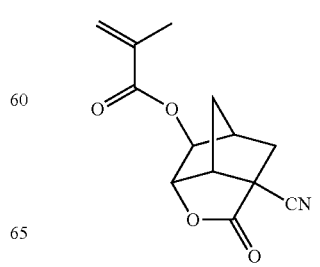

(M-44) 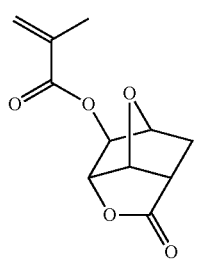
(M-45) 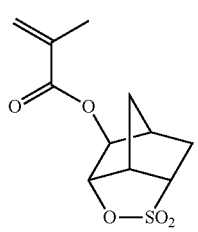
(M-46) 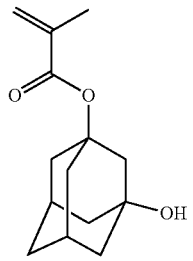
(M-47) 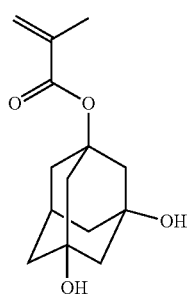
(M-48) 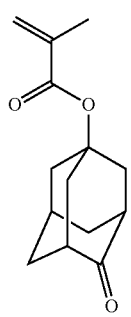
(M-49) 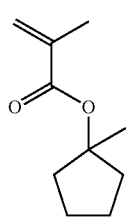
(M-50) 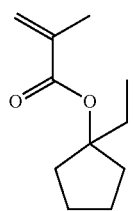
(M-51) 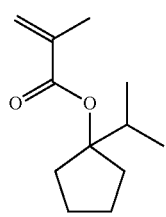
(M-52) 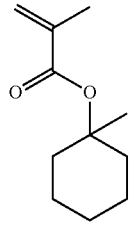
(M-53) 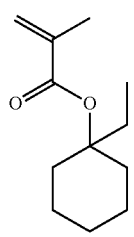
(M-54) 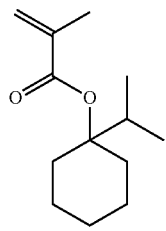
(M-55) 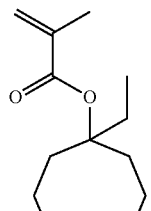
(M-56) 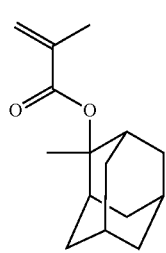

(M-57) 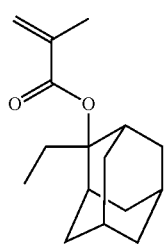
(M-58) 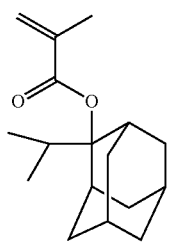
(M-59) 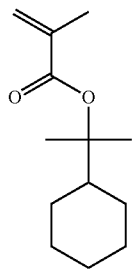
(M-60) 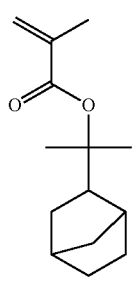
(M-61) 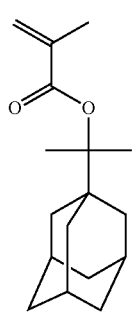
(M-62) 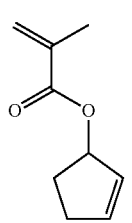
(M-63) 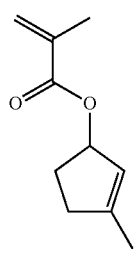
(M-64) 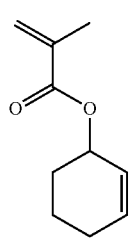
(M-65) 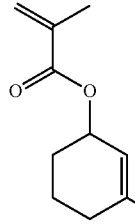
(M-66) 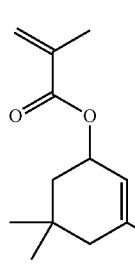
(M-67) 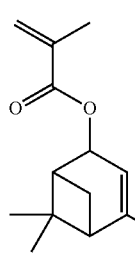
(M-68) 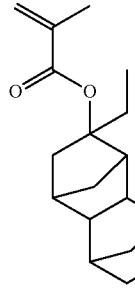

-continued (M-69)
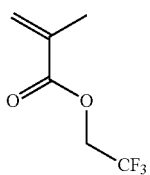

(M-70)
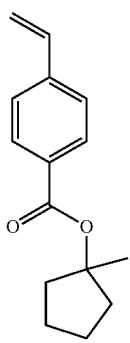

(M-71)
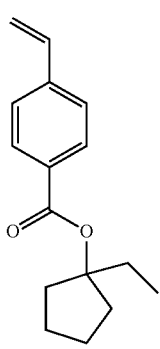

(M-72)
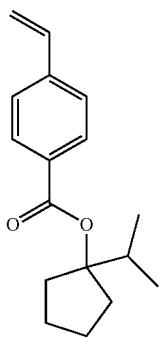

(M-73)
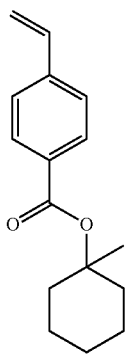

-continued (M-74)
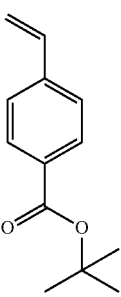

(M-75)

(M-76)
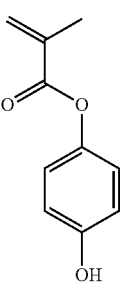

Synthesis of Polymer (A), (1)

Example 1: Synthesis of Polymer (A-1)

A monomer solution was prepared by dissolving 10.08 g (40 mol %) of the compound (M-1) and 9.92 g (60 mol %) of the compound (M-49) in 40 g of 2-butanone, and further adding thereto 0.81 g (5 mol % with respect to the total number of moles of the compounds) of AIBN as a radical polymerization initiator. Next, a 100 mL three-neck flask containing 20 g of 2-butanone was purged with a nitrogen gas for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. The cooled polymerization reaction solution was poured into 400 g of methanol, and a precipitated white powder was filtered off. The collected white powder washed twice with 80 g of methanol, followed by filtration, and dried at 50° C. for 17 hrs to obtain a polymer (A-1) as a white powder (14.8 g; yield: 74%). The polymer (A-1) had an Mw of 7,300, and an Mw/Mn of 1.53, and the content of the low-molecular weight matter was 0.04% by mass. The result of $^{13}$C-NMR analysis indicated that the proportions of the structural unit derived from (M-1) and the structural unit derived from (M-49) were 39.7 mol % and 60.3 mol %, respectively.

Examples 2 to 9, 10 and 16 to 18, and Synthesis Examples 40 to 99 and 105 to 107: Synthesis of Polymers (A-2) to (A-37) and (A-43) to (A-45), and Polymers (a-1) to (a-33) and (a-39) to (a-41)

Polymers (A-2) to (A-37) and (A-43) to (A-45), and (a-1) to (a-33) and (a-39) to (a-41) were each synthesized by a similar operation to Example 1 except that the type and the amount of the monomers used were as shown in Tables 1 and 2. Values of the yield (%), the Mw, the Mw/Mn and the content of the low-molecular weight matter (% by mass) of each polymer obtained are shown together in Tables 1 and 2 below.

Synthesis of Polymer (A), (2)

Example 11: Synthesis of Polymer (A-38)

After 55.0 g (50 mol %) of the compound (M-30) and 31.0 g (50 mol %) of the compound (M-75), 4 g of AIBN as a radical initiator, and 1 g of t-dodecyl mercaptan were dissolved in 100 g of propylene glycol monomethyl ether, the mixture was subjected to copolymerization for 6 hrs under a nitrogen atmosphere, while the reaction temperature was maintained at 70° C. After the completion of the polymerization reaction, the polymerization reaction solution was added dropwise to 1,000 g of n-hexane to permit solidification purification of a polymer. Next, to the polymer was added 150 g of propylene glycol monomethyl ether again, and then 150 g of methanol, 34 g of triethylamine and 6 g of water were further added. The mixture was subjected to a hydrolysis reaction for 8 hrs while refluxing at a boiling point. After the completion of the reaction, the solvent and triethylamine were distilled off in vacuo, the obtained polymer was dissolved in 150 g of acetone, which was then added dropwise to 2,000 g of water to permit solidification, and the generated white powder was filtered off and was dried at 50° C. for 17 hrs to obtain a polymer (A-38) as a white powder (50.6 g; yield: 65%). The polymer (A-38) had an Mw of 6,500, and an Mw/Mn of 1.62. The result of $^{13}$C-NMR analysis indicated that the proportions of the structural unit derived from (M-30) and the structural unit derived from p-hydroxystyrene were 49.7 mol % and 50.3 mol %, respectively.

Examples 12 to 15 and Synthesis Examples 100 to 104: Synthesis of Polymers (A-39) to (A-42) and Polymers (a-34) to (a-38)

Polymers (A-39) to (A-42) and polymers (a-34) to (a-38) were synthesized by a similar operation to Example 11 except that the monomers shown in Tables 1-1 1-2, 2-1, and 2-1 were used.

TABLE 1-1

|  | (A) Polymer | Monomer that gives structural unit (I) | | | Monomer that gives structural units (II) to (V) | | | | | | |
|---|---|---|---|---|---|---|---|---|---|---|---|
|  |  | type | amount (mol %) | proportion of structural unit (mol %) | type | amount (mol %) | proportion of structural unit (mol %) | Yield (%) | Mw | Mw/Mn | Content of low-molecular weight matter (% by mass) |
| Example 1 | A-1 | M-1 | 40 | 39.7 | M-49 | 60 | 60.3 | 74 | 7,300 | 1.53 | 0.04 |
| Example 2 | A-2 | M-2 | 40 | 39.9 | M-49 | 60 | 60.1 | 72 | 7,000 | 1.53 | 0.05 |
| Example 3 | A-3 | M-3 | 40 | 40.1 | M-49 | 60 | 59.9 | 74 | 7,100 | 1.52 | 0.04 |
| Example 4 | A-4 | M-4 | 40 | 39.7 | M-49 | 60 | 60.3 | 71 | 7,100 | 1.53 | 0.05 |
| Example 5 | A-5 | M-5 | 40 | 39.8 | M-49 | 60 | 60.2 | 70 | 7,000 | 1.52 | 0.04 |
| Example 6 | A-6 | M-6 | 40 | 39.9 | M-49 | 60 | 60.1 | 72 | 7,200 | 1.54 | 0.05 |
| Example 7 | A-7 | M-7 | 40 | 40.2 | M-49 | 60 | 59.8 | 71 | 7,200 | 1.54 | 0.07 |
| Example 8 | A-8 | M-8 | 40 | 40.3 | M-49 | 60 | 59.7 | 79 | 7,100 | 1.53 | 0.04 |
| Example 9 | A-9 | M-9 | 40 | 39.9 | M-49 | 60 | 60.1 | 74 | 7,100 | 1.53 | 0.04 |
| Synthesis Example 40 | A-10 | M-10 | 60 | 60.1 | M-42 | 40 | 39.9 | 76 | 7,100 | 1.52 | 0.04 |
| Synthesis Example 41 | A-11 | M-11 | 60 | 59.9 | M-42 | 40 | 40.1 | 71 | 7,100 | 1.53 | 0.05 |
| Synthesis Example 42 | A-12 | M-12 | 60 | 60.4 | M-42 | 40 | 39.6 | 73 | 7,000 | 1.54 | 0.04 |
| Synthesis Example 43 | A-13 | M-13 | 60 | 60.3 | M-42 | 40 | 39.7 | 72 | 7,000 | 1.53 | 0.05 |
| Synthesis Example 44 | A-14 | M-14 | 60 | 59.8 | M-42 | 40 | 40.2 | 73 | 7,100 | 1.51 | 0.04 |
| Synthesis Example 45 | A-15 | M-15 | 60 | 59.6 | M-42 | 40 | 40.4 | 70 | 7,200 | 1.51 | 0.04 |
| Synthesis Example 46 | A-16 | M-16 | 60 | 60.2 | M-42 | 40 | 39.8 | 74 | 7,100 | 1.52 | 0.04 |
| Synthesis Example 47 | A-17 | M-17 | 60 | 60.1 | M-42 | 40 | 39.9 | 77 | 7,000 | 1.53 | 0.05 |
| Synthesis Example 48 | A-18 | M-18 | 60 | 59.9 | M-42 | 40 | 40.1 | 74 | 7,100 | 1.54 | 0.04 |
| Synthesis Example 49 | A-19 | M-19 | 60 | 59.7 | M-42 | 40 | 40.3 | 75 | 7,200 | 1.58 | 0.05 |
| Synthesis Example 50 | A-20 | M-20 | 60 | 60.2 | M-42 | 40 | 39.8 | 70 | 7,200 | 1.55 | 0.04 |
| Synthesis Example 51 | A-21 | M-21 | 60 | 60.2 | M-42 | 40 | 39.8 | 70 | 7,200 | 1.52 | 0.04 |
| Synthesis Example 52 | A-22 | M-22 | 60 | 59.7 | M-42 | 40 | 40.3 | 71 | 7,000 | 1.52 | 0.05 |
| Synthesis Example 53 | A-23 | M-23 | 60 | 59.8 | M-42 | 40 | 40.2 | 75 | 7,000 | 1.52 | 0.05 |
| Synthesis Example 54 | A-24 | M-24 | 60 | 60.3 | M-42 | 40 | 39.7 | 77 | 7,500 | 1.55 | 0.05 |
| Synthesis Example 55 | A-25 | M-25 | 60 | 60.1 | M-42 | 40 | 39.9 | 74 | 7,100 | 1.54 | 0.04 |

TABLE 1-2

|  | (A) Polymer | Monomer that gives structural unit (I) | | | Monomer that gives structural units (II) to (V) | | | | | | |
|---|---|---|---|---|---|---|---|---|---|---|---|
|  |  | type | amount (mol %) | proportion of structural unit (mol %) | type | amount (mol %) | proportion of structural unit (mol %) | Yield (%) | Mw | Mw/Mn | Content of low-molecular weight matter (% by mass) |
| Synthesis Example 56 | A-26 | M-26 | 60 | 59.8 | M-42 | 40 | 40.2 | 76 | 7,100 | 1.53 | 0.04 |
| Synthesis Example 57 | A-27 | M-27 | 60 | 59.7 | M-42 | 40 | 40.3 | 71 | 7,000 | 1.51 | 0.04 |

TABLE 1-2-continued

| | (A) Polymer | Monomer that gives structural unit (I) | | | Monomer that gives structural units (II) to (V) | | | Yield (%) | Mw | Mw/Mn | Content of low-molecular weight matter (% by mass) |
|---|---|---|---|---|---|---|---|---|---|---|---|
| | | type | amount (mol %) | proportion of structural unit (mol %) | type | amount (mol %) | proportion of structural unit (mol %) | | | | |
| Synthesis Example 58 | A-28 | M-28 | 60 | 60.1 | M-42 | 40 | 39.9 | 73 | 7,200 | 1.51 | 0.05 |
| Synthesis Example 59 | A-29 | M-29 | 60 | 60.1 | M-42 | 40 | 39.9 | 72 | 7,100 | 1.52 | 0.04 |
| Synthesis Example 60 | A-30 | M-35 | 60 | 53.6 | M-42 | 40 | 46.4 | 71 | 7,200 | 1.61 | 0.04 |
| Synthesis Example 61 | A-31 | M-36 | 60 | 52.4 | M-42 | 40 | 47.6 | 68 | 7,300 | 1.58 | 0.03 |
| Synthesis Example 62 | A-32 | M-37 | 60 | 51.3 | M-42 | 40 | 48.7 | 68 | 7,200 | 1.62 | 0.04 |
| Synthesis Example 63 | A-33 | M-38 | 60 | 52.4 | M-42 | 40 | 47.6 | 70 | 7,200 | 1.61 | 0.03 |
| Synthesis Example 64 | A-34 | M-39 | 60 | 48.5 | M-42 | 40 | 51.5 | 71 | 7,200 | 1.52 | 0.04 |
| Synthesis Example 65 | A-35 | M-19 | 50 | 49.8 | M-43 | 40 | 40.1 | 74 | 7,200 | 1.53 | 0.04 |
| | | | | | M-47 | 10 | 10.1 | | | | |
| Synthesis Example 66 | A-36 | M-22 | 55 | 55.2 | M-42 | 35 | 35.2 | 69 | 7,100 | 1.52 | 0.04 |
| | | | | | M-57 | 10 | 9.6 | | | | |
| Example 10 | A-37 | M-1 | 55 | 54.7 | M-49 | 45 | 45.3 | 74 | 7,200 | 1.53 | 0.04 |
| Example 11 | A-38 | M-30 | 50 | 49.7 | M-75 | 50 | 50.3 | 65 | 6,500 | 1.62 | 0.05 |
| Example 12 | A-39 | M-31 | 40 | 39.2 | M-75 | 60 | 60.8 | 62 | 6,600 | 1.68 | 0.05 |
| Example 13 | A-40 | M-32 | 40 | 39.7 | M-75 | 60 | 60.3 | 60 | 6,200 | 1.59 | 0.06 |
| Example 14 | A-41 | M-33 | 40 | 40.1 | M-75 | 60 | 59.9 | 66 | 6,500 | 1.63 | 0.05 |
| Example 15 | A-42 | M-34 | 50 | 49.1 | M-75 | 50 | 50.9 | 61 | 6,500 | 1.67 | 0.06 |
| Example 16 | A-43 | M-31 | 50 | 48.7 | M-76 | 50 | 51.3 | 69 | 7,000 | 1.54 | 0.04 |
| Example 17 | A-44 | M-32 | 50 | 49.2 | M-76 | 50 | 50.8 | 71 | 7,100 | 1.53 | 0.04 |
| Example 18 | A-45 | M-33 | 50 | 49.0 | M-76 | 50 | 51.0 | 68 | 7,000 | 1.51 | 0.04 |

TABLE 2-1

| | (A) Component | Monomer that gives structural unit (II) | | | Monomer that gives structural units (III) to (V) and other structural unit | | | Yield (%) | Mw | Mw/Mn | Content of low-molecular weight matter (% by mass) |
|---|---|---|---|---|---|---|---|---|---|---|---|
| | | type | amount (mol %) | proportion of structural unit (mol %) | type | amount (mol %) | proportion of structural unit (mol %) | | | | |
| Synthesis Example 67 | a-1 | M-49 | 60 | 59.9 | M-40 | 40 | 40.1 | 70 | 7,200 | 1.53 | 0.05 |
| Synthesis Example 68 | a-2 | M-49 | 60 | 59.6 | M-41 | 40 | 40.4 | 72 | 7,100 | 1.54 | 0.04 |
| Synthesis Example 69 | a-3 | M-49 | 60 | 60.2 | M-42 | 40 | 39.8 | 70 | 7,000 | 1.58 | 0.04 |
| Synthesis Example 70 | a-4 | M-49 | 60 | 60.1 | M-43 | 40 | 39.9 | 79 | 7,100 | 1.55 | 0.04 |
| Synthesis Example 71 | a-5 | M-49 | 60 | 59.9 | M-44 | 40 | 40.1 | 74 | 7,000 | 1.53 | 0.05 |
| Synthesis Example 72 | a-6 | M-49 | 60 | 59.7 | M-45 | 40 | 40.3 | 76 | 7,100 | 1.51 | 0.04 |
| Synthesis Example 73 | a-7 | M-49 | 60 | 60.2 | M-46 | 40 | 39.8 | 71 | 7,200 | 1.51 | 0.04 |
| Synthesis Example 74 | a-8 | M-49 | 60 | 60.2 | M-47 | 40 | 39.8 | 73 | 7,200 | 1.52 | 0.04 |
| Synthesis Example 75 | a-9 | M-49 | 60 | 59.7 | M-48 | 40 | 40.3 | 74 | 7,200 | 1.53 | 0.05 |
| Synthesis Example 76 | a-10 | M-50 | 60 | 59.8 | M-42 | 40 | 40.2 | 76 | 7,000 | 1.54 | 0.04 |
| Synthesis Example 77 | a-11 | M-51 | 60 | 60.3 | M-42 | 40 | 39.7 | 71 | 7,000 | 1.58 | 0.04 |
| Synthesis Example 78 | a-12 | M-52 | 60 | 60.1 | M-42 | 40 | 39.9 | 73 | 7,500 | 1.55 | 0.04 |
| Synthesis Example 79 | a-13 | M-53 | 60 | 59.8 | M-42 | 40 | 40.2 | 72 | 7,100 | 1.52 | 0.04 |
| Synthesis Example 80 | a-14 | M-54 | 60 | 60.3 | M-42 | 40 | 39.7 | 73 | 7,100 | 1.52 | 0.05 |
| Synthesis Example 81 | a-15 | M-55 | 60 | 60.1 | M-42 | 40 | 39.9 | 74 | 7,000 | 1.54 | 0.04 |
| Synthesis Example 82 | a-16 | M-56 | 60 | 59.8 | M-42 | 40 | 40.2 | 75 | 7,000 | 1.53 | 0.05 |
| Synthesis Example 83 | a-17 | M-57 | 60 | 59.7 | M-42 | 40 | 40.3 | 70 | 7,000 | 1.51 | 0.04 |
| Synthesis Example 84 | a-18 | M-58 | 60 | 60.1 | M-42 | 40 | 39.9 | 70 | 7,200 | 1.51 | 0.04 |
| Synthesis Example 85 | a-19 | M-59 | 60 | 60.1 | M-42 | 40 | 39.9 | 71 | 7,200 | 1.52 | 0.05 |
| Synthesis Example 86 | a-20 | M-60 | 60 | 59.9 | M-42 | 40 | 40.1 | 75 | 7,100 | 1.53 | 0.05 |
| Synthesis Example 87 | a-21 | M-61 | 60 | 59.6 | M-42 | 40 | 40.4 | 74 | 7,100 | 1.54 | 0.05 |
| Synthesis Example 88 | a-22 | M-62 | 60 | 60.2 | M-42 | 40 | 39.8 | 76 | 7,100 | 1.58 | 0.04 |
| Synthesis Example 89 | a-23 | M-63 | 60 | 60.1 | M-42 | 40 | 39.9 | 71 | 7,100 | 1.55 | 0.04 |
| Synthesis Example 90 | a-24 | M-64 | 60 | 59.8 | M-42 | 40 | 40.2 | 73 | 7,000 | 1.53 | 0.04 |

TABLE 2-2

| | (A) Component | Monomer that gives structural unit (II) | | | Monomer that gives structural units (III) to (V) and other structural unit | | | Yield (%) | Mw | Mw/Mn | Content of low-molecular weight matter (% by mass) |
|---|---|---|---|---|---|---|---|---|---|---|---|
| | | type | amount (mol %) | proportion of structural unit (mol %) | type | amount (mol %) | proportion of structural unit (mol %) | | | | |
| Synthesis Example 91 | a-25 | M-65 | 60 | 59.6 | M-42 | 40 | 40.4 | 74 | 7,000 | 1.51 | 0.05 |
| Synthesis Example 92 | a-26 | M-66 | 60 | 60.2 | M-42 | 40 | 39.8 | 72 | 7,100 | 1.51 | 0.04 |

TABLE 2-2-continued

| (A) Component | Monomer that gives structural unit (II) | | | Monomer that gives structural units (III) to (V) and other structural unit | | | Yield (%) | Mw | Mw/Mn | Content of low-molecular weight matter (% by mass) |
|---|---|---|---|---|---|---|---|---|---|---|
| | type | amount (mol %) | proportion of structural unit (mol %) | type | amount (mol %) | proportion of structural unit (mol %) | | | | |
| Synthesis Example 93 | a-27 | M-67 | 60 | 60.1 | M-42 | 40 | 39.9 | 74 | 7,100 | 1.53 | 0.05 |
| Synthesis Example 94 | a-28 | M-68 | 60 | 59.9 | M-42 | 40 | 40.1 | 71 | 7,000 | 1.51 | 0.04 |
| Synthesis Example 95 | a-29 | M-70 | 60 | 59.8 | M-42 | 40 | 40.2 | 73 | 7,000 | 1.53 | 0.04 |
| Synthesis Example 96 | a-30 | M-71 | 60 | 59.6 | M-42 | 40 | 40.4 | 74 | 7,000 | 1.51 | 0.05 |
| Synthesis Example 97 | a-31 | M-72 | 60 | 60.2 | M-42 | 40 | 39.8 | 72 | 7,100 | 1.51 | 0.04 |
| Synthesis Example 98 | a-32 | M-73 | 60 | 60.1 | M-42 | 40 | 39.9 | 74 | 7,100 | 1.53 | 0.05 |
| Synthesis Example 99 | a-33 | M-74 | 60 | 59.9 | M-42 | 40 | 40.1 | 71 | 7,000 | 1.51 | 0.04 |
| Synthesis Example 100 | a-34 | M-70 | 50 | 49.1 | M-75 | 50 | 50.9 | 71 | 7,200 | 1.58 | 0.04 |
| Synthesis Example 101 | a-35 | M-71 | 40 | 39.4 | M-75 | 60 | 60.6 | 68 | 7,200 | 1.55 | 0.04 |
| Synthesis Example 102 | a-36 | M-72 | 40 | 39.1 | M-75 | 60 | 60.9 | 68 | 7,000 | 1.52 | 0.04 |
| Synthesis Example 103 | a-37 | M-73 | 40 | 39.8 | M-75 | 60 | 60.2 | 70 | 7,100 | 1.52 | 0.05 |
| Synthesis Example 104 | a-38 | M-74 | 50 | 49.2 | M-75 | 50 | 50.8 | 71 | 7,200 | 1.52 | 0.04 |
| Synthesis Example 105 | a-39 | M-71 | 50 | 49.1 | M-76 | 50 | 50.9 | 68 | 7,200 | 1.55 | 0.04 |
| Synthesis Example 106 | a-40 | M-72 | 50 | 49.5 | M-76 | 50 | 50.5 | 68 | 7,100 | 1.54 | 0.05 |
| Synthesis Example 107 | a-41 | M-73 | 50 | 49.2 | M-76 | 50 | 50.8 | 69 | 7,200 | 1.53 | 0.04 |

Synthesis of Polymer (F)

Synthesis Example 108: Synthesis of Polymer (F-1)

A monomer solution was prepared by dissolving 79.9 g (70 mol %) of the compound (M-56) and 20.91 g (30 mol %) of the compound (M-75) in 100 g of 2-butanone, and further dissolving therein 4.77 g of dimethyl 2,2'-azobisisobutyrate as a radical polymerization initiator. Next, a 1,000 mL three-neck flask containing 100 g of 2-butanone was purged with a nitrogen gas for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. This polymerization reaction solution was transferred to a 2 L separatory funnel, and homogeneously diluted with 150 g of n-hexane. After the addition of 600 g of methanol, the components were mixed. Then, after the addition of 30 g of distilled water, the mixture was further stirred, and then allowed to stand for 30 min. Thereafter, the lower layer was collected to obtain a propylene glycol monomethyl ether acetate solution containing a polymer (F-1) (yield: 60%). The polymer (F-1) had an Mw of 7,200, and an Mw/Mn of 2.00. The result of $^{13}$C-NMR analysis indicated that the proportions of the structural unit derived from (M-56) and the structural unit derived from (M-75) were 71.1 mol % and 28.9 mol %, respectively.

Preparation of Radiation-Sensitive Resin Compositions

The acid generating agent (B), the organic solvent (C), the acid diffusion control agent (D) and the uneven distribution accelerator (G) which were used in the preparation of the radiation-sensitive resin compositions are shown below.

(B) Acid Generating Agent

B-1: triphenylsulfonium 2-(adamantan-1-ylcarbonyloxy)-1,1,3,3,3-pentafluoropropane-1-sulfonate (a compound represented by the following formula (B-1))

B-2: triphenylsulfonium norbornanesulton-2-yloxycarbonyl difluoromethanesulfonate (a compound represented by the following formula (B-2))

B-3: triphenylsulfonium 3-(N-piperidinesulfonyl)-1,1,2,2,3,3-hexafluoropropane-1-sulfonate (a compound represented by the following formula (B-3))

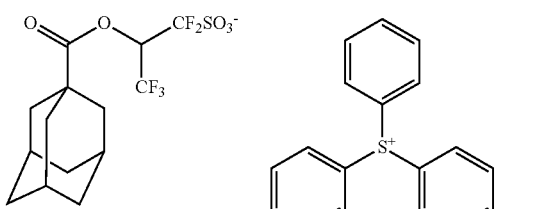

(B-1)

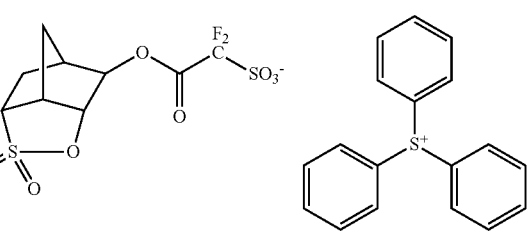

(B-2)

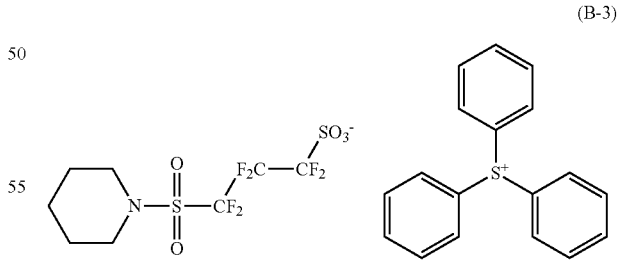

(B-3)

(C) Organic Solvent

C-1: propylene glycol monomethyl ether acetate

C-2: cyclohexanone (D) Acid Diffusion Control Agent

D-1: triphenylsulfonium salicylate (a compound represented by the following formula (D-1))

D-2: triphenylsulfonium 10-camphorsulfonate (a compound represented by the following formula (D-2))

D-3: N-(undecan-1-ylcarbonyloxyethyl)morpholine (a compound represented by the following formula (D-3))

D-4: 2,6-isopropylaniline (a compound represented by the following formula (D-4))

D-5: tri-n-pentylamine (a compound represented by the following formula (D-5))

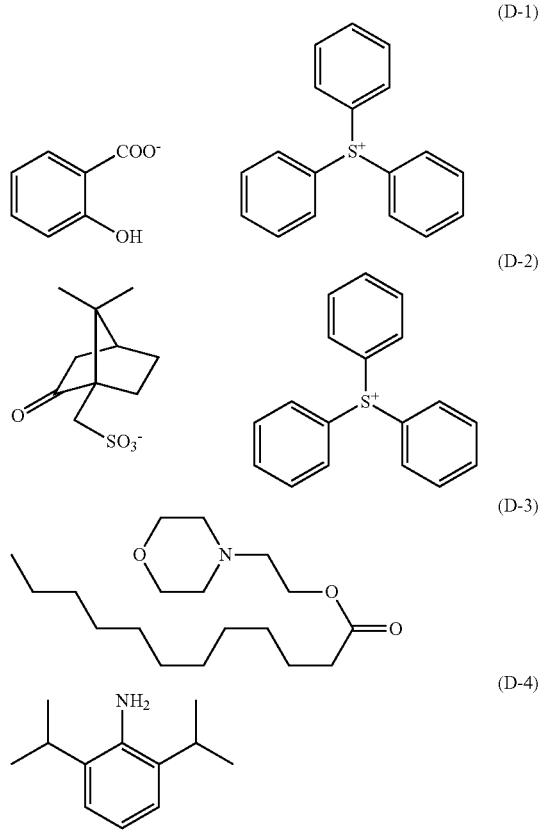

(D-1)

(D-2)

(D-3)

(D-4)

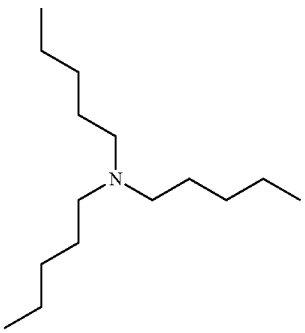

(D-5)

(G) Uneven Distribution Accelerator

G-1: γ-butyrolactone

Example 19

A radiation-sensitive resin composition (J-1) was prepared by mixing 100 parts by mass of (A-1) as the polymer (A), 8.5 parts by mass of (B-1) as the acid generating agent (B), 2,240 parts by mass of (C-1) and 960 parts by mass of (C-2) as the organic solvent (C), 2.3 parts by mass of (D-1) as the acid diffusion control agent (D), 3 parts by mass of (F-1) as the polymer (F), and 30 parts by mass of (G-1) as the uneven distribution accelerator (G).

Examples 20 to 63 and Comparative Examples 1 to 41

Radiation-sensitive resin compositions (J-2) to (J-45) and (CJ-1) to (CJ-41) were prepared by a similar operation to Example 19 except that the type and the amount of each component used were as specified in Tables 3-1, 3-2, 4-1, 4-2, and 4-3 below.

TABLE 3-1

| | Radiation-sensitive resin composition | (A) Polymer type | (A) Polymer amount (parts by mass) | (B) Acid generating agent type | (B) Acid generating agent amount (parts by mass) | (C) Organic solvent type | (C) Organic solvent amount (parts by mass) | (D) Acid diffusion control agent type | (D) Acid diffusion control agent amount (parts by mass) | (F) Polymer type | (F) Polymer amount (parts by mass) | (G) Uneven distribution accelerator type | (G) Uneven distribution accelerator amount (parts by mass) |
|---|---|---|---|---|---|---|---|---|---|---|---|---|---|
| Example 19 | J-1 | A-1 | 100 | B-1 | 8.5 | C-1/C-2 | 2,240/960 | D-1 | 2.3 | F-1 | 3 | G-1 | 30 |
| Example 20 | J-2 | A-2 | 100 | B-2 | 8.5 | C-1/C-2 | 2,240/960 | D-1 | 2.3 | F-1 | 3 | G-1 | 30 |
| Example 21 | J-3 | A-3 | 100 | B-3 | 8.5 | C-1/C-2 | 2,240/960 | D-1 | 2.3 | F-1 | 3 | G-1 | 30 |
| Example 22 | J-4 | A-4 | 100 | B-1 | 8.5 | C-1/C-2 | 2,240/960 | D-1 | 2.3 | F-1 | 3 | G-1 | 30 |
| Example 23 | J-5 | A-5 | 100 | B-2 | 8.5 | C-1/C-2 | 2,240/960 | D-1 | 2.3 | F-1 | 3 | G-1 | 30 |
| Example 24 | J-6 | A-6 | 100 | B-3 | 8.5 | C-1/C-2 | 2,240/960 | D-1 | 2.3 | F-1 | 3 | G-1 | 30 |
| Example 25 | J-7 | A-7 | 100 | B-1 | 8.5 | C-1/C-2 | 2,240/960 | D-2 | 2.3 | F-1 | 3 | G-1 | 30 |
| Example 26 | J-8 | A-8 | 100 | B-2 | 8.5 | C-1/C-2 | 2,240/960 | D-2 | 2.3 | F-1 | 3 | G-1 | 30 |
| Example 27 | J-9 | A-9 | 100 | B-3 | 8.5 | C-1/C-2 | 2,240/960 | D-2 | 2.3 | F-1 | 3 | G-1 | 30 |
| Example 28 | J-10 | A-10 | 100 | B-3 | 8.5 | C-1/C-2 | 2,240/960 | D-1 | 2.3 | F-1 | 3 | G-1 | 30 |
| Example 29 | J-11 | A-11 | 100 | B-2 | 8.5 | C-1/C-2 | 2,240/960 | D-2 | 2.3 | F-1 | 3 | G-1 | 30 |
| Example 30 | J-12 | A-12 | 100 | B-3 | 8.5 | C-1/C-2 | 2,240/960 | D-2 | 2.3 | F-1 | 3 | G-1 | 30 |
| Example 31 | J-13 | A-13 | 100 | B-1 | 8.5 | C-1/C-2 | 2,240/960 | D-3 | 2.3 | F-1 | 3 | G-1 | 30 |
| Example 32 | J-14 | A-14 | 100 | B-2 | 8.5 | C-1/C-2 | 2,240/960 | D-3 | 2.3 | F-1 | 3 | G-1 | 30 |
| Example 33 | J-15 | A-15 | 100 | B-3 | 8.5 | C-1/C-2 | 2,240/960 | D-3 | 2.3 | F-1 | 3 | G-1 | 30 |
| Example 34 | J-16 | A-16 | 100 | B-1 | 8.5 | C-1/C-2 | 2,240/960 | D-3 | 2.3 | F-1 | 3 | G-1 | 30 |
| Example 35 | J-17 | A-17 | 100 | B-2 | 8.5 | C-1/C-2 | 2,240/960 | D-3 | 2.3 | F-1 | 3 | G-1 | 30 |
| Example 36 | J-18 | A-18 | 100 | B-3 | 8.5 | C-1/C-2 | 2,240/960 | D-3 | 2.3 | F-1 | 3 | G-1 | 30 |
| Example 37 | J-19 | A-19 | 100 | B-1 | 8.5 | C-1/C-2 | 2,240/960 | D-4 | 2.3 | F-1 | 3 | G-1 | 30 |
| Example 38 | J-20 | A-20 | 100 | B-2 | 8.5 | C-1/C-2 | 2,240/960 | D-4 | 2.3 | F-1 | 3 | G-1 | 30 |

TABLE 3-1-continued

| | Radiation-sensitive resin composition | (A) Polymer type | amount (parts by mass) | (B) Acid generating agent type | amount (parts by mass) | (C) Organic solvent type | amount (parts by mass) | (D) Acid diffusion control agent type | amount (parts by mass) | (F) Polymer type | amount (parts by mass) | (G) Uneven distribution accelerator type | amount (parts by mass) |
|---|---|---|---|---|---|---|---|---|---|---|---|---|---|
| Example 39 | J-21 | A-21 | 100 | B-3 | 8.5 | C-1/C-2 | 2,240/960 | D-4 | 2.3 | F-1 | 3 | G-1 | 30 |
| Example 40 | J-22 | A-22 | 100 | B-1 | 8.5 | C-1/C-2 | 2,240/960 | D-4 | 2.3 | F-1 | 3 | G-1 | 30 |

TABLE 3-2

| | Radiation-sensitive resin composition | (A) Polymer type | amount (parts by mass) | (B) Acid generating agent type | amount (parts by mass) | (C) Organic solvent type | amount (parts by mass) | (D) Acid diffusion control agent type | amount (parts by mass) | (F) Polymer type | amount (parts by mass) | (G) Uneven distribution accelerator type | amount (parts by mass) |
|---|---|---|---|---|---|---|---|---|---|---|---|---|---|
| Example 41 | J-23 | A-23 | 100 | B-2 | 8.5 | C-1/C-2 | 2,240/960 | D-4 | 2.3 | F-1 | 3 | G-1 | 30 |
| Example 42 | J-24 | A-24 | 100 | B-3 | 8.5 | C-1/C-2 | 2,240/960 | D-4 | 2.3 | F-1 | 3 | G-1 | 30 |
| Example 43 | J-25 | A-25 | 100 | B-1 | 8.5 | C-1/C-2 | 2,240/960 | D-5 | 2.3 | F-1 | 3 | G-1 | 30 |
| Example 44 | J-26 | A-26 | 100 | B-2 | 8.5 | C-1/C-2 | 2,240/960 | D-5 | 2.3 | F-1 | 3 | G-1 | 30 |
| Example 45 | J-27 | A-27 | 100 | B-3 | 8.5 | C-1/C-2 | 2,240/960 | D-5 | 2.3 | F-1 | 3 | G-1 | 30 |
| Example 46 | J-28 | A-28 | 100 | B-1 | 8.5 | C-1/C-2 | 2,240/960 | D-5 | 2.3 | F-1 | 3 | G-1 | 30 |
| Example 47 | J-29 | A-29 | 100 | B-2 | 8.5 | C-1/C-2 | 2,240/960 | D-5 | 2.3 | F-1 | 3 | G-1 | 30 |
| Example 48 | J-30 | A-30 | 100 | B-1 | 8.5 | C-1/C-2 | 2,240/960 | D-2 | 2.3 | — | — | — | — |
| Example 49 | J-31 | A-31 | 100 | B-2 | 8.5 | C-1/C-2 | 2,240/960 | D-2 | 2.3 | — | — | — | — |
| Example 50 | J-32 | A-32 | 100 | B-2 | 8.5 | C-1/C-2 | 2,240/960 | D-2 | 2.3 | — | — | — | — |
| Example 51 | J-33 | A-33 | 100 | B-1 | 8.5 | C-1/C-2 | 2,240/960 | D-2 | 2.3 | — | — | — | — |
| Example 52 | J-34 | A-34 | 100 | B-1 | 8.5 | C-1/C-2 | 2,240/960 | D-2 | 2.3 | — | — | — | — |
| Example 53 | J-35 | A-35 | 100 | B-1 | 8.5 | C-1/C-2 | 2,240/960 | D-3 | 2.3 | F-1 | 3 | G-1 | 30 |
| Example 54 | J-36 | A-36 | 100 | B-1 | 8.5 | C-1/C-2 | 2,240/960 | D-4 | 2.3 | F-1 | 3 | G-1 | 30 |
| Example 55 | J-37 | A-37 | 100 | B-1 | 8.5 | C-1/C-2 | 2,240/960 | D-1 | 2.3 | F-1 | 3 | G-1 | 30 |
| Example 56 | J-38 | A-38 | 100 | B-1 | 8.5 | C-1/C-2 | 2,240/960 | D-1 | 2.3 | — | — | — | — |
| Example 57 | J-39 | A-39 | 100 | B-2 | 8.5 | C-1/C-2 | 2,240/960 | D-1 | 2.3 | — | — | — | — |
| Example 58 | J-40 | A-40 | 100 | B-2 | 8.5 | C-1/C-2 | 2,240/960 | D-1 | 2.3 | — | — | — | — |
| Example 59 | J-41 | A-41 | 100 | B-1 | 8.5 | C-1/C-2 | 2,240/960 | D-1 | 2.3 | — | — | — | — |
| Example 60 | J-42 | A-42 | 100 | B-1 | 8.5 | C-1/C-2 | 2,240/960 | D-1 | 2.3 | — | — | — | — |
| Example 61 | J-43 | A-43 | 100 | B-2 | 8.5 | C-1/C-2 | 2,240/960 | D-1 | 2.3 | — | — | — | — |
| Example 62 | J-44 | A-44 | 100 | B-2 | 8.5 | C-1/C-2 | 2,240/960 | D-1 | 2.3 | — | — | — | — |
| Example 63 | J-45 | A-45 | 100 | B-1 | 8.5 | C-1/C-2 | 2,240/960 | D-1 | 2.3 | — | — | — | — |

TABLE 4-1

| | Radiation-sensitive resin composition | (A) Component type | amount (parts by mass) | (B) Acid generating agent type | amount (parts by mass) | (C) Organic solvent type | amount (parts by mass) | (D) Acid diffusion control agent type | amount (parts by mass) | (F) Polymer type | amount (parts by mass) | (G) Uneven distribution accelerator type | amount (parts by mass) |
|---|---|---|---|---|---|---|---|---|---|---|---|---|---|
| Comparative Example 1 | CJ-1 | a-1 | 100 | B-1 | 8.5 | C-1/C-2 | 2,240/960 | D-1 | 2.3 | F-1 | 3 | G-1 | 30 |
| Comparative Example 2 | CJ-2 | a-2 | 100 | B-2 | 8.5 | C-1/C-2 | 2,240/960 | D-1 | 2.3 | F-1 | 3 | G-1 | 30 |
| Comparative Example 3 | CJ-3 | a-3 | 100 | B-3 | 8.5 | C-1/C-2 | 2,240/960 | D-1 | 2.3 | F-1 | 3 | G-1 | 30 |
| Comparative Example 4 | CJ-4 | a-4 | 100 | B-1 | 8.5 | C-1/C-2 | 2,240/960 | D-1 | 2.3 | F-1 | 3 | G-1 | 30 |
| Comparative Example 5 | CJ-5 | a-5 | 100 | B-2 | 8.5 | C-1/C-2 | 2,240/960 | D-1 | 2.3 | F-1 | 3 | G-1 | 30 |
| Comparative Example 6 | CJ-6 | a-6 | 100 | B-3 | 8.5 | C-1/C-2 | 2,240/960 | D-1 | 2.3 | F-1 | 3 | G-1 | 30 |
| Comparative Example 7 | CJ-7 | a-7 | 100 | B-1 | 8.5 | C-1/C-2 | 2,240/960 | D-2 | 2.3 | F-1 | 3 | G-1 | 30 |
| Comparative Example 8 | CJ-8 | a-8 | 100 | B-2 | 8.5 | C-1/C-2 | 2,240/960 | D-2 | 2.3 | F-1 | 3 | G-1 | 30 |
| Comparative Example 9 | CJ-9 | a-9 | 100 | B-3 | 8.5 | C-1/C-2 | 2,240/960 | D-2 | 2.3 | F-1 | 3 | G-1 | 30 |
| Comparative Example 10 | CJ-10 | a-10 | 100 | B-2 | 8.5 | C-1/C-2 | 2,240/960 | D-2 | 2.3 | F-1 | 3 | G-1 | 30 |

TABLE 4-1-continued

| | Radiation-sensitive resin composition | (A) Component type | (A) Component amount (parts by mass) | (B) Acid generating agent type | (B) Acid generating agent amount (parts by mass) | (C) Organic solvent type | (C) Organic solvent amount (parts by mass) | (D) Acid diffusion control agent type | (D) Acid diffusion control agent amount (parts by mass) | (F) Polymer type | (F) Polymer amount (parts by mass) | (G) Uneven distribution accelerator type | (G) Uneven distribution accelerator amount (parts by mass) |
|---|---|---|---|---|---|---|---|---|---|---|---|---|---|
| Comparative Example 11 | CJ-11 | a-11 | 100 | B-3 | 8.5 | C-1/C-2 | 2,240/960 | D-2 | 2.3 | F-1 | 3 | G-1 | 30 |
| Comparative Example 12 | CJ-12 | a-12 | 100 | B-1 | 8.5 | C-1/C-2 | 2,240/960 | D-2 | 2.3 | F-1 | 3 | G-1 | 30 |
| Comparative Example 13 | CJ-13 | a-13 | 100 | B-2 | 8.5 | C-1/C-2 | 2,240/960 | D-3 | 2.3 | F-1 | 3 | G-1 | 30 |

TABLE 4-2

| | Radiation-sensitive resin composition | (A) Component type | (A) Component amount (parts by mass) | (B) Acid generating agent type | (B) Acid generating agent amount (parts by mass) | (C) Organic solvent type | (C) Organic solvent amount (parts by mass) | (D) Acid diffusion control agent type | (D) Acid diffusion control agent amount (parts by mass) | (F) Polymer type | (F) Polymer amount (parts by mass) | (G) Uneven distribution accelerator type | (G) Uneven distribution accelerator amount (parts by mass) |
|---|---|---|---|---|---|---|---|---|---|---|---|---|---|
| Comparative Example 14 | CJ-14 | a-14 | 100 | B-3 | 8.5 | C-1/C-2 | 2,240/960 | D-3 | 2.3 | F-1 | 3 | G-1 | 30 |
| Comparative Example 15 | CJ-15 | a-15 | 100 | B-1 | 8.5 | C-1/C-2 | 2,240/960 | D-3 | 2.3 | F-1 | 3 | G-1 | 30 |
| Comparative Example 16 | CJ-16 | a-16 | 100 | B-2 | 8.5 | C-1/C-2 | 2,240/960 | D-3 | 2.3 | F-1 | 3 | G-1 | 30 |
| Comparative Example 17 | CJ-17 | a-17 | 100 | B-3 | 8.5 | C-1/C-2 | 2,240/960 | D-3 | 2.3 | F-1 | 3 | G-1 | 30 |
| Comparative Example 18 | CJ-18 | a-18 | 100 | B-1 | 8.5 | C-1/C-2 | 2,240/960 | D-3 | 2.3 | F-1 | 3 | G-1 | 30 |
| Comparative Example 19 | CJ-19 | a-19 | 100 | B-2 | 8.5 | C-1/C-2 | 2,240/960 | D-4 | 2.3 | F-1 | 3 | G-1 | 30 |
| Comparative Example 20 | CJ-20 | a-20 | 100 | B-3 | 8.5 | C-1/C-2 | 2,240/960 | D-4 | 2.3 | F-1 | 3 | G-1 | 30 |
| Comparative Example 21 | CJ-21 | a-21 | 100 | B-1 | 8.5 | C-1/C-2 | 2,240/960 | D-4 | 2.3 | F-1 | 3 | G-1 | 30 |
| Comparative Example 22 | CJ-22 | a-22 | 100 | B-2 | 8.5 | C-1/C-2 | 2,240/960 | D-4 | 2.3 | F-1 | 3 | G-1 | 30 |
| Comparative Example 23 | CJ-23 | a-23 | 100 | B-3 | 8.5 | C-1/C-2 | 2,240/960 | D-4 | 2.3 | F-1 | 3 | G-1 | 30 |
| Comparative Example 24 | CJ-24 | a-24 | 100 | B-1 | 8.5 | C-1/C-2 | 2,240/960 | D-4 | 2.3 | F-1 | 3 | G-1 | 30 |
| Comparative Example 25 | CJ-25 | a-25 | 100 | B-2 | 8.5 | C-1/C-2 | 2,240/960 | D-5 | 2.3 | F-1 | 3 | G-1 | 30 |
| Comparative Example 26 | CJ-26 | a-26 | 100 | B-3 | 8.5 | C-1/C-2 | 2,240/960 | D-5 | 2.3 | F-1 | 3 | G-1 | 30 |
| Comparative Example 27 | CJ-27 | a-27 | 100 | B-1 | 8.5 | C-1/C-2 | 2,240/960 | D-5 | 2.3 | F-1 | 3 | G-1 | 30 |

TABLE 4-3

| | Radiation-sensitive resin composition | (A) Component type | (A) Component amount (parts by mass) | (B) Acid generating agent type | (B) Acid generating agent amount (parts by mass) | (C) Organic solvent type | (C) Organic solvent amount (parts by mass) | (D) Acid diffusion control agent type | (D) Acid diffusion control agent amount (parts by mass) | (F) Polymer type | (F) Polymer amount (parts by mass) | (G) Uneven distribution accelerator type | (G) Uneven distribution accelerator amount (parts by mass) |
|---|---|---|---|---|---|---|---|---|---|---|---|---|---|
| Comparative Example 28 | CJ-28 | a-28 | 100 | B-2 | 8.5 | C-1/C-2 | 2,240/960 | D-5 | 2.3 | F-1 | 3 | G-1 | 30 |
| Comparative Example 29 | CJ-29 | a-29 | 100 | B-1 | 8.5 | C-1/C-2 | 2,240/960 | D-2 | 2.3 | — | — | — | — |
| Comparative Example 30 | CJ-30 | a-30 | 100 | B-2 | 8.5 | C-1/C-2 | 2,240/960 | D-2 | 2.3 | — | — | — | — |
| Comparative Example 31 | CJ-31 | a-31 | 100 | B-2 | 8.5 | C-1/C-2 | 2,240/960 | D-2 | 2.3 | — | — | — | — |
| Comparative Example 32 | CJ-32 | a-32 | 100 | B-1 | 8.5 | C-1/C-2 | 2,240/960 | D-2 | 2.3 | — | — | — | — |

TABLE 4-3-continued

| Radiation-sensitive resin composition | (A) Component type | (A) amount (parts by mass) | (B) Acid generating agent type | (B) amount (parts by mass) | (C) Organic solvent type | (C) amount (parts by mass) | (D) Acid diffusion control agent type | (D) amount (parts by mass) | (F) Polymer type | (F) amount (parts by mass) | (G) Uneven distribution accelerator type | (G) amount (parts by mass) |
|---|---|---|---|---|---|---|---|---|---|---|---|---|
| Comparative Example 33 | CJ-33 | a-33 | 100 | B-1 | 8.5 | C-1/C-2 | 2,240/960 | D-2 | 2.3 | — | — | — | — |
| Comparative Example 34 | CJ-34 | a-34 | 100 | B-1 | 8.5 | C-1/C-2 | 2,240/960 | D-1 | 2.3 | — | — | — | — |
| Comparative Example 35 | CJ-35 | a-35 | 100 | B-2 | 8.5 | C-1/C-2 | 2,240/960 | D-1 | 2.3 | — | — | — | — |
| Comparative Example 36 | CJ-36 | a-36 | 100 | B-2 | 8.5 | C-1/C-2 | 2,240/960 | D-1 | 2.3 | — | — | — | — |
| Comparative Example 37 | CJ-37 | a-37 | 100 | B-1 | 8.5 | C-1/C-2 | 2,240/960 | D-1 | 2.3 | — | — | — | — |
| Comparative Example 38 | CJ-38 | a-38 | 100 | B-1 | 8.5 | C-1/C-2 | 2,240/960 | D-1 | 2.3 | — | — | — | — |
| Comparative Example 39 | CJ-39 | a-39 | 100 | B-2 | 8.5 | C-1/C-2 | 2,240/960 | D-1 | 2.3 | — | — | — | — |
| Comparative Example 40 | CJ-40 | a-40 | 100 | B-2 | 8.5 | C-1/C-2 | 2,240/960 | D-1 | 2.3 | — | — | — | — |
| Comparative Example 41 | CJ-41 | a-41 | 100 | B-1 | 8.5 | C-1/C-2 | 2,240/960 | D-1 | 2.3 | — | — | — | — |

Formation of Resist Pattern (I)

Examples 19 to 47 and 53 to 55, and Comparative Examples 1 to 28

Formation of Resist Pattern (1): Development with Alkali

An underlayer antireflective film having a film thickness of 105 nm was provided on the surface of a 12-inch silicon wafer by applying a composition for underlayer antireflective film formation (ARC66, manufactured by Brewer Science) on the surface of the 12-inch silicon wafer using a spin coater (CLEAN TRACK ACT12, manufactured by Tokyo Electron Limited), and thereafter heating the same at 205° C. for 60 sec. Each radiation-sensitive resin composition prepared above was applied on the underlayer antireflective film using the spin coater, and subjected to PB at 90° C. for 60 sec. Thereafter, cooling was carried out at 23° C. for 30 sec to provide a resist film having a film thickness of 90 nm. Next, the resist film was exposed using an ArF excimer laser Immersion Scanner (NSR-S610C, manufactured by NIKON) through a 40 nm line-and-space (1L1S) mask pattern, under optical conditions involving NA of 1.3 and dipole (Sigma: 0.977/0.782). After the exposure, PEB was carried out at 90° C. for 60 sec. Thereafter, a development with an alkali was carried out using a 2.38% by mass aqueous TMAH solution as an alkaline developer solution, followed by washing with water and drying to form a positive resist pattern. In this resist pattern formation, an exposure dose at which a 1:1 line-and-space with a line width of 40 nm was formed through a mask for 1:1 line-and-space with a target dimension of 40 nm was defined as an "optimum exposure dose".

Formation of Resist Pattern (2): Development with Organic Solvent

A negative resist pattern was formed by a similar operation to that of the above Formation of Resist Pattern (1) except that: n-butyl acetate was used in place of the aqueous TMAH solution to execute a development with an organic solvent; and washing with water was not carried out.

Evaluations

Measurements were made on the resist patterns thus formed in accordance with the following methods to evaluate the radiation-sensitive resin composition in regard to an LWR performance, a resolution, rectangularity of the cross-sectional shape, and a depth of focus. The results of the evaluations are shown in Tables 5-1 and 5-2. For a line-width measurement of the resist pattern, a scanning electron microscope (S-9380, manufactured by Hitachi High-Technologies Corporation) was used. Comparative Examples which serve as an evaluation standard for each Example are shown together in Tables 5-1 and 5-2.

LWR Performance

The resist pattern was observed from above the pattern using the scanning electron microscope. The line width was measured at arbitrary points of 50 in total, then a 3 Sigma value was determined from the distribution of the measurements, and the value was designated as "LWR performance (nm)". The smaller value indicates a more favorable LWR performance. By comparing the "LWR performance" value with that for the Comparative Example which served as an evaluation standard, the LWR performance was evaluated to be: "A" in the case of an improvement by no less than 15% being found (i.e., the "LWR performance" value accounting for no greater than 85% of the value for the standard Comparative Example); "B" in the case of an improvement by no less than 10% and less than 15% being found (i.e., the "LWR performance" value accounting for greater than 85% and no greater than 90%); and "C" in the case of an improvement by less than 10% being found (i.e., the "LWR performance" value accounting for greater than 90%).

Resolution

A dimension of the minimum resist pattern which was resolved at the optimum exposure dose was measured, and the measurement value was designated as a "resolution (nm)". The smaller value indicates a more favorable resolution. By comparing the "resolution" value with that for the Comparative Example which served as an evaluation standard, the resolution was evaluated to be: "A" in the case of an improvement by no less than 15% being found (i.e., the "resolution" value accounting for no greater than 85% of the value for the Comparative Example); "B" in the case of an improvement by no less than 10% and less than 15% being found (i.e., the "resolution" value accounting for greater than 85% and no greater than 90%); and "C" in the case of an improvement by less than 10% being found (i.e., the "resolution" value accounting for greater than 90%).

Rectangularity of Cross-Sectional Shape

The cross-sectional shape of the resist pattern which was resolved at the optimum exposure dose was observed, and a line width Lb in the middle portion of the resist pattern and a line width La at the top of the film were measured, and then La/Lb was calculated based on each measurement value. The rectangularity of the cross-sectional shape was evaluated to be: "A" in a case where the La/Lb value fell within a range of no less than 0.95 and no greater than 1.05; "B" in a case where the La/Lb value fell within a range of no less than 0.9 and less than 0.95, or a range of greater than 1.05 and no greater than 1.1; and "C" in a case where the La/Lb value was less than 0.9 or greater than 1.1.

Depth of Focus

On the resist pattern which was resolved at the optimum exposure dose, the dimension when the focus was shifted along the depth direction was determined, and a latitude in the depth direction was determined in which the pattern dimension fell within a range of 90% to 110% of the standard while not accompanied by a bridge and/or a residue, and the measurement value was designated as a "depth of focus". The greater measurement value indicates a more favorable depth of focus. By comparing the "depth of focus" value with that for the Comparative Example which served as an evaluation standard, the depth of focus was evaluated to be: "A" in the case of an improvement by no less than 15% being found (i.e., the "depth of focus" value accounting for no less than 115% of the value for the Comparative Example); "B" in the case of an improvement by no less than 10% and less than 15% being found (i.e., the "depth of focus" value accounting for no less than 110% and less than 115%); and "C" in the case of an improvement by less than 10% (i.e., the "depth of focus" value accounting for no less than 110%).

Formation of Resist Pattern (II)

Examples 48 to 52 and 56 to 63, and Comparative Examples 29 to 41

Formation of Resist Pattern (3): Development with Alkali

An underlayer antireflective film having a film thickness of 25 nm was provided on the surface of a 12-inch silicon wafer by applying a composition for underlayer antireflective film formation on the surface of the 12-inch silicon wafer, and thereafter heating the same at 205° C. for 60 sec. Each radiation-sensitive resin composition was applied on the underlayer antireflective film, and subjected to PB at 100° C. for 60 sec. Thereafter, cooling was carried out at 23° C. for 30 sec to provide a resist film having a film thickness of 50 nm. Next, the resist film was exposed using an EUV scanner (NXE3100, manufactured by ASML) through a mask pattern for forming a resist pattern with 35 nm line-and-space (1L/1S) under optical conditions involving NA of 0.25 and dipole. After the exposure, PEB was carried out at 100° C. for 60 sec. Thereafter, a puddle development was carried out using a 2.38% by mass aqueous TMAH solution at 23° C. for 30 sec. Then, rinsing was carried out using ultra pure water for 7 sec, and thereafter spin-drying was executed for 15 sec at 2,000 rpm, whereby a 35 nm line-and-space (1L/1S) positive resist pattern was formed. An exposure dose at which a 1:1 line-and-space with a line width of 35 nm was formed was defined as an "optimum exposure dose".

Formation of Resist Pattern (4): Development with Organic Solvent

A negative resist pattern was formed by a similar operation to that of the above Formation of Resist Pattern (3) except that: n-butyl acetate was used in place of the aqueous TMAH solution to execute the development with an organic solvent; and washing with water was not carried out.

Evaluations

Evaluations were made on the resist patterns obtained above in accordance with methods similar to those in the above Formation of Resist Pattern (I). The results of the evaluations are shown in Tables 5-1 and 5-2.

TABLE 5-1

| | Radiation-sensitive resin composition | Evaluation standard | Development with alkali | | | | Development with organic solvent | | | |
|---|---|---|---|---|---|---|---|---|---|---|
| | | | LWR performance | resolution | rectangularity of cross-sectional shape | depth of focus | LWR performance | resolution | rectangularity of cross-sectional shape | depth of focus |
| Example 19 | J-1 | CJ-1 | A | A | A | A | A | A | A | B |
| Example 20 | J-2 | CJ-2 | A | B | A | A | A | A | B | A |
| Example 21 | J-3 | CJ-3 | A | A | A | A | A | A | A | A |
| Example 22 | J-4 | CJ-4 | B | B | B | A | B | B | B | B |
| Example 23 | J-5 | CJ-5 | B | B | B | B | B | B | B | B |
| Example 24 | J-6 | CJ-6 | B | A | B | B | B | A | B | A |
| Example 25 | J-7 | CJ-7 | B | B | B | B | B | B | B | B |
| Example 26 | J-8 | CJ-8 | A | B | B | B | B | A | B | B |
| Example 27 | J-9 | CJ-9 | B | B | B | B | B | B | B | B |
| Example 28 | J-10 | CJ-3 | A | A | A | A | A | A | A | A |
| Example 29 | J-11 | CJ-10 | A | B | A | A | A | A | B | A |
| Example 30 | J-12 | CJ-11 | A | A | B | A | A | A | B | A |
| Example 31 | J-13 | CJ-12 | A | A | A | A | A | A | A | A |
| Example 32 | J-14 | CJ-13 | A | A | A | B | A | B | A | A |
| Example 33 | J-15 | CJ-14 | A | A | A | A | A | A | A | A |
| Example 34 | J-16 | CJ-15 | A | B | A | A | A | B | A | A |
| Example 35 | J-17 | CJ-16 | B | B | A | B | B | B | B | B |
| Example 36 | J-18 | CJ-17 | A | A | A | A | A | A | A | A |
| Example 37 | J-19 | CJ-18 | A | A | A | A | A | A | A | A |
| Example 38 | J-20 | CJ-19 | A | A | A | A | A | A | A | A |

TABLE 5-1-continued

|  | Radiation-sensitive resin composition | Evaluation standard | Development with alkali | | | | Development with organic solvent | | | |
|---|---|---|---|---|---|---|---|---|---|---|
|  |  |  | LWR performance | resolution | rectangularity of cross-sectional shape | depth of focus | LWR performance | resolution | rectangularity of cross-sectional shape | depth of focus |
| Example 39 | J-21 | CJ-20 | B | B | B | B | A | B | B | B |
| Example 40 | J-22 | CJ-21 | B | A | B | B | A | B | A | B |
| Example 41 | J-23 | CJ-22 | B | B | A | B | B | B | B | B |
| Example 42 | J-24 | CJ-23 | A | A | A | A | A | A | A | A |
| Example 43 | J-25 | CJ-24 | B | B | B | B | B | B | B | B |
| Example 44 | J-26 | CJ-25 | A | A | A | A | A | A | A | A |

TABLE 5-2

|  | Radiation-sensitive resin composition | Evaluation standard | Development with alkali | | | | Development with organic solvent | | | |
|---|---|---|---|---|---|---|---|---|---|---|
|  |  |  | LWR performance | resolution | rectangularity of cross-sectional shape | depth of focus | LWR performance | resolution | rectangularity of cross-sectional shape | depth of focus |
| Example 45 | J-27 | CJ-26 | A | A | B | A | A | A | A | A |
| Example 46 | J-28 | CJ-27 | A | A | B | A | A | A | A | A |
| Example 47 | J-29 | CJ-28 | A | A | A | B | A | A | A | A |
| Example 48 | J-30 | CJ-29 | A | B | A | A | A | A | A | A |
| Example 49 | J-31 | CJ-30 | A | A | B | A | A | B | A | A |
| Example 50 | J-32 | CJ-31 | A | B | A | B | A | A | A | B |
| Example 51 | J-33 | CJ-32 | A | A | A | B | A | A | A | A |
| Example 52 | J-34 | CJ-33 | A | A | B | A | A | A | B | A |
| Example 53 | J-35 | CJ-18 | B | B | B | B | B | A | B | B |
| Example 54 | J-36 | CJ-21 | B | A | B | B | B | B | B | A |
| Example 55 | J-37 | CJ-1 | B | B | B | A | B | B | B | B |
| Example 56 | J-38 | CJ-34 | B | A | B | B | B | B | A | B |
| Example 57 | J-39 | CJ-35 | B | A | B | B | A | B | B | B |
| Example 58 | J-40 | CJ-36 | B | A | B | A | B | B | B | B |
| Example 59 | J-41 | CJ-37 | B | B | B | B | B | A | B | B |
| Example 60 | J-42 | CJ-38 | B | A | B | B | B | B | B | B |
| Example 61 | J-43 | CJ-39 | B | B | B | A | B | B | A | B |
| Example 62 | J-44 | CJ-40 | B | B | A | B | B | B | B | B |
| Example 63 | J-45 | CJ-41 | A | B | B | B | A | B | A | B |

As is clear from the results shown in Tables 5-1 and 5-2, in both cases of the development with an alkali and the development with an organic solvent, the radiation-sensitive resin compositions of Examples exhibited favorable LWR performance, resolution, cross-sectional shape, and depth of focus.

The radiation-sensitive resin composition and the resist pattern-forming method according to the embodiments of the present invention enable a resist pattern exhibiting a small LWR, a high resolution and superior rectangularity of the cross-sectional shape to be formed while a great depth of focus is exhibited. The polymer according to the embodiments of the present invention can be suitably used as a polymer component of the radiation-sensitive resin composition. The production method of a compound according to the embodiments of the present invention enables a compound suitable for a basic ingredient of the polymer to be produced conveniently in a favorable yield. Therefore, these can be suitably used for the production of semiconductor devices, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:

a polymer comprising a first structural unit represented by formula (1-1) or (1-2), a content of the polymer with respect to a total solid content of the radiation-sensitive composition being no less than 25% by mass;

a radiation-sensitive acid generator; and an organic solvent,

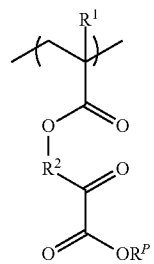

(1-1)

-continued

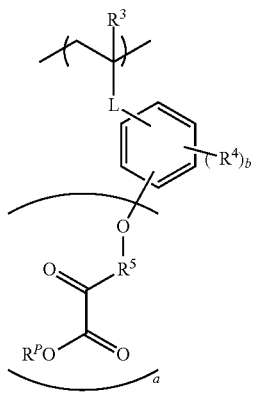
(1-2)

wherein in the formulae (1-1) and (1-2),
$R^P$ represents a monovalent organic group which is an acid-nonlabile group, wherein in the formula (1-1),
$R^1$ represents a hydrogen atom, or a substituted or unsubstituted alkyl group having 1 to 5 carbon atoms; and
$R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof, and
wherein in the formula (1-2),
$R^3$ represents a hydrogen atom, or a substituted or unsubstituted alkyl group having 1 to 5 carbon atoms;
L represents a single bond, —COO— or —CONR$^N$—, wherein $R^N$ represents a hydrogen atom or a monovalent hydrocarbon group having 1 to 10 carbon atoms;
$R^4$ represents an alkyl group having 1 to 5 carbon atoms, an alkoxy group having 1 to 5 carbon atoms or an acyl group having 2 to 5 carbon atoms;
$R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof;
"a" is an integer of 1 to 5; and
"b" is an integer of 0 to 4,
wherein a sum of "a" and "b" is no greater than 5, and in a case where $R^P$, $R^4$ and $R^5$ are each present in a plurality of number, a plurality of $R^P$s are each identical or different, a plurality of $R^4$s are each identical or different and a plurality of $R^5$s are each identical or different.

2. The radiation-sensitive resin composition according to claim 1, wherein the acid-nonlabile group is:
(1) a group obtained by substituting a part or all of hydrogen atoms comprised in a monovalent hydrocarbon group having 1 to 20 carbon atoms with a polar group;

(2) a group obtained from a monovalent hydrocarbon group having 2 to 20 carbon atoms by incorporating between adjacent two carbon atoms thereof, —O—, —CO—, —COO—, —SO$_2$O— or a combination thereof; or
(3) a group obtained from a monovalent hydrocarbon group having 2 to 20 carbon atoms by incorporating between adjacent two carbon atoms thereof, —O—, —CO—, —COO—, —SO$_2$O— or a combination thereof and substituting a part or all of hydrogen atoms thereof with a polar group.

3. The radiation-sensitive resin composition according to claim 2, wherein the acid-nonlabile group is the group (2) obtained from a monovalent hydrocarbon group having 2 to 20 carbon atoms by incorporating between adjacent two carbon atoms thereof, —O—, —CO—, —COO—, —SO$_2$O— or a combination thereof.

4. The radiation-sensitive resin composition according to claim 2, wherein the acid-nonlabile group is the group (1) obtained by substituting a part or all of hydrogen atoms comprised in a monovalent hydrocarbon group having 1 to 20 carbon atoms with a polar group.

5. A resist pattern-forming method comprising:
applying the radiation-sensitive resin composition according to claim 1 on a substrate to provide a resist film on the substrate;
exposing the resist film; and
developing the exposed resist film.

6. A radiation-sensitive resin composition comprising:
a polymer comprising a first structural unit represented by formula (1-1) or (1-2), a content of the polymer with respect to a total solid content of the radiation-sensitive composition being no less than 25% by mass;
an acid-labile group-containing polymer other than the polymer comprising the first structural unit;
a radiation-sensitive acid generator; and
an organic solvent,

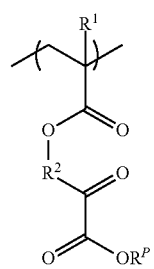
(1-1)

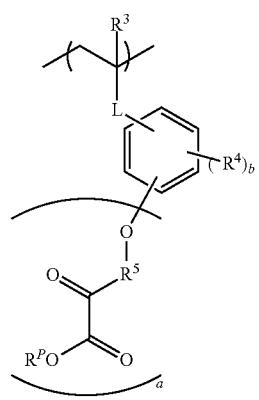
(1-2)

wherein in the formulae (1-1) and (1-2),
- $R^P$ represents a hydrogen atom or a monovalent organic group, wherein in the formula (1-1),
- $R^1$ represents a hydrogen atom, or a substituted or unsubstituted alkyl group having 1 to 5 carbon atoms; and
- $R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof, and wherein in the formula (1-2),
- $R^3$ represents a hydrogen atom, or a substituted or unsubstituted alkyl group having 1 to 5 carbon atoms;
- L represents a single bond, —COO— or —CONR$^N$—, wherein $R^N$ represents a hydrogen atom or a monovalent hydrocarbon group having 1 to 10 carbon atoms;
- $R^4$ represents an alkyl group having 1 to 5 carbon atoms, an alkoxy group having 1 to 5 carbon atoms or an acyl group having 2 to 5 carbon atoms;
- $R^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof;
- "a" is an integer of 1 to 5; and
- "b" is an integer of 0 to 4,
  wherein a sum of "a" and "b" is no greater than 5, and in a case where $R^P$, $R^4$ and $R^5$ are each present in a plurality of number, a plurality of $R^P$s are each identical or different, a plurality of $R^4$s are each identical or different and a plurality of $R^5$s are each identical or different.

7. The radiation-sensitive resin composition according to claim 6, wherein a content of the acid-labile group-containing polymer with respect to 100 parts by mass of the polymer comprising the first structural unit is from 20 parts by mass to 200 parts by mass.

8. The radiation-sensitive resin composition according to claim 6, wherein $R^P$ in the formula (1) represents a monovalent organic group, and the monovalent organic group is an acid-labile group.

9. The radiation-sensitive resin composition according to claim 8, wherein the acid-labile group is represented by formula (p):

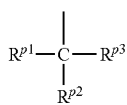

(p)

wherein in the formula (p),
- $R^{p1}$ represents a hydrogen atom or a monovalent chain hydrocarbon group having 1 to 10 carbon atoms; and $R^{p2}$ and $R^{p3}$ each independently represent a monovalent chain hydrocarbon group having 1 to 10 carbon atoms or a monovalent alicyclic hydrocarbon group having 3 to 20 carbon atoms, or taken together represent a ring structure having 3 to 20 ring atoms, together with the carbon atom to which $R^{p2}$ and $R^{p3}$ bond.

10. The radiation-sensitive resin composition according to claim 6, wherein the polymer further comprises a second structural unit represented by formula (2):

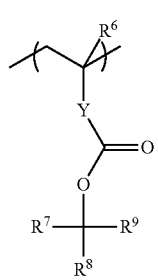

(2)

wherein in the formula (2),
- $R^6$ represents a hydrogen atom, a fluorine atom, a methyl group or a trifluoromethyl group;
- Y represents a single bond, a carbonyloxycycloalkanediyl group having 4 to 20 carbon atoms, a carbonyloxycycloalkanediyloxy group having 4 to 20 carbon atoms, an arenediyl group having 6 to 20 carbon atoms, or a carbonyloxyarenediyl group having 7 to 20 carbon atoms;
- $R^7$ represents a monovalent chain hydrocarbon group having 1 to 10 carbon atoms or a monovalent alicyclic hydrocarbon group having 3 to 20 carbon atoms; and
- $R^8$ and $R^9$ each independently represent a monovalent chain hydrocarbon group having 1 to 10 carbon atoms or a monovalent alicyclic hydrocarbon group having 3 to 20 carbon atoms, or taken together represent an alicyclic structure having 3 to 20 carbon atoms, together with the carbon atom to which $R^8$ and $R^9$ bond.

11. The radiation-sensitive resin composition according to claim 6, wherein the polymer further comprises a structural unit represented by formula (3-1), a structural unit represented by formula (3-2), a structural unit represented by formula (3-3), a structural unit represented by formula (3-4), or a combination thereof:

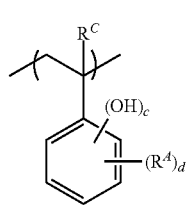

(3-1)

-continued

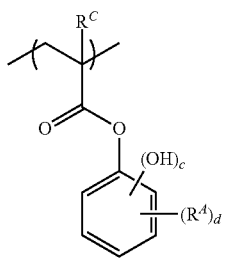

(3-2)

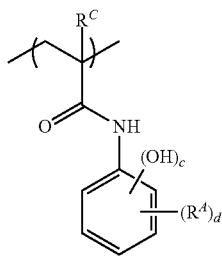

(3-3)

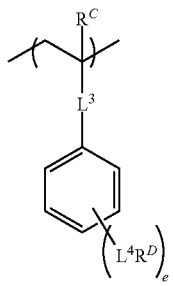

(3-4)

wherein in the formulae (3-1) to (3-4),
$R^C$s each independently represent a hydrogen atom or an alkyl group having 1 to 5 carbon atoms, and
wherein in the formulae (3-1) to (3-3),
"c" s are each independently an integer of 1 to 3;
$R^A$s each independently represent an alkyl group having 1 to 5 carbon atoms; and
"d" s are each independently an integer of 0 to 4,
wherein a sum of c and d is no greater than 5, and
wherein in a case where $R^A$ is present in a plurality of number, a plurality of $R^A$s are each identical or different, and
wherein in the formula (3-4),
$L^3$ and $L^4$ each independently represent a single bond, a methylene group, an alkylene group having 2 to 5 carbon atoms, a cycloalkylene group having 3 to 15 carbon atoms, an arylene group having 6 to 20 carbon atoms, or a divalent group obtained by combining a methylene group, an alkylene group having 2 to 5 carbon atoms, a cycloalkylene group having 3 to 15 carbon atoms or an arylene group having 6 to 20 carbon atoms with —O—, —CO— or a combination thereof;
$R^D$ represents a hydrogen atom, a carboxy group, a monovalent chain hydrocarbon group having 1 to 5 carbon atoms, an alkoxy group having 1 to 5 carbon atoms, an alkoxycarbonyl group having 2 to 5 carbon atoms, or a group that comprises a hydroxy group at an end thereof and comprises at least one fluorine atom or fluorinated alkyl group on a carbon atom adjacent to the hydroxy group; and
e is an integer of 1 to 5, wherein in a case where $L^4$ and $R^D$ are each present in a plurality of number, a plurality of $L^4$s are each identical or different and a plurality of $R^D$s are each identical or different.

12. A resist pattern-forming method comprising:
applying the radiation-sensitive resin composition according to claim 6 on a substrate to provide a resist film on the substrate;
exposing the resist film; and
developing the exposed resist film.

13. A radiation-sensitive resin composition comprising:
a polymer comprising a first structural unit represented by formula (1-1) or (1-2), a content of the polymer with respect to a total solid content of the radiation-sensitive composition being no less than 25% by mass;
a fluorine atom-containing polymer other than the polymer comprising the first structural unit;
a radiation-sensitive acid generator; and
an organic solvent,

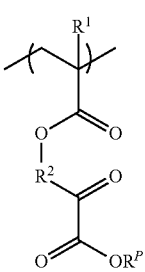

(1-1)

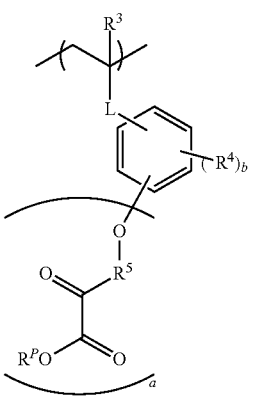

(1-2)

wherein in the formulae (1-1) and (1-2),
$R^P$ represents a hydrogen atom or a monovalent organic group, wherein in the formula (1-1),
$R^1$ represents a hydrogen atom, or a substituted or unsubstituted alkyl group having 1 to 5 carbon atoms; and
$R^2$ represents a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof, and
wherein in the formula (1-2),
$R^3$ represents a hydrogen atom, or a substituted or unsubstituted alkyl group having 1 to 5 carbon atoms;

L represents a single bond, —COO— or —CONR$^N$—, wherein R$^N$ represents a hydrogen atom or a monovalent hydrocarbon group having 1 to 10 carbon atoms;

R$^4$ represents an alkyl group having 1 to 5 carbon atoms, an alkoxy group having 1 to 5 carbon atoms or an acyl group having 2 to 5 carbon atoms;

R$^5$ represents a single bond, a methylene group, an alkylene group having 2 to 10 carbon atoms, a cycloalkylene group having 3 to 20 carbon atoms, an arylene group having 6 to 20 carbon atoms, or a group obtained from an alkylene group having 2 to 10 carbon atoms or a cycloalkylene group having 3 to 20 carbon atoms by incorporating between adjacent two carbon atoms thereof, —CO—, —COO—, —SO$_2$O— or a combination thereof;

"a" is an integer of 1 to 5; and

"b" is an integer of 0 to 4, wherein a sum of "a" and "b" is no greater than 5, and in a case where R$^P$, R$^4$ and R$^5$ are each present in a plurality of number, a plurality of R$^P$s are each identical or different, a plurality of R$^4$s are each identical or different and a plurality of R$^5$s are each identical or different.

14. The radiation-sensitive resin composition according to claim 13, wherein a content of the fluorine atom-containing polymer in the radiation-sensitive resin composition with respect to 100 parts by mass of the polymer comprising the first structural unit is from 0.5 parts by mass to 15 parts by mass.

15. The radiation-sensitive resin composition according to claim 13, wherein R$^P$ in the formula (1) represents a monovalent organic group, and the monovalent organic group is an acid-labile group.

16. The radiation-sensitive resin composition according to claim 15, wherein the acid-labile group is represented by formula (p):

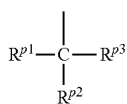

(p)

wherein in the formula (p),

R$^{p1}$ represents a hydrogen atom or a monovalent chain hydrocarbon group having 1 to 10 carbon atoms; and R$^{p2}$ and R$^{p3}$ each independently represent a monovalent chain hydrocarbon group having 1 to 10 carbon atoms or a monovalent alicyclic hydrocarbon group having 3 to 20 carbon atoms, or taken together represent a ring structure having 3 to 20 ring atoms, together with the carbon atom to which R$^{p2}$ and R$^{p3}$ bond.

17. The radiation-sensitive resin composition according to claim 13, wherein the polymer further comprises a second structural unit represented by formula (2):

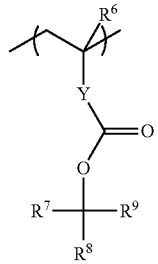

(2)

wherein in the formula (2),

R$^6$ represents a hydrogen atom, a fluorine atom, a methyl group or a trifluoromethyl group;

Y represents a single bond, a carbonyloxycycloalkanediyl group having 4 to 20 carbon atoms, a carbonyloxycycloalkanediyloxy group having 4 to 20 carbon atoms, an arenediyl group having 6 to 20 carbon atoms, or a carbonyloxyarenediyl group having 7 to 20 carbon atoms;

R$^7$ represents a monovalent chain hydrocarbon group having 1 to 10 carbon atoms or a monovalent alicyclic hydrocarbon group having 3 to 20 carbon atoms; and R$^8$ and R$^9$ each independently represent a monovalent chain hydrocarbon group having 1 to 10 carbon atoms or a monovalent alicyclic hydrocarbon group having 3 to 20 carbon atoms, or taken together represent an alicyclic structure having 3 to 20 carbon atoms, together with the carbon atom to which R$^8$ and R$^9$ bond.

18. The radiation-sensitive resin composition according to claim 13, wherein the polymer further comprises a structural unit represented by formula (3-1), a structural unit represented by formula (3-2), a structural unit represented by formula (3-3), a structural unit represented by formula (3-4), or a combination thereof:

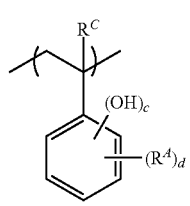

(3-1)

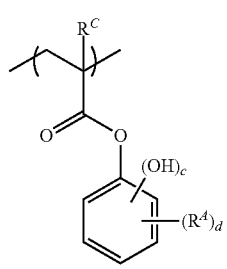

(3-2)

-continued (3-3)

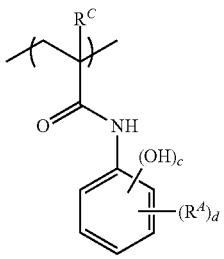

(3-4)

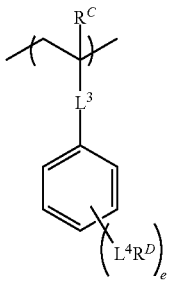

wherein in the formulae (3-1) to (3-4),
$R^C$s each independently represent a hydrogen atom or an alkyl group having 1 to 5 carbon atoms, and wherein in the formulae (3-1) to (3-3),
"c" s are each independently an integer of 1 to 3;
$R^A$s each independently represent an alkyl group having 1 to 5 carbon atoms; and
"d" s are each independently an integer of 0 to 4, wherein a sum of c and d is no greater than 5, and wherein in a case where $R^A$ is present in a plurality of number, a plurality of $R^A$s are each identical or different, and wherein in the formula (3-4),
$L^3$ and $L^4$ each independently represent a single bond, a methylene group, an alkylene group having 2 to 5 carbon atoms, a cycloalkylene group having 3 to 15 carbon atoms, an arylene group having 6 to 20 carbon atoms, or a divalent group obtained by combining a methylene group, an alkylene group having 2 to 5 carbon atoms, a cycloalkylene group having 3 to 15 carbon atoms or an arylene group having 6 to 20 carbon atoms with —O—, —CO— or a combination thereof;

$R^D$ represents a hydrogen atom, a carboxy group, a monovalent chain hydrocarbon group having 1 to 5 carbon atoms, an alkoxy group having 1 to 5 carbon atoms, an alkoxycarbonyl group having 2 to 5 carbon atoms, or a group that comprises a hydroxy group at an end thereof and comprises at least one fluorine atom or fluorinated alkyl group on a carbon atom adjacent to the hydroxy group; and e is an integer of 1 to 5,
wherein in a case where $L^4$ and $R^D$ are each present in a plurality of number, a plurality of $L^4$s are each identical or different and a plurality of $R^D$s are each identical or different.

19. A resist pattern-forming method comprising:
applying the radiation-sensitive resin composition according to claim 13 on a substrate to provide a resist film on the substrate;
exposing the resist film; and
developing the exposed resist film.

* * * * *